(12) United States Patent
Hertzberg et al.

(10) Patent No.: US 9,018,448 B2
(45) Date of Patent: Apr. 28, 2015

(54) WOODY PLANTS HAVING IMPROVED GROWTH CHARACTERISTICS AND METHOD FOR MAKING THE SAME

(75) Inventors: Magnus Hertzberg, Umeå (SE); Göran Sandberg, Umeå (SE); Jarmo Schrader, Umeå (SE); Carl David Jonsén, Umeå (SE)

(73) Assignee: SweTree Technologies AB, Umeå (SE)

( * ) Notice: Subject to any disclaimer, the term of this patent is extended or adjusted under 35 U.S.C. 154(b) by 1359 days.

(21) Appl. No.: 12/518,086

(22) PCT Filed: Dec. 4, 2007

(86) PCT No.: PCT/SE2007/050939
§ 371 (c)(1),
(2), (4) Date: Jan. 10, 2011

(87) PCT Pub. No.: WO2008/069747
PCT Pub. Date: Jun. 12, 2008

(65) Prior Publication Data
US 2012/0180163 A1    Jul. 12, 2012

(30) Foreign Application Priority Data
Dec. 8, 2006  (WO) ................ PCT/EP2006/011855

(51) Int. Cl.
| | | |
|---|---|---|
| C12N 15/82 | (2006.01) | |
| C12N 15/113 | (2010.01) | |
| A01H 7/00 | (2006.01) | |
| C07H 21/02 | (2006.01) | |

(52) U.S. Cl.
CPC .................................. C12N 15/8255 (2013.01)

(58) Field of Classification Search
None
See application file for complete search history.

(56) References Cited

U.S. PATENT DOCUMENTS

| | | | |
|---|---|---|---|
| 4,987,071 A | 1/1991 | Cech et al. | |
| 5,107,065 A | 4/1992 | Shewmaker et al. | |
| 5,231,020 A | 7/1993 | Jorgensen et al. | |
| 5,543,508 A | 8/1996 | Haseloff et al. | |
| 5,583,021 A | 12/1996 | Dougherty et al. | |
| 6,506,559 B1 | 1/2003 | Fire et al. | |
| 6,573,099 B2 | 6/2003 | Graham | |
| 2005/0044591 A1* | 2/2005 | Yao et al. ....................... | 800/287 |

FOREIGN PATENT DOCUMENTS

| | | |
|---|---|---|
| CN | 103031330 A | 4/2013 |
| WO | WO-96/06166 A1 | 2/1996 |
| WO | WO-98/53057 A1 | 11/1998 |
| WO | WO-99/53050 A1 | 10/1999 |
| WO | WO-99/53083 A1 | 10/1999 |
| WO | WO-99/61631 A1 | 12/1999 |
| WO | 01/66777 A1 | 9/2001 |
| WO | WO-03/066852 A2 | 8/2003 |
| WO | WO-2004/097024 A1 | 11/2004 |
| WO | 2006/040685 A2 | 4/2006 |
| WO | WO-2006/040684 A2 | 4/2006 |
| WO | 2006/068603 A1 | 6/2006 |
| WO | WO-2006/078431 A1 | 7/2006 |

OTHER PUBLICATIONS

Sterky et al (PNAS, 101(38), p. 13951-13956, 2004).*
Hu et al (Nature Biotechnology, 17(8), p. 808-812, 1999).*
Schrader et al (Plant Cell, 16, p. 2278-2292, 2004).*
Wesley et al (The Plant Journal, 27(6), p. 581-590, 2001).*
Delledonne et al (Molecular Breeding, 7, p. 35-42, 2001).*
Rottmann et al (Plant Journal, 22(3), p. 235-245, 2000).*
Holtorf et al (Naturwissenschaften, 89, p. 235-249, 2002).*
Elbashir et al (Genes and Dev, 15, p. 188-200, 2001).*
Hellgren (Ehtylene and Auxin in the Control of Wood Formation, Doctoral Thesis Swedish University of Agricultural Sciences, published in Feb. 2003).*
Dai et al (Nucl. Acids Res., 30(16), e86, 2002).*
Strauss et al (BMC Proceedings, 5(Suppl 7);I25, 2011).*
Rual et al (BMC Genomics, 8(106), 2007).*
Office Action received for New Zeland Patent Application No. 577854, mailed on Jul. 27, 2010, 2 pages.
Office Action received for Chinese Patent Application No. 200780045384.7, mailed on Aug. 10, 2011, 12 pages (7 pages of English Translation and 5 pages of Office Action).
Office Action received for Chinese Patent Application No. 200780045384.7, mailed on Apr. 1, 2012, 11 pages (7 pages of English Translation and 4 pages of Office Action).
Office Action received for Chilean Patent Application No. 3530-07, received on Apr. 13, 2012, 9 pages of Official Copy only.
Office Action received for Japanese Patent Application No. 2009-540207, mailed on Jan. 4, 2013, 13 pages (7 pages of English Translation and 6 pages).
Eriksson, M. E. et al. (Jul. 2000). "Increased Gibberellin Biosynthesis in Transgenic Trees Promotes Growth, Biomass Production and Xylem Fiber Length," *Nature Biotechnology* 18:784-788.

(Continued)

Primary Examiner — David T Fox
Assistant Examiner — Stephen Uyeno
(74) Attorney, Agent, or Firm — Morrison & Foerster LLP

(57) ABSTRACT

The present invention pertains to a novel and extensive analytical platform for selecting genes with a possible commercial phenotype from a large group of candidate genes identified using tools in bioinformatics, data from EST sequencing and DNA array. An aspect of the invention provides a method of producing a transgenic plant having an increased growth compared to its wild type. The method comprises altering in the plant the level of a gene product of at least one gene specifically expressed during different phases of wood formation. Further aspects of the invention provide a plant cell or plant progeny of a transgenic plant comprising a recombinant polynucleotide according to the invention. Other aspects pertain a DNA construct comprising a nucleotide sequence of the invention and a plant cell or plant progeny comprising the DNA construct.

12 Claims, 5 Drawing Sheets

(56) References Cited

OTHER PUBLICATIONS

GenBank Accession No. Al162169, last updated Dec. 3, 1998, located at <http://www.ncbi.nlm.nih.gov/nucest/3853454?report=genbank&log$=seqview> visited on May 20, 2009. (2 pages).

Hertzberg, M. et al. (Dec. 4, 2001). "A Transcriptional Roadmap to Wood Formation," *Proceedings of the National Academy of Sciences of the United States of America* 98(25):14732-14737.

Hu, W.-J. et al. (Aug. 1999). "Repression of Lignin Biosynthesis Promotes Cellulose Accumulation and Growth in Transgenic Trees," *Nature Biotechnology* 17:808-812.

International Search Report mailed May 20, 2008, for PCT Application No. PCT/SE2007/050939 filed Dec. 4, 2007, 4 pages.

International Written Opinion mailed May 20, 2008, for PCT Application No. PCT/SE2007/050939 filed Dec. 4, 2007, 8 pages.

Schrader, J. et al. (Sep. 2004). "A High-Resolution Transcript Profile Across the Wood-Forming Meristem of Poplar Identifies Potential Regulators of Cambial Stem Cell Identity," *The Plant Cell* 16:2278-2292.

Sterky, F. et al. (Oct. 1998). "Gene Discovery in the Wood-Forming Tissues of Poplar: Analysis of 5,692 Expressed Sequence Tags," *Proceedings of the National Academy of Sciences of the United States of America* 95:13330-13335.

Extended European Search Report received for European Patent Application No. 07852211.7, mailed on Nov. 19, 2010, 10 pages.

Israelsson et al., "Changes in gene expression in the wood-forming tissue of transgenic hybrid aspen with increased secondary growth", Plant Molecular Biology, vol. 52, 2003, pp. 893-903.

Sederoff, Ron, "Building better trees with antisense", Nature Biotechnology, vol. 17, 1999, pp. 750-751.

"WS02542.B21_E07 PT-MB-N-A-15 *Populus trichocarpa* cDNA done WS02542_E07 3', mRNA sequence", Database EMBL (Online), XP-002448807, retrieved from EBI Accession No. EMBL : DT489450, Sep. 6, 2005, 2 pages.

Aharoni, A. et al. (May 2000). "Identification of the SAAT Gene Involved in Strawberry Flavor Biogenesis by Use of DNA Microarrays," *The Plant Cell* 12:647-661.

Brummell, D. A. et al. (2003). "Inverted Repeat of a Heterologous 3'-Untranslated Region for High-Efficiency, High-Throughput Gene Silencing," *The Plant Journal* 33:793-800.

Ichikawa, T. et al. (Dec. 18-25, 1997). "Identification and Role of Adenylyl Cyclase in Auxin Signalling in Higher Plants," *Nature* 390:698-701. (Retraction attached, Nov. 26, 1998, 396:390).

Kakimoto, T. (Nov. 8, 1996). "CKI1, a Histidine Kinase Homolog Implicated in Cytokinin Signal Transduction," *Science* 274:982-985.

Karimi, M. et al. (May 2002). "GATEWAY Vectors for Agrobacterium-Mediated Plant Transformation," *TRENDS in Plant Science* 7(5):193-195.

Niu, Q.-W. et al. (Nov. 2006). "Expression of Artificial MicroRNAs in Transgenic *Arabidopsis thaliana* Confers Virus Resistance," *Nature Biotechnology* 24(11):1420-1428. (Corrigendum attached, Feb. 2007, 25(2):254).

Rognes, T. (2001). "ParAlign: A Parallel Sequence Alignment Algorithm for Rapid and Sensitive Database Searches," *Nucleic Acids Research* 29(7):1647-1652.

Schena, M. et al. (Oct. 20, 1995). "Quantitative Monitoring of Gene Expression Patterns with a Complementary DNA Microarray," *Science* 270:467-470.

Slade, A. J. et al. (2005). "TILLING Moves Beyond Functional Genomics into Crop Improvement," *Transgenic Research* 14:109-115.

Smith, T. F. et al. (1981). "Identification of Common Molecular Subsequences," *Journal of Molecular Biology* 147:195-197.

Till, B. J. et al. (2004). "Mismatch Cleavage by Single-Strand Specific Nucleases," *Nucleic Acids Research* 32(8):2632-2641.

Tuskan, G. A. et al. (Sep. 15, 2006). "The Genome of Black Cottonwood, *Populus trichocarpa* (Torr. & Gray)," *Science* 313:1596-1604.

Uggla, C. et al. (Aug. 1996). "Auxin as a Positional Signal in Pattern Formation in Plants," *Proceedings of the National Academy of Sciences of the United States of America* 93:9282-9286.

Wesley, S. V. et al. (2001). "Construct Design for Efficient, Effective and High-Throughput Gene Silencing in Plants," *The Plant Journal* 27(6):581-590.

White, K. P. et al. (Dec. 10, 1999). "Microarray Analysis of *Drosophila* Development During Metamorphosis," *Science* 286:2179-2184.

Wilson, B. F. et al. (1966). "Notes: Differentiation of Cambial Derivatives: Proposed Terminology," *Forest Science* 12(4):438-440.

Extended European Search Report received for European Patent Application No. 12174452.8 mailed on Jan. 23, 2013, 7 pages.

Database EMBI, "UB12CPE03.3pr Populus active cambium cDNA library *Populus tremula* cDNA clone UB12CPEO3 3, mRNA sequence.", retrieved from http://ibis.internal.epo.org/exam/dbfetch.jsp?id=EM_EST:CK096393 on Jan. 9, 2013, 1 page.

Sterky et al., "A Populus EST resource for plant functional genomics", PNAS, vol. 101, No. 38, Sep. 21, 2004, pp. 13951-13956.

Office Action received for Chilean Patent Application No. 3530-07, received on Feb. 15, 2013. 9 pages. See Statement Under 37 CFR § 1.98(a) (3).

Office Action received for Australian Patent Application No. 2007328522, issued on Jul. 5, 2013, 3 pages.

Office Action received for Canadian Patent Application No. 2,671,656, mailed on Feb. 5, 2014, 2 pages.

Jayashree et al., "Genetic Transformation and Regeneration of Rubber Tree (*Hevea brasiliensis* Muell Arg) Transgenic Plants with a Constitutive Version of an Anti-Oxidative Stress Superoxide Dismutase Gene", Plant Cell Report, vol. 22, 2003, pp. 201-209.

Jing et al., "Expression of Choline Oxidase Gene in Transformed *Populus simonii* x *P. nigra* Improves Salt Stress Tolerance", Zhiwuxue Tongbao, vol. 25, No. 1, 2008, pp. 80-84 (1 page English Abstract only).

Matsunaga et al., "*Agrobacterium*-Mediated Transformation of Eucalyptus Globulus Using Explants with Shoot Apex with Introduction of Bacterial Choline Oxidase Gene to Enhance Salt Tolerance", Plant Cell Report, vol. 31, 2012, pp. 225-235.

Merkle et al., "Hardwood Tree Biotechnology", In Vitro Cellular & Developmental Biology—Plant, vol. 41, Sep.-Oct. 2005, pp. 602-619.

Petri et al., "*Agrobacterium*-Mediated Transformation of Apricot (*Prunus armeniaca* L.) Leaf Explants", Plant Cell Report, vol. 27, 2008, pp. 1317-1324.

Petri et al., "Highly Efficient Transformation Protocol for Plum ( *Prunus domestica* L.)", Methods in Molecular Biology, vol. 847, Chapter 16, 2012, pp. 191-199.

Song et al., "Transformation of Montmorency Sour Cherry (*Prunus cerasus* L.) and Gisela 6 (*P. cerasus* x *P. canescens*) Cherry Rootstock Mediated by *Agrobacterium tumefaciens*", Plant Cell Report, vol. 25, 2006, pp. 117-123.

Southerton, Simon G., "Early Flowering Induction and *Agrobacterium* Transformation of the Hardwood Tree Species Eucalyptus Occidentalis", Functional Plant Biology, vol. 34, 2007, pp. 707-713.

Tournier et al., "An Efficient Procedure to Stable Introduce Genes into an Economically Important Pulp Tree (*Eucalyptus grandis* x *Eucalyptus urophylla*)", Transgenic Research, vol. 12, 2003, pp. 403-411.

Vengadesan et al., "Transgenic Acacia Sinuata from *Agrobacterium tumefaciens*-Mediated Transformation of Hypocotyls", Plant Cell Report, vol. 25, 2006, pp. 1174-1180.

Yang et al., "*Agrobacterium tumefaciens*-Mediated Genetic Transformation of *Salix matsudana* Koidz. Using Mature Seeds", Tree Physiology, vol. 33, 2013, pp. 628-639.

Office Action received for Japanese Patent Application No. 2013-103815, mailed on Sep. 16, 2014, 8 pages (4 pages of English Translation).

\* cited by examiner

WOODY PLANTS HAVING IMPROVED GROWTH CHARACTERISTICS AND METHOD FOR MAKING THE SAME

CROSS REFERENCE TO RELATED APPLICATIONS

This is a U.S. National Phase patent application of PCT/SE2007/050939, filed Dec. 4, 2007, which claims priority to European patent application Ser. No. PCT/EP2006/011855, filed Dec. 8, 2006, all of which are hereby incorporated by reference in the present disclosure in their entirety.

TECHNICAL FIELD OF THE INVENTION

The present invention relates generally to the field of molecular biology and relates to a method for improving plant growth characteristics. More specifically, the invention relates to a method for phenotypically modifying plants and transgenic plants having altered expression of a gene specifically expressed during different phases of wood formation resulting in a modified growth phenotype. The invention also provides constructs useful in the method of the invention.

BACKGROUND OF THE INVENTION

At present, the primary objectives of forest-tree engineering and molecular breeding are to improve wood quality and yield. The global demand for wood products is growing at around 1.7% annually, and this increase in wood consumption is occurring despite the fact that the maximum sustainable rate of harvesting from the worlds forests has already been reached or exceeded. Therefore, there is a need for increases in plantation wood production worldwide. Forestry plantations may also have advantages as a carbon sequestration crop in response to increasing atmospheric $CO_2$. Similarly, increased production of biomass from non-woody plants is desirable, for instance in order to meet the demand for raw material for energy production. Modification of specific processes during cell development in higher species is therefore of great commercial interest, not only when it comes to improving the properties of trees, but also other plants.

Plant growth by means of apical meristems results in the development of sets of primary tissues and in lengthening of the stem and roots. In addition to this primary growth, tree species undergo secondary growth and produce the secondary tissue "wood" from the cambium. The secondary growth increases the girth of stems and roots.

Sterky et al. 1998 (Proc. Natl. Acad. Sci. USA, 1998 (95), 13330-13335) have published the results of a large-scale gene discovery program in two poplar species, comprising 5,629 expressed sequence tags (ESTs) from the wood forming tissues of *Populus tremula* L.x*tremuloides* Michx. and *Populus trichocarpa* 'Trichobel.' These ESTs represented a total of 3,719 unique transcripts for the two cDNA libraries and putative functions could be assigned to 2,245 of these transcripts. The authors state that the EST data presented will be valuable in identifying genes involved in the formation of secondary xylem and phloem in plants, but fail to give clear directions as to how the identification could be performed. The Sterky et al. 1998 paper also revealed the existence of a very large number of ESTs with unknown or uncertain functions.

In the prior art (e.g. Sterky et al. 1998) libraries were constructed from stem tissue isolated from actively growing trees. A cambial region library was prepared from a mix of tissues, including the developing xylem, the meristematic cambial zone, and developing and mature phloem of *P. Tremula*x*tremuloides* Michx. These cambial tissues were obtained by peeling the bark and scraping both exposed surfaces with a scalpel. A developing-xylem library was prepared from *Populus trichocarpa* Tricobel. These tissues were obtained by peeling the bark and scraping the exposed xylem side. Using such methods it is only possible to build three different libraries representing the whole cambial region, the developing-xylem and the phloem region (made from scraping the exposed bark). The prior art compared the expression of genes in the cambial-region with the genes expressed in the developing xylem tissue. The experiment only allowed a crude comparison due to the limits imposed by the tissue preparation protocol. The tissue used for the developing xylem library would contain tissues from expanding xylem cells through to late xylem development.

One problem remaining is how to identify the potentially most important genes and to relate these to specific developmental stages and final properties of the cell. Another problem is how to identify hitherto unknown genes, related to specific cell types and/or functions in the plant. Finally, a particular problem is how to find the specific genes involved in cell division, cell expansion, cell wall synthesis, apoptosis and programmed cell death and other important processes involved in determining tree growth and wood properties.

Hertzberg et al. 2001 (Proc. Natl. Acad. Sci. USA, 2001 (98), 14372-14737), and Schrader et al. 2005 (Plant Cell, (16), 2278-2292) have used transcript profiling to reveal a transcriptional hierarchy for thousands of genes during xylem development as well as providing expression data that can facilitate further elucidation of many genes with unknown function (White et al. 1999 (Science 1999 (286) 2187-2184); Aharoni et al. 2000 (Plant Cell 2000 (12) 647-662). This is however technically demanding in woody plants such as trees. Hertzberg et al. and Schrader et al. have studied the developing secondary xylem of poplar, which is highly organized with easily recognized and distinct boundaries between the different developmental stages. Wood formation is initiated in the vascular cambium. Cambial derivatives develop into xylem cells through the processes of division, expansion, secondary wall formation, lignification and, finally, programmed cell death. The large physical size of the vascular meristem in trees offers a unique possibility to obtain samples from defined developmental stages by tangential cryo sectioning (Uggla et al. 1996 Proc. Natl. Acad. Sci. USA, 1996 (93), 9282-9286). To determine the steady state mRNA levels at specific stages during the ontogeny of wood formation in *Populus tremula*x*tremuloides* (hybrid aspen) 30 μm thick sections through the wood development region were sampled and subsequently analyzed using several spotted cDNA-microarray (Schena et al. 1995 Science 1995 (270) 467-470) consisting of up to 20.000 unique ESTs from hybrid aspen.

Although it is obvious that results from EST programs, genome sequencing and expression studies using DNA array technologies can verify where and when a gene is expressed it is rarely possible to clarify the biological and/or technical function of a gene only from these types of analytical tools. In order to analyze and verify the gene function a functional characterization must be performed, e.g. by gene inactivation and/or gene over-expression. However, in order to be able to identify genes with interesting and most often unexpected commercial features, there is a need for novel analytical platforms evaluating candidate genes based on multiple criteria.

SUMMARY OF THE INVENTION

The present invention pertains to a novel and extensive analytical platform for selecting genes with a possible commercial phenotype from a large group of candidate genes identified using tools in bioinformatics, data from EST sequencing and DNA array. The analytical platform is concentrated on analyses of growth behavior based on a combination of multiple criteria. The invention provides a method for producing a transgenic plant by changing the expression of one or more genes selected from a group of genes which fulfil said criteria.

Thus, an aspect of the present invention provides a method of producing a transgenic plant having an increased growth compared to its wild type, comprising altering in the plant the level of a gene product of at least one gene specifically expressed during different phases of wood formation.

In a particular embodiment of the invention, the at least one gene is selected for conforming to the criteria that RNAi down-regulation of said gene in a group of 3-8 transgenic plants causes:
  a) a difference of 5% or more in average final height (AFH) and maximum final height (MFH) and average maximum height growth rate (AMHGR) and maximum maximum height growth rate (MMHGR); and/or
  b) a difference of 5% or more in average final diameter (AFD) and maximum final diameter (MFD) and average diameter growth rate (ADGR) and maximum diameter coefficient (MDC); and/or
  c) a difference of 18% or more in average final height (AFH) and/or average final diameter (AFD) and/or average maximum height growth rate (AMHGR) and/or average diameter growth rate (ADGR); and/or
  d) a difference of 18% or more in maximum final height (MFH) and/or maximum final diameter (MFD) and/or maximum maximum height growth rate (MMHGR) and/or maximum diameter coefficient (MDC);
when comparing said group of transgenic plants grown for 8 weeks in a greenhouse under a photoperiod of 18 hours, a temperature of 22° C./15° C. (day/night) and a weekly fertilization Weibulls Rika S NPK 7-1-5 diluted 1 to 100 with a group of wild-type plants grown under identical conditions; wherein the maximum height growth rate is defined as the slope of a linear function fitted over four consecutive height data points, a height growth rate value was calculated for data point 1-4, data point 2-5 etc. in a step-wise manner and a maxim height growth rate value being computed for each plant.

A number of genes analyzed using the novel analytical platform show interesting and most often unexpected commercial features. Thus, another aspect of the invention relates to a transgenic plant comprising a recombinant polynucleotide (DNA construct) comprising a nucleotide sequence capable of altering in the plant the level of a gene product of at least one gene specifically expressed during wood formation phases, wherein the at least one gene is selected for conforming to the criteria that RNAi down-regulation of said gene in a group of 3-8 transgenic plants causes:
  a) a difference of 5% or more in average final height (AFH) and maximum final height (MFH) and average maximum height growth rate (AMHGR) and maximum maximum height growth rate (MMHGR); and/or
  b) a difference of 5% or more in average final diameter (AFD) and maximum final diameter (MFD) and average diameter growth rate (ADGR) and maximum diameter coefficient (MDC); and/or
  c) a difference of 18% or more in average final height (AFH) and/or average final diameter (AFD) and/or average maximum height growth rate (AMHGR) and/or average diameter growth rate (ADGR); and/or
  d) a difference of 18% or more in maximum final height (MFH) and/or maximum final diameter (MFD) and/or maximum maximum height growth rate (MMHGR) and/or maximum diameter coefficient (MDC);
when comparing said group of transgenic plants grown for 8 weeks in a greenhouse under a photoperiod of 18 hours, a temperature of 22° C./15° C. (day/night) and a weekly fertilization with N 84 g/l, P1 2 g/l, K 56 g/l, with a group of wild-type plants grown under identical conditions; wherein the maximum height growth rate is defined by calculating the slope of a linear function fitted over four consecutive height data points, a height growth rate value is calculated for data point 1-4, data point 2-5 etc. in a step-wise manner and the maximum height growth rate value is finally selected from the growth rate values for each plant.

Another aspect of the invention provides a plant cell or plant progeny of a transgenic plant according to the invention and comprising a recombinant polynucleotide.

A further aspect of the invention provides wood produced by a transgenic plant having the characteristics described above.

Still another aspect of the invention provides a DNA construct comprising at least one sequence as described as described above.

Finally, one aspect of the invention provides a plant cell or plant progeny comprising the DNA construct according to the invention.

DETAILED DESCRIPTION OF THE INVENTION

Definitions

Figure 1A:
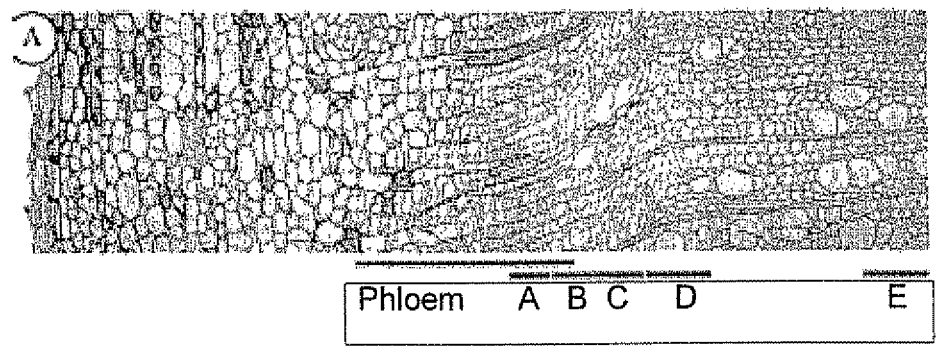
FIG. 1 shows the different phases of wood formation, wherein (A) is a cross section of a hybrid aspen stem stained with Toluidine blue. Black bars indicate the location of the sampled tissues. The phloem sample was included in order to give a low-resolution picture of the gene expression in the other tissue derived from the cambium. (B) is a schematic representation of different cell-types and stages during vascular development. Bars depict timing and extent of the different developmental stages and the appearance of the major cell wall components. (C) shows a hierarchical cluster analysis of 1791 selected genes with differential expression in the sampled tissues. The colour scale at the bottom depicts fold change between samples. (D) (I-X) shows groups of genes with different differential expression patterns, expression ratios in log 2 scale. The samples are indicated at the bottom of the figure.

Prior to discussing the present invention in further details, the following terms and conventions will first be defined:

The term "transgenic plant" refers to a plant that contains genetic material, not found in a wild type plant of the same species, variety or cultivar. The genetic material may include a transgene, an insertional mutagenesis event (such as by transposon or T-DNA insertional mutagenesis), an activation tagging sequence, a mutated sequence, a homologous recombination event or a sequence modified by chimeraplasty. Typically, the foreign genetic material has been introduced into the plant by human manipulation. The term also refers to plants in which genetic material has been inserted to function as a selection marker. Examples of such selectable markers include kanamycin, hygromycin, phosphoinotricin, chlorsulfron, methotrexate, gentamycin, spectinomycin, imidazolinones, d-aminoacids and glyphosate.

In the present context the term "growth" includes primary growth, including a lengthening of the stem and roots, as well as secondary growth of a plant, including production of secondary tissue, "wood", from the cambium and an increase in the girth of stems and roots. Thus, the expression "increased growth" relates in the present context to an increase growth of a transgenic plant relative to the wild-type plant from which the transgenic plant is derived, when grown under the same growth conditions. As described below, a transgenic plant is characterized to have an increased growth if the plant meets at least one of the "growth difference selection criteria" as defined in the below Examples.

The term "phenotype" refers in the present context to an individual plant's total physical appearance, such as growth. Examples of different growth phenotypes used in the present context are listed in the below table 1.2 and comprise e.g. a phenotype named "AFH" which refers to an average final height of the wild type population and each construction group population, or "AFD" average final diameter of the wild type population and each construction group population.

In the context of the present invention the term "phases of wood formation" refers to stages of wood formation, such as cell division and cell expansion, as defined in: Wilson, B. F., Wodzicki, T. J. and Zhaner, R. (1966) Differentiation of cambial derivates: Proposed terminology. Forest Science 12, pp 438-440.

When discussing a gene that is specifically expressed during different phases of wood formation, the term "specifically expressed" is used as a designation of genes the expression of which is increased during wood formation phases. It will be understood that the expression of said genes during phases of wood formation may be increased by 10% or more, such as by 15% or more, 20% or more, 25% or more, 30% or more, 40% or more, 50% or more, 75% or more, 100% or more, 200% or more, 300% or more, 400% or more, 500% or more, 700% or more or 1000% or more.

The term "gene" broadly refers to any segment of DNA associated with a biological function. Genes include coding sequences and/or regulatory sequences required for their expression. Genes also include non-expressed DNA nucleic acid segments that, e.g., form recognition sequences for other proteins (e.g., promoter, enhancer, or other regulatory regions). Genes can be obtained from a variety of sources, including cloning from a source of interest or synthesizing from known or predicted sequence information, and may include sequences designed to have desired parameters.

The term "RNA interference" or "RNAi" refers generally to a process in which a double-stranded RNA molecule or a short hairpin RNA changes the expression of a nucleic acid sequence with which they share substantial or total homology.

The term "RNAi down-regulation" refers to the reduction in the expression of a nucleic acid sequence mediated by one or more RNAi species. The term "RNAi species" refers to a distinct RNA sequence that elicits RNAi.

The term "photoperiod" refers to the daily cycle of light and darkness.

The terms "nucleic acid construct", "DNA construct" and "vector" refer to a genetic sequence used to transform plants or other organisms. The nucleic acid construct or DNA construct may be able to direct, in a transformed plant the expression of a protein or a nucleic acid sequence, such as for example an antisense RNA. Typically, such a nucleic acid construct or DNA construct comprises at least a coding region for a desired gene product or a desired nucleic acid product operably linked to 5' and 3' transcriptional regulatory elements. In some embodiments, such nucleic acid constructs or DNA constructs are chimeric, i.e. consisting of a mixture of sequences from different sources. However, non-chimeric nucleic acid constructs or DNA constructs may also be used in the present invention.

The term "recombinant" when used with reference, e.g., to a cell, nucleotide, vector, protein, or polypeptide typically indicates that the cell, nucleotide, or vector has been modified by the introduction of a heterologous (or foreign) nucleic acid or the alteration of a native nucleic acid, or that the protein or polypeptide has been modified by the introduction of a heterologous amino acid, or that the cell is derived from a cell so modified. Recombinant cells express nucleic acid sequences (e.g., genes) that are not found in the native (non-recombinant) form of the cell or express native nucleic acid sequences (e.g. genes) that would be abnormally expressed under-expressed, or not expressed at all. The term "recombinant" when used with reference to a cell indicates that the cell replicates a heterologous nucleic acid, or expresses a peptide or protein encoded by a heterologous nucleic acid. Recombinant cells can contain genes that are not found within the native (non-recombinant) form of the cell. Recombinant cells can also contain genes found in the native form of the cell wherein the genes are modified and re-introduced into the cell by artificial means. The term also encompasses cells that contain a nucleic acid endogenous to the cell that has been modified without removing the nucleic acid from the cell; such modifications include those obtained by gene replacement, site-specific mutation, and related techniques.

The term "nucleic acid sequence" refers to a polymer of deoxyribonucleotides or ribonucleotides in either single- or double-stranded form. Unless specifically limited, the term encompasses nucleic acid sequences containing known analogues of natural nucleotides which have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences and as well as the sequence explicitly indicated.

A "polynucleotide" is a nucleic acid sequence comprising a plurality of polymerized nucleotide residues, e.g., at least about 15 consecutive polymerized nucleotide residues, optionally at least about 30 consecutive nucleotides, at least about 50 consecutive nucleotides. In many instances, a polynucleotide comprises a nucleotide sequence encoding a polypeptide (or protein) or a domain or fragment thereof. Additionally, the polynucleotide may comprise a promoter, an intron, an enhancer region, a polyadenylation site, a translation initiation site, 5' or 3' untranslated regions, a reporter gene, a selectable marker, or the like. The polynucleotide can be single stranded or double stranded DNA or RNA. The polynucleotide optionally comprises modified bases or a modified backbone. The polynucleotide can be e.g. genomic DNA or RNA, a transcript (such as an mRNA), a cDNA, a PCR product, a cloned DNA, a synthetic DNA or RNA, or the like. The polynucleotide can comprise a sequence in either sense or antisense orientation.

The term "polypeptide" is used broadly to define linear chains of amino acid residues, including occurring in nature and synthetic analogues thereof.

In the context of the present invention "complementary" refers to the capacity for precise pairing between two nucleotides sequences with one another. For example, if a nucleotide at a certain position of an oligonucleotide is capable of hydrogen bonding with a nucleotide at the corresponding position of a DNA or RNA molecule, then the oligonucleotide and the DNA or RNA are considered to be complementary to each other at that position. The DNA or RNA strand are considered complementary to each other when a sufficient number of nucleotides in the oligonucleotide can form hydrogen bonds with corresponding nucleotides in the target DNA or RNA to enable the formation of a stable complex.

In the present context the expressions "complementary sequence" or "complement" therefore also refer to nucleotide sequences which will anneal to a nucleic acid molecule of the invention under stringent conditions.

The term "stringent conditions" refers to general conditions of high, weak or low stringency.

The term "stringency" is well known in the art and is used in reference to the conditions (temperature, ionic strength and the presence of other compounds such as organic solvents) under which nucleic acid hybridisations are conducted. With "high stringency" conditions, nucleic acid base pairing will occur only between nucleic acid fragments that have a high frequency of complementary base sequences, as compared to conditions of "weak" or "low" stringency. Suitable conditions for testing hybridization involve pre-soaking in 5×SSC and pre-hybridizing for 1 hour at ~40° C. in a solution of 20% formamide, 5×Denhardt's solution, 50 mM sodium phosphate, pH 6.8, and 50 mg of denatured sonicated calf thymus DNA, followed by hybridization in the same solution supplemented with 100 mM ATP for 18 hours at ~40° C., followed by three times washing of the filter in 2×SSC, 0.2% SDS at 40° C. for 30 minutes (low stringency), preferred at 50° C. (medium stringency), more preferably at 65° C. (high stringency), even more preferably at ~75° C. (very high stringency). More details about the hybridization method can be found in Sambrook et al., Molecular Cloning: A Laboratory Manual, 2nd Ed., Cold Spring Harbor, 1989.

The terms "hybirdization" and "hybridize" are used broadly to designate the association between complementary and partly complementary nucleic acid sequences, such as in a reversal of the process of denaturation by which they were separated. Hybridization occurs by hydrogen bonding, which may be Watson-Crick, Hoogsteen, reversed Hoogsteen hydrogen bonding, etc., between complementary nucleoside of nucleotide bases. The four nucleobases commonly found in DNA are G, A, T, and C of which G pairs with C, and A pairs with T. In RNA T is replaced with uracil (U), which then pairs with A. The chemical groups in the nucleobases that participate in standard duplex formation constitute the Watson-Crick face. Hoogsteen showed a couple of years later that the purine nucleobases (G and A) in addition to their Watson-Crick face have a Hoogsteen face that can be recognized from the outside of a duplex, and used to bind pyrmidine oligonucleotides via hydrogen bonding, thereby forming a triple helix structure.

A "subsequence" or a "fragment" is any portion of an entire sequence. Thus, a fragment or Subsequence refers to a sequence of amino acids or nucleic acids that comprises a part of A longer sequence of amino acids (e.g. polypeptide) or a nucleic acids (e.g. polynucleotides), Respectively.

In the present context, the homology between two amine acid sewuences or between two Nucleotide sequences is described by the parament "sequence identity".

The term "sequence identity" indicates a quantitative measure of the degree of homology between two amino acid sequences or between two nucleic acid sequences of equal length. If the two sequences to be compared are not of equal length, they must be aligned to give the best possible fit, allowing the insertion of gaps or, alternatively, truncation at the ends of the polypeptide sequences or nucleotide sequences. The sequence identity can be calculated as:

$$\left(\frac{(N_{ref} - N_{dif})100}{N_{ref}}\right)$$

wherein $N_{dif}$ is the total number of non-identical residues in the two sequences when aligned and wherein $N_{ref}$ is the number of residues in one of the sequences. Hence, the DNA sequence AGTCAGTC will have a sequence identity of 75% with the sequence AATCAATC ($N_{dif}$=2 and $N_{ref}$=8). A gap is counted as non-identity of the specific residue(s), i.e. the DNA sequence AGTGTC will have a sequence identity of 75% with the DNA sequence AGTCAGTC ($N_{dif}$=2 and $N_{dif}$=8).

With respect to all embodiments of the invention relating to nucleotide sequences, the percentage of sequence identity between one or more sequences may also be based on alignments using the clustalW software (www.ebi.ac.uk/clustalW/index.html) with default settings. For nucleotide sequence alignments these settings are: Alignment=3Dfull, Gap Open 10.00, Gap Ext. 0.20, Gap separation Dist. 4, DNA weight matrix: identity (IUB). Alternatively, the sequences may be analysed using the program DNASIS Max and the comparison of the sequences may be done at www.paraliqn.org/. This service is based on the two comparison algorithms called Smith-Waterman (SW) and ParAlign. The first algorithm was published by Smith and Waterman (1981) and is a well established method that finds the optimal local alignment of two sequences. The other algorithm, ParAlign, is a heuristic method for sequence alignment; details on the method are published in Rognes (2001). Default settings for score matrix and Gap penalties as well as E-values were used.

The phrase "substantially identical" or "substantial identity" in the context of two nucleic acids or polypeptides, refers to two or more sequences or sub-sequences that have at least about 60%, 70%, 75%, preferably 80% or 85%, more preferably 90%, 91%, 92%, 93%, 94%, 95%, 96%, 97%, 98%, 99%, 99.5%, or greater nucleotide or amino acid residue percent identity, respectively, when compared and aligned for maximum correspondence, as measured using one of the following sequence comparison algorithms or by visual inspection. In certain aspects, the substantial identity exists over a region of amino acid sequences of at least about 50 residues in length, such as, at least about 100, 110, 120, 125, 130, 135, 140, 145, 150, 155, 160, or 165 amino acid residues. In certain aspects, substantial identity exists over a region of nucleic acid sequences of at least about 150 nucleic acid residues, such as at least about 200, 250, 300, 330, 360, 375, 400, 425, 450, 460, 480, 500, 600, 700, 800 such as at least about 900 nucleotides or such as at least about 1 kb, 1.1 kb, 1.2 kb, 1.3 kb, 1.4 kb, 1.5 kb, 1.6 kb, 1.7 kb, 1.8 kb, 1.9 kb, 2 kb, 2.1 kb, 2.2 kb, 2.3 kb, 2.4 kb, 2.5 kb, 2.6 kb, 2.7 kb, 2.8 kb, 2.9 kb or such as at least about 3 kb. In some aspects, the amino acid or nucleic acid sequences are substantially identical over the entire length of the polypeptide sequence or the corresponding coding region.

The term "Conservative substitutions" are within the group of basic amino acids (arginine, lysine and histidine), acidic amino acids (glutamic acid and aspartic acid), polar amino acids (glutamine and asparagine), hydrophobic amino acids (leucine, isoleucine, valine and methionine), aromatic amino acids (phenylalanine, tryptophan and tyrosine), and small amino acids (glycine, alanine, serine and threonine). Amino acid substitutions which do not generally alter the specific activity are known in the art and are described, for example, by H. Neurath and R. L. Hill, 1979, In, The Proteins, Academic Press, New York. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly as well as these in reverse.

The term "conservatively substituted variant" as used herein refers to a variant of a nucleotide sequence comprising one or more conservative substitutions.

Generally and in the present context, the term "silent substitution" refers to a base substitution which does not affect the sense of a codon and thus has no effect on polypeptide structure. As the skilled person will know silent substitutions are possible because of the degeneracy of the genetic code.

The term "conserved domain" refers to a sequence of amino acids in a polypeptide or a sequence of nucleotides in DNA or RNA that is similar across multiple species. A known set of conserved sequences is represented by a consensus sequence. Amino acid motifs are often composed of conserved sequences. Additionally, the term "conserved sequence" refers to a base sequence in a nucleic acid sequence molecule or an amino acid sequence in a protein that has remained essentially unchanged throughout evolution. A "consensus sequence" is defined in terms of an idealized sequence that represents the base most often present at each position in a nucleic acid sequence or the amino acid most often present at each position in a protein. A "consensus sequence" is identified by aligning all known examples of a nucleic acid sequence or a protein so as to maximise their sequence identity. For a sequence to be accepted as a consensus sequence each particular base or amino acid must be reasonably predominant at its position and most of the sequences must be related to the consensus by only few substitutions, such as 1 or 2.

The term "promoter," as used herein, refers to a region of sequence determinants located upstream from the start of transcription of a gene and which are involved in recognition and binding of RNA polymerase and other proteins to initiate and modulate transcription. Promoters useful in plants need not be of plant origin. A "basal promoter" is the minimal sequence necessary for assembly of a transcription complex required for transcription initiation. Basal promoters frequently include a TATA box" element usually located between and 35 nucleotides upstream from the site of initiation of transcription. Basal promoters also sometimes include a CCAAT box" element (typically a sequence CCAAT) and/or a GGGCG sequence, usually located between 40 and 200 nucleotides, preferably 60 to 120 nucleotides, upstream from the start site of transcription.

Promoters referred to herein as "constitutive promoters" actively promote transcription under most, but not necessarily all, environmental conditions and states of development or cell differentiation. Examples of constitutive promoters include the cauliflower mosaic virus (CaMV) 35S transcript initiation region and the 1' or 2' promoter derived from TDNA of *Agrobacterium tumefaciens*, and other transcription initiation regions from various plant genes, such as the maize ubiquitin-1 promoter, known to those of skill. Organ-specific promoters may be, for example, a promoter from storage sink tissues such as seeds, potato tubers, and fruits, or from metabolic sink tissues such as meristems, a seed specific promoter such as the glutelin, prolamin, globulin, or albumin promoter from rice, a *Vicia faba* promoter from the legumin B4 and the unknown seed protein gene from *Vicia faba*, a promoter from a seed oil body protein, the storage protein napA promoter from *Brassica napus*, or any other seed specific promoter known in the art, e.g., as described in WO 91/14772. Furthermore, the promoter may be a leaf specific promoter such as the rbcs promoter from rice or tomato, the *chlorella* virus adenine methyltransferase gene promoter, or the aldP gene promoter from rice, or a wound inducible promoter such as the potato pint promoter.

An "inducible promoter" in the context of the present invention refers to a promoter which is regulated under certain conditions, such as light, chemical concentration, protein concentration, conditions in an organism, cell, or organelle, etc. An example of an inducible promoter is the HSP promoter and the PARSK1, the promoter from the *Arabidopsis* gene encoding a serine-threonine kinase enzyme and which is induced by dehydration, abscissic acid and sodium chloride. In essence, expression under the control of an inducible promoter is "switched on" or increased in response to an applied stimulus. The nature of the stimulus varies between promoters and may include the above environmental factors. Whatever the level of expression is in the absence of the stimulus, expression from any inducible promoter is increased in the presence of the correct stimulus.

As used herein, the term "tissue specific" refers to a characteristic of a particular tissue that is not generally found in all tissues, or may be exclusive found in a tissue of interest. In the present application, "tissue specific" is used in reference to a gene regulatory element (promoter or promoter plus enhancer and/or silencer), the gene it encodes, or the polypeptide product of such a gene. In the context of a gene regulatory element or a "tissue specific promoter", the term means that the promoter (and also other regulatory elements such as enhancer and/or silencer elements) directs the transcription of a linked sequence in a cell of a particular lineage, tissue, or cell type, but is substantially inactive in cells or tissues not of that lineage, tissue, or cell type. A tissue specific promoter useful according to the invention is at least 5-fold, 10-fold, 25-fold, 50fold, 100-fold, 500-fold or even 1,000 times more active in terms of transcript production in the particular tissue than it is in cells of other tissues or in transformed or malignant cells of the same lineage. In the context of a gene or the polypeptide product of a gene, the term tissue specific means that the polypeptide product of the gene is detectable in cells of that particular tissue or cell type, but not substantially detectable in certain other cell types. Particularly relevant tissue specific promoters include promoter sequences specifically expressed or active in the xylem forming tissue in a plant. Examples of such promoters are the Lmp1, Lmx2, Lmx3, Lmx4 and Lmx5 promoters, described in WO2004097024.

A "terminator sequence" refers to a section of genetic sequence that marks the end of gene or operon on genomic DNA for transcription. Terminator sequences are recognized by protein factors that co-transcriptionally cleave the nascent RNA at a polyadenylation signal, halting further elongation of the transcript by RNA polymerase. A nucleic acid is "operably linked" when it is placed into a functional relationship with another nucleic acid sequence. For instance, a promoter or enhancer is operably linked to a coding sequence if it increases the transcription of the coding sequence. Operably linked means that the DNA sequences being linked are typically contiguous and, where necessary to join two protein coding regions, contiguous and in reading frame. However, since enhancers generally function when separated from the promoter by several kilobases and intronic sequences may be of variable lengths, some polynucleotide elements may be operably linked but not contiguous.

In the context of the present invention the terms "transformation" and "transforming" are used interchangeably and as synonyms to "transfecting" and "transfection", respectively, to refer to the process of introducing DNA into a cell. The DNA constructs, including at least a portion of the gene or promoter of interest, can be introduced into host cells, which as stated previously, can be individual cells, cells in culture, cells as part of a host organism, a fertilized oocyte orgametophyte or an embryonic cell. By the term "introduction" when used in reference to a host cell is meant to refer to standard procedures known in the art for introducing recombinant vector DNA into the target host cell. Such procedures include, but are not limited to, transfection, infection, transformation, natural uptake, electroporation, biolistics and *Agrobacterium*.

By "regenerable cell" is meant a plant cell from which a whole plant can be regenerated. It will be understood that the regenerable cell is a cell that has maintained its genetic potential, also known in the art as "totipotency". It will further be understood that the regenerable cells, when grown in culture, may need the appropriate stimuli to express the total genetic potential of the parent plant.

Method of Producing a Transgenic Plant
Functional Analyses for Selection of Genes Candidate genes for use in changing and/or modifying the phenotype of a plant with regard to growth may be identified using prior art procedures, e.g. as described in Hertzberg et al. (2001) and Schrader et al. (2004). Candidate genes involved in regulating growth may also for example be identified among transcription factors with special features identified using prior art knowledge. Such identification of candidate genes is known in the art as being important in order to maximize the positive output of a functional genomics program directed against growth related properties/functions. Accordingly, a first aspect of the present invention provides a method of producing a transgenic plant having an increased growth compared to its wild type, comprising altering in the plant the level of a gene product of at least one gene specifically expressed during wood formation phases.

While based on the targeting of such candidate genes, the present invention provides a method of producing a transgenic plant which includes the targeting of a gene that has been further selected by a novel approach to functional analyses.

According to one embodiment of this aspect, the at least one gene is selected for conforming to the criteria that RNAi down-regulation of said gene in a group of 3-8 transgenic plants causes:
    a) a difference of 5% or more in average final height (AFH) and maximum final height (MFH) and average maximum height growth rate (AMHGR) and maximum maximum height growth rate (MMHGR); and/or
    b) a difference of 5% or more in average final diameter (AFD) and maximum final diameter (MFD) and average diameter growth rate (ADGR) and maximum diameter coefficient (MDC); and/or
    c) a difference of 18% or more in average final height (AFH) and/or average final diameter (AFD) and/or average maximum height growth rate (AMHGR) and/or average diameter growth rate (ADGR); and/or
    d) a difference of 18% or more in maximum final height (MFH) and/or maximum final diameter (MFD) and/or maximum maximum height growth rate (MMHGR) and/or maximum diameter coefficient (MDC);
when comparing said group of transgenic plants grown for 8 weeks in a greenhouse under a photoperiod of 18 hours, a temperature of 22° C./15° C. (day/night) and a weekly fertilization with N 84 g/l, P1 2 g/l, K 56 g/l, with a group of wild-type plants grown under identical conditions; and
wherein the maximum height growth rate is defined by calculating the slope of a linear function fitted over four consecutive height data points, a height growth rate value is calculated for data point 1-4, data point 2-5 etc. in a step-wise manner and the maximum height growth rate value is finally selected from the growth rate values for each plant.

A fertilizer containing 84 gram of N per liter, 2 gram of P1 per liter, and 56 gram of K per liter is currently available under the trade name Weibulls Rika S NPK7-1-5. The composition of this fertilizer is as follows (all in g/p: N tot=84, $NO_3$=55, $NH_4$=29, P=12, K=56, Mg=7.2, S=7.2, B=0.18, Cu=0.02, Fe=0.84, Mn=0.42, Mo=0.03, Zn=0.13.

In a further embodiment a more stringent set of criteria are applied. According to this embodiment the at least one gene is selected for conforming to the criteria that RNAi down-regulation of said gene in a group of 3-8 transgenic plants causes:
    a) a difference of 8% or more in average final height (AFH) and maximum final height (MFH) and average maximum height growth rate (AMHGR) and maximum maximum height growth rate (MMHGR); and/or
    b) a difference of 8% or more in average final diameter (AFD) and maximum final diameter (MFD) and average diameter growth rate (ADGR) and maximum diameter coefficient (MDC); and/or
    c) a difference of 22% or more in average final height (AFH) and/or average final diameter (AFD) and/or average maximum height growth rate (AMHGR) and/or average diameter growth rate (ADGR); and/or
    d) a difference of 22% or more in maximum final height (MFH) and/or maximum final diameter (MFD) and/or maximum maximum height growth rate (MMHGR) and/or maximum diameter coefficient (MDC);
when comparing said group of transgenic plants grown for 8 weeks in a greenhouse under a photoperiod of 18 hours, a temperature of 22° C./15° C. (day/night) and a weekly fertilization with N 84 gill P1 2 g/l, K 56 g/l, with a group of wild-type plants grown under identical conditions;
wherein the maximum height growth rate is defined by calculating the slope of a linear function fitted over four consecutive height data points, a height growth rate value is calculated for data point 1-4, data point 2-5 etc. in a step-wise manner and the maximum height growth rate value is finally selected from the growth rate values for each plant.

An advantage of the present invention is that it provides an extremely sensitive analytical platform for evaluating candidate genes involvement in determining growth characteristics. While gene evaluation methods have previously been based the evaluation of phenotypes according to a single criterion, such as plant height or diameter, the present method allows a phenotype to be characterised on the basis of multiple criteria, including average final height, maximum final height, average maximum height growth rare, and maximum of maximum height growth rate. Use of this analytical platform allows the identification and selection of new target genes to be used in methods for generating plants having increased growth using. Using a more simple approach these target genes would not have been considered to be involved determination of growth characteristics or they would only have been considered to play a marginal role in generating the growth phenotype.

In specific embodiments of the invention advantageous plant phenotypes are generated by modifying, relative to the corresponding wild-type plant, the expression level of candidate genes that have been evaluated and selected according to the above criteria. According to these aspects a method is provided which comprises altering in the plant the level of a gene product of at least one gene comprising a nucleotide sequence selected from the group consisting of:

a) a nucleotide sequence from SEQ ID NO:1-17, 50, 51, 54-58, 60; such as SEQ ID NO: 1, 2, 5, 6, 10, 13, 15, 16, 17, 50, 51, 54, 55, 56, 57, 58, 60;

b) a nucleotide sequence being at least 60% identical to a nucleotide sequence from SEQ ID NO:1-17, 50, 51, 54-58, 60; such as SEQ ID NO: 1, 2, 5, 6, 10, 13, 15, 16, 17, 50, 51, 54, 55, 56, 57, 58, 60.

c) a subsequence or fragment of a nucleotide sequence of a) or b).

The sequences specified by sequence ID numbers 1-17, 50, 51, 54-58, 60; such as SEQ ID NO: 1, 2, 5, 6, 10, 13, 15, 16, 17, 50, 51, 54, 55, 56, 57, 58, 60. represent partial sequences of the candidate genes as cloned from hybrid aspen. As the skilled person will understand, additional sequence from these genes 5' as well as 3' to the sequence described in SEQ ID NOs:1-17, 50, 51, 54-58, 60; such as SEQ ID NO: 1, 2, 5, 6, 10, 13, 15, 16, 17, 50, 51, 54, 55, 56, 57, 58, 60.

is readily achievable using conventional cloning techniques, such as those described in Sambrook et al.

Nucleic Acid Constructs

According to more particular embodiments of the invention, the method comprises the step of providing a nucleic acid construct, such as a recombinant DNA construct, comprising a nucleotide sequence selected from the group consisting of:

d) a nucleotide sequence comprising a sequence selected from SEQ ID NO: SEQ ID NO:1-17, 50, 51, 54-58, 60; such as SEQ ID NO: 1, 2, 5, 6, 10, 13, 15, 16, 17, 50, 51, 54, 55, 56, 57, 58, 60, e) a complementary nucleotide sequence of a nucleotide sequence of d);

f) a sub-sequence or fragment of a nucleotide sequence of d) or e);

g) a nucleic acid sequence being at least 60% identical to any one of the sequences in d), e) and f); and h) a nucleotide sequence which hybridizes under stringent conditions to a nucleotide sequence of d), e) or f).

In further embodiments of the invention the nucleic acid sequence in c) or g) is at least 65% identical to any one of the sequences in a), c), d), e) or f), such as at least 70% identical, at least 75% identical, at least 80% identical, at least 85% identical, at least 87% identical, at least 90% identical, at least 95% identical, at least 97% identical, at least 98% identical, at least 99% identical, or at least 99.5% identical to any one of the sequences in a), c), d), e) or f).

In preferred embodiments of this aspect of the invention the nucleotide sequence of a) is selected from the group consisting of SEQ ID NOs: 1, 5, 6, 9, 11, 12, 15, 17, 56, 57 and 58.

A variety of methods exist in the art for producing the nucleic acid sequences and nucleic acid/DNA constructs of the invention. Procedures for identifying and isolating DNA clones are well known to those of skill in the art, and are described in, e.g. Sambrook et al., Molecular Cloning-A Laboratory Manual (2nd Ed.), Vol. 1-3, Cold Spring Harbor Laboratory, Cold Spring Harbor, N.Y., 1989. Alternatively, the nucleic acid sequences of the invention can be produced by a variety of in vitro amplification methods adapted to the present invention by appropriate selection of specific or degenerate primers. Examples of protocols sufficient to direct persons of skill through in vitro amplification methods, including the polymerase chain reaction (PCR) the ligase chain reaction (LCR), Qbeta-replicase amplification and other RNA polymerase mediated techniques (e.g., NASBA), e.g., for the production of the homologous nucleic acids of the invention are found in Sambrook, supra.

Alternatively, nucleic acid constructs of the invention can be assembled from fragments produced by solid-phase synthesis methods. Typically, fragments of up to approximately 100 bases are individually synthesized and then enzymatically or chemically ligated to produce a desired sequence, e.g., a polynucletotide encoding all or part of a transcription factor. For example, chemical synthesis using the phosphoramidite method is well known to the skilled person. According to such methods, oligonucleotides are synthesized, purified, annealed to their complementary strand, ligated and then optionally cloned into suitable vectors.

As mentioned, the above described sequences are from hybrid aspen. As the skilled person will understand, homologues of the described sequences may be isolated from other species, non-limiting examples of which include acacia, eucalyptus, hornbeam, beech, mahogany, walnut, oak, ash, hickory, birch, chestnut, alder, maple, sycamore, ginkgo, palm tree, sweet gum, cypress, Douglas fir, fir, *sequoia*, hemlock, cedar, juniper, larch, pine, redwood, spruce and yew, apple, plum, pear, banana, orange, kiwi, lemon, cherry, grapevine, fig, cotton, bamboo, switch grass, red canary grass and rubber plants. Useful homologues of the described sequences may also be isolated from hardwood plants from the Salicaceae family, e.g. from the *salix* and *populus* genus. Members of this genius are known by their common names: willow, poplar and aspen.

In particular, the nucleotide sequence according to the invention comprises a sequence selected from those of SEQ ID NOs: 18-38, 48, 49, 51-60; such as SEQ ID NO: 20, 29, 36, 37, 38, 48, 49, 51-60 or a complementary nucleotide sequence thereof.

It will be apparent that the sub-sequences or fragment in c) or f) as described above comprises at least 15 nucleotides, such as at least 16 nucleotides, at least 17 nucleotides, at least 18 nucleotides, at least 19 nucleotides, at least 20 nucleotides, at least 21 nucleotides, at least 22 nucleotides, at least 23 nucleotides, at least 24 nucleotides, at least 25 nucleotides, e.g. at least 30 nucleotides, at least 35 nucleotides, at least 40 nucleotides, at least 45 nucleotides, at least 50 nucleotides, at least 55 nucleotides, at least 60 nucleotides, at least 65 nucleotides, at least 70 nucleotides, at least 75 nucleotides, at least 80 nucleotides, at least 85 nucleotides, at least 90 nucleotides, at least 95 nucleotides, or such as at least 100 nucleotides. In certain embodiments, the sub-sequences or fragment in c) or f) as described above comprises at least about 150 nucleic acid residues, such as at least about 200, 250, 300, 330, 360, 375, 400, 425, 450, 460, 480, 500, 600, 700, 800 such as at least about 900 nucleotides or such as at least about 1 kb, 1.1 kb, 1.2 kb, 1.3 kb, 1.4 kb, 1.5 kb, 1.6 kb, 1.7 kb, 1.8 kb, 1.9 kb, 2 kb, 2.1 kb, 2.2 kb, 2.3 kb, 2.4 kb, 2.5 kb, 2.6 kb, 2.7 kb, 2.8 kb, 2.9 kb or such as at least about 3 kb.

In particular, the method according to the present invention may comprise a step of providing a nucleic acid construct, such as a recombinant DNA construct, comprising a nucleotide sequence which relative to the particular sequences described, comprises conservative variations altering only one, or a few amino acids in the encoded polypeptide may also be provided and used according to the present invention. Accordingly, it is within the scope of the invention to provide and use a recombinant DNA construct comprising a nucleotide sequence which encodes a polypeptide comprising a conservatively substituted variant of a polypeptide of a).

Sequence alterations that do not change the amino acid sequence encoded by the polynucleotide are termed "silent" substitutions. With the exception of the codons ATG and TGG, encoding methionine and tryptophan, respectively, any of the possible codons for the same amino acid can be substituted by a variety of techniques, e.g., site-directed mutagenesis, available in the art. Accordingly, the present invention may also provide a recombinant nucleic acid construct, wherein the nucleotide sequence comprises a silent substitution in a nucleotide sequence.

In certain further embodiments of the invention, the subsequences or fragments have at least 65% sequence identity to a conserved domain of a nucleotide sequence as described above under item a) or d), such as at least 70% identical, at least 75% identical, at least 80% identical, at least 85% identical, at least 87% identical, at least 90% identical, at least 95% identical, at least 97% identical, at least 98% identical, at least 99% identical, or at least 99.5% identical to a conserved domain of a nucleotide sequence as described above under item a) or d).

Approaches to Obtaining Altering the Level of a Gene Product

This invention is used by lowering or in some instances abolishing the expression of certain genes, non limiting examples how this can be done are presented here. The nucleic acid construct or recombinant DNA construct as described above may be used for the identification of plants having altered growth characteristics as compared to the wild-type. Such plants may for instance be naturally occurring variants or plants that have been modified genetically to exhibit altered growth properties. For such purposes the nucleic acid construct or recombinant DNA construct according to the invention may be used e.g. as a probe in conventional hybridization assays or as a primer for specific amplification of nucleic acid fragments.

Although the main part of this invention is how a down regulation of the gene products gives the desired effect. It also shows that changing the expression of the genes presented here can be used to modify the desired properties, this is another way to look at the data, and an effect of this view is that also increasing the gene products within the plant is a way to modify the desired trait. There are different ways to increase the levels of a gene product, these are described below in parallel with the ways to down regulate a gene product below.

These genes could also be used as targets for marker assisted breeding because changes in the gene regulatory sequences can give changes in the expression patterns and changes in the coding sequences can give changes in the gene function, and we know that manipulating these genes gives changes in the desired traits.

In addition, the nucleic acid construct or recombinant DNA construct according to the invention may be used for the purpose of gene replacement in order to modify the respective plant growth phenotype.

Suppression of endogenous gene expression can for instance be achieved using a ribozyme. Ribozymes are RNA molecules that possess highly specific endoribonuclease activity. The production and use of ribozymes are disclosed in U.S. Pat. No. 4,987,071 and U.S. Pat. No. 5,543,508. While antisense techniques are discussed below, it should be mentioned that synthetic ribozyme sequences including antisense RNAs can be used to confer RNA cleaving activity on the antisense RNA, such that endogenous mRNA molecules that hybridize to the antisense RNA are cleaved, which in turn leads to an enhanced antisense inhibition of endogenous gene expression.

Vectors in which RNA encoded by a relevant gene homologue is over-expressed can also be used to obtain co-suppression of a corresponding endogenous gene, e.g., in the manner described in U.S. Pat. No. 5,231,020 to Jorgensen. Such co-suppression (also termed sense suppression) does not require that the entire gene sequence be introduced into the plant cells, nor does it require that the introduced sequence be exactly identical to the endogenous sequence of interest. However, the suppressive efficiency will be enhanced as specificity of hybridization is increased, e.g., as the introduced sequence is lengthened, and/or as the sequence similarity between the introduced sequence and the endogenous transcription factor gene is increased.

Vectors expressing an untranslatable form of gene, e.g., sequences comprising one or more stop codons, or nonsense mutation, can also be used to suppress expression of an endogenous transcription factor, thereby reducing or eliminating its activity and modifying one or more traits. Methods for producing such constructs are described in U.S. Pat. No. 5,583,021. In particular, such constructs can be made by introducing a premature stop codon into the gene.

One way of performing targeted DNA insertion is by use of the retrovirus DNA integration machinery as described in WO2006/078431. This technology is based on the possibility of altering the integration site specificity of retroviruses and retrotransposons integrase by operatively coupling the integrase to a DNA-binding protein (tethering protein). Engineering of the integrase is preferably carried out on the nucleic acid level, via modification of the wild type coding sequence of the integrase by PCR. The integrase complex may thus be directed to a desired portion or be directed away from an undesired portion of genomic DNA thereby producing a desired integration site characteristic.

Another such technology is the "Targeting Induced Local Lesions in Genomes", which is a non-transgenic way to alter gene function in a targeted way. This approach involves mutating a plant with foe example ethyl methanesulfonate (EMS) and later locating the individuals in which a particular desired gene has been modified. The technology is described for instance in Slade and Knauf, Transgenic Res. 2005 April; 14(2):109-15 and Henikoff, Till and Comai, Plant Physiol. 2004 June; 135(2):630-6.

Another method for abolishing the expression of a gene is by insertion mutagenesis using the T-DNA of *Agrobacterium tumefaciens*. After generating the insertion mutants, the mutants can be screened to identify those containing the insertion in an appropriate gene. Plants containing a single transgene insertion event at the desired gene can be crossed to generate homozygous plants for the mutation.

As will be apparent to the skilled person, a plant trait can also be modified by using the cre-lox system. A plant genome can be modified to include first and second lox sites that are then contacted with a Cre recombinase. Provided that the lox sites are in the same orientation, the intervening DNA sequence between the two sites will be excised. If the lox sites are in the opposite orientation, the intervening sequence is inverted.

The polynucleotides and polypeptides of this invention can also be expressed in a plant in the absence of an expression cassette by manipulating the activity or expression level of the endogenous gene by other means, for example, by ectopically expressing a gene by T-DNA activation tagging (Ichikawa et al. (1997) Nature 390 698-701; Kakimoto et al. (1996) Science 274: 982-985). This method entails transforming a plant with a gene tag containing multiple transcriptional enhancers and once the tag has inserted into the genome, expression of a flanking gene coding sequence becomes deregulated. In another example, the transcriptional machinery in a plant can be modified so as to increase transcription levels of a polynucleotide of the invention (See, e.g., PCT Publications WO 96/06166 and WO 98/53057 which describe the modification of the DNA binding specificity of zinc finger proteins by changing particular amino acids in the DNA binding motif).

Antisense Suppression of Expression

However, the recombinant DNA construct, comprising a nucleotide sequence as described above is particularly useful for sense and anti-sense suppression of expression, e.g., to down-regulate expression of a particular gene, in order to obtain a plant phenotype with increased growth. That is, the nucleotide sequence of the invention, or sub-sequences or anti-sense sequences thereof, can be used to block expression of naturally occurring homologous nucleic acids. Varieties of traditional sense and antisense technologies are known in the art, e.g., as set forth in Lichtenstein and Nellen (1997), Antisense Technology: A Practical Approach IRL Press at Oxford University, Oxford, England. The objective of the antisense approach is to use a sequence complementary to the target gene to block its expression and create a mutant cell line or organism in which the level of a single chosen protein is selectively reduced or abolished.

For example, a reduction or elimination of expression (i.e., a "knock-out") of a gene product in a transgenic plant in order to produce a plant phenotype characterised by increased growth can be obtained by introducing an antisense construct corresponding to the polypeptide of interest as a cDNA. For antisense suppression, a cDNA encoding the gene product or part thereof is arranged in reverse orientation (with respect to the coding sequence) relative to the promoter sequence in the expression vector. The introduced sequence need not be the full length cDNA or gene, and need not be identical to the cDNA or gene found in the plant type to be transformed. Typically, the antisense sequence need only be capable of hybridizing to the target gene or RNA of interest. Thus, where the introduced sequence is of shorter length, a higher degree of homology to the endogenous transcription factor sequence will be needed for effective antisense suppression. While antisense sequences of various lengths can be utilized, preferably, the introduced antisense sequence in the vector will range from 15-30 nucleotides in length, such as from 16-28 nucleotides, from 17-26 nucleotides or from 18-24 nucleotides in length, and improved antisense suppression will typically be observed as the length of the antisense sequence increases. Preferably, the length of the antisense sequence in the vector will be greater than 100 nucleotides. Transcription of an antisense construct as described results in the production of RNA molecules that are the reverse complement of mRNA molecules transcribed from the endogenous gene in the plant cell.

For more elaborate descriptions of anti-sense regulation of gene expression as applied in plant cells reference is made to U.S. Pat. No. 5,107,065, the content of which is incorporated herein in its entirety.

RNA Interference

Gene silencing that is induced by double-stranded RNA is commonly called RNA interference or RNAi. RNA interference is a molecular mechanism in which fragments of double-stranded ribonucleic acid (dsRNA) interfere with the expression of a particular gene that shares a homologous sequence with the dsRNA. The process that is mediated by the same cellular machinery that processes microRNA, known as the RNA-induced silencing complex (RISC). The process is initiated by the ribonuclease protein Dicer, which binds and cleaves exogenous double-stranded RNA molecules to produce double-stranded fragments of 20-25 base pairs with a few unpaired overhang bases on each end. The short double-stranded fragments produced by Dicer, called small interfering RNAs (siRNAs), are separated and integrated into the active RISC complex. If one part of an RNA transcript is targeted by an RNAi molecule or construct, the whole transcript is down-regulated.

The catalytically active components of the RISC complex are known in animals as argonaute proteins, endonucleases which mediate the siRNA-induced cleavage of the target mRNA strand. Because the fragments produced by Dicer are double-stranded, they could each in theory produce a functional siRNA; however, only one of the two strands—known as the guide strand—binds the argonaute protein and leads to gene silencing. The other anti-guide strand or passenger strand is degraded as a RISC substrate during the process of RISC activation. The strand selected as the guide tends to be the strand whose 5' end is more stable, but strand selection is not dependent on the direction in which Dicer cleaves the dsRNA before RISC incorporation.

RNA interference as used in the laboratory often involves perfectly base-paired dsRNA molecules that induce mRNA cleavage. After integration into the RISC, siRNAs base pair to their target mRNA and induce the RISC component protein argonaute to cleave the mRNA, thereby preventing it from being used as a translation template. To be stable in vitro or in vivo the sequence of a siLNA or siRNA compound need not be 100% complementary to its target nucleic acid. The fact that the siRNA compounds (and the siLNA compounds as described below) are complementary and specifically hybridisable to their target molecules simply imply that the siRNA (or siLNA) compounds bind sufficiently strong and specific to the target molecule to provide the desired interference with the normal function of the target whilst leaving the function of non-target mRNAs unaffected.

It is known that LNA monomers incorporated into oligos will induce RNA like structure of the oligo and of the hybrid that it may form. It is also shown that LNA residues will direct that structure to DNA residues incorporated towards the 3'-end of the LNA incorporation and to a lesser extend towards the 5'-end. The consequence of this is that it is possible to modify RNA strands with DNA monomers and if one or more LNA residues flank the DNA monomers they too will attain RNA structure. Therefore, DNA and LNA can replace RNA monomers and despite of that the oligo will attain an overall RNA like structure. DNA is much cheaper, easier to synthesize and more nuclease stable than RNA and such modification will therefore improve the overall use and applicability of siRNA's.

Organisms vary in their cells' ability to take up foreign dsRNA and use it in the RNAi pathway. In plants, however, the gene silencing caused by RNAi can spread from cell to cell in plants, and the effects of RNA interference are thus both systemic and heritable in plants For more elaborate descriptions of RNAi gene suppression in plants by transcription of a dsRNA reference is made to U.S. Pat. No. 6,506,559, US Patent Application Publication No. 2002/0168707 A1, and U.S. patent application Ser. No. 09/423,143 (see WO 98/53083), Ser. No. 09/127,735 (see WO 99/53050) and Ser. No. 09/084,942 (see WO 99/61631), all of which are incorporated herein by reference in their entirety.

In the particular embodiments by which the present invention is exemplified the sub-sequences or fragments in c) comprise the sequences of SEQ ID NOs:18-38, 48, 49, 51-60; such as SEQ ID NO: 20, 29, 36, 37, 38, 48, 49, 51-60.

Construction of Vectors

In general, those skilled in the art are well able to construct vectors of the present invention and design protocols for recombinant gene expression. For further details on general protocols for preparation of vectors reference is made to: Molecular Cloning: a Laboratory Manual: 2nd edition, Sambrook et al, 1989, Cold Spring Harbor Laboratory Press. The promoter used for the antisense gene may influence the level, timing, tissue, specificity, or inducibility of the antisense inhibition. Furthermore, antisense can manipulate its specificity by selecting either unique regions of the target gene or regions where it shares homology to other related genes.

Generally, suppression of a gene by RNA interference can be achieved using a recombinant DNA construct having a promoter operably linked to a DNA element comprising a sense and anti-sense element of a segment of genomic DNA or cDNA of the gene, e.g., a segment of at least about 25 nucleotides, such as at least 30, at least 40, at least 50, at least 75, at least 100, at least 200, at least 300, at least 400, at least 500, or at least 750 nucleotides, or such as at least 1 kb, such as at least 1.5 kb, at least 2 kb, at least 2.5 kb, os such as at least 3 kb, where the sense and anti-sense DNA components can be directly linked or joined by an intron or artificial DNA segment that can form a loop when the transcribed RNA hybridizes to form a hairpin structure.

In pertinent embodiments of the invention the nucleic acid construct, or recombinant DNA construct, further comprising a constitutive, inducible, or tissue specific promoter operably linked to said nucleotide sequence.

An example of nucleic acid construct, or recombinant DNA construct has a promoter driving the transcription of a DNA fragment from a target gene followed of an shorter sequence that are present in an inverted repeat, this together triggering the RNAi response of the target gene. Such a construct has been described by Brummel D. A. et al. Plant Journal 2003, 33, pages 793-800).

In another example, an artificial microRNA is constructed were a promoter drives the expression of an RNA molecule mimicking the function of an microRNA and the sequence setting the gene specificity is recominantly introduced. (se Niu et al, 2006. Expression of artificial microRNAs in transgenic *Arabidopsis thaliana* confers virus resistance. Science 2006, vol 24, No. 11 pp 1420-1428) The microRNA can be of natural occurrence and only overexpressed.

In a particular embodiment of the present invention the nucleic acid construct, or recombinant DNA construct, further comprises a strong constitutive promoter in front of a transcribed cassette consisting of part of the target gene followed by a plant functional intron followed by the same part of the target gene in reverse orientation, the transcribed cassette is followed by an terminator sequence. The preferred vector is of such type with one of the nucleotide sequence of the invention is inserted in inverted repeat orientation.

In a presently preferred embodiment of the invention, the nucleic acid construct, or recombinant DNA construct, comprises the sequence of SEQ ID NO: 47.

The presently preferred nucleic acid construct for RNAi based approaches is a vector termed pK7GWIWG2(I). The vector is described in: Gateway vectors for *Agrobacterium*—mediated plants transformation, Karimi, M. et al., Trends In plant Sciences, Vol 7 no 5 pp 193-195. The same basic kind of vector were earlier described in Wesley S. V. et al., Construct design for efficient, effective and high-throughput gene silencing in plants. Plant Journal 2001, 27, pages 581-590.

A person trained in the art will understand that any sequence being part of the genes, or the corresponding mRNA's presented here can be used to down regulate the levels of such mRNA. In the case the presented sequence does not represent the full mRNA, the full mRNA can be cloned with various techniques known to a person skilled in the arts, such as the techniques described in Sambrook et al. A recent resource important for finding more sequences associated with the mRNA transcripts of a *populus* genes is the published genome of *Populus tricocarpa* and the resources described in Tuskan et al 2006 (G. A Tuskan et al, 2006. The genome of Black Cottonwood, *Populus tricocarpa* (Torr. & Gray). Science vol 313 No. 5793, pages 1596-1604.

Transformation of Plant Cells

In accordance with the present invention, the method comprise the further step of transforming regenerable cells of a plant with said nucleic acid construct or recombinant DNA construct and regenerating a transgenic plant from said transformed cell. When introducing the above DNA construct or vector into a plant cell, certain considerations must be taken into account, well known to those skilled in the art. The nucleic acid to be inserted should be assembled within a construct that contains effective regulatory elements that will drive transcription, as described above. There must be available a method of transporting the construct into the cell. Once the construct is within the cell, integration into the endogenous chromosomal material either will or will not occur.

Transformation techniques, well known to those skilled in the art, may be used to introduce the DNA constructs and vectors into plant cells to produce transgenic plants, in particular transgenic trees, with improved plant growth.

A person of skills in the art will realise that a wide variety of host cells may be employed as recipients for the DNA constructs and vectors according to the invention. Non-limiting examples of host cells include cells in embryonic tissue, callus tissue type I, II, and III, hypocotyls, meristem, root tissue, tissues for expression in phloem.

As listed above, *Agrobacterium* transformation is one method widely used by those skilled in the art to transform tree species, in particular hardwood species such as poplar. Production of stable, fertile transgenic plants is now a routine in the art. Other methods, such as microprojectile or particle bombardment, electroporation, microinjection, direct DNA uptake, liposome mediated DNA uptake, or the vortexing method may be used where *Agrobacterium* transformation is inefficient or ineffective, for example in some gymnosperm species.

Alternatively, a combination of different techniques may be employed to enhance the efficiency of the transformation process, e.g. bombardment with *Agrobacterium* coated microparticles or microprojectile bombardment to induce wounding followed by co-cultivation with *Agrobacterium*.

It will be understood, that the particular choice of a transformation technology will be determined by its efficiency to transform certain plant species as well as the experience and preference of the person practising the invention with a particular methodology of choice. It will be apparent to the skilled person that the particular choice of a transformation system to introduce nucleic acid into plant cells is not essential to or a limitation of the invention, nor is the choice of technique for plant regeneration.

Following transformation, transgenic plants are preferably selected using a dominant selectable marker incorporated into the transformation vector. Typically, such a marker will confer antibiotic or herbicide resistance on the transformed plants, and selection of transformants can be accomplished by exposing the plants to appropriate concentrations of the antibiotic or herbicide. A novel selection marker using the D-form of amino acids and based on the fact that plants can only tolerate the L-form offers a fast, efficient and environmentally friendly selection system. An interesting feature of this selection system is that it enables both selection and counter-selection.

Subsequently, a plant may be regenerated, e.g. from single cells, callus tissue or leaf discs, as is standard in the art. Almost any plant can be entirely regenerated from cells, tissues and organs of the plant. Available techniques are reviewed in Vasil et al. 1984, Cell Culture and Somatic Cell Genetics of Plants, Vol I, II and III, Laboratory Procedures.

After transformed plants are selected and grown to maturity, those plants showing an increase growth phenotype are identified. Additionally, to confirm that the phenotype is due to changes in expression levels or activity of the polypeptide or polynucleotide disclosed herein can be determined by analyzing mRNA expression using Northern blots, RT-PCR or microarrays, or protein expression using immunoblots or Western blots or gel shift assays.

Plant Species

In accordance with the invention, the present method produces a transgenic plant having an increased growth compared to its wild type plant from which it is derived. In an embodiment of the present method, the transgenic plant is a perennial plant, i.e. a plant that lives for more than two years. In a specific embodiment, the perennial plant is a woody plant which may be defined as a vascular plant that has a stem (or more than one stem) which is lignified to a high degree.

In a preferred embodiment, the woody plant is a hardwood plant, i.e. broad-leaved or angiosperm trees, which may be selected from the group consisting of acacia, eucalyptus, hornbeam, beech, mahogany, walnut, oak, ash, willow, hickory, birch, chestnut, poplar, alder, maple, sycamore, ginkgo, palm tree and sweet gum. Hardwood plants from the Salicaceae family, such as willow, poplar and aspen, including variants thereof, are of particular interest, as these two groups include fast-growing species of tree or woody shrub which are grown specifically to provide timber and bio-fuel for heating. Cellulosic grasses used for bioenergy like Switch grass and Red Canary Grass are also interesting.

In further embodiments, the woody plant is softwood or a conifer which may be selected from the group consisting of cypress, Douglas fir, fir, *sequoia*, hemlock, cedar, juniper, larch, pine, redwood, spruce and yew.

In useful embodiments, the woody plant is a fruit bearing plant which may be selected from the group consisting of apple, plum, pear, banana, orange, kiwi, lemon, cherry, grapevine and FIG.

Other woody plants which may be useful in the present method may also be selected from the group consisting of cotton, bamboo and rubber plants.

DNA Construct

According to a second main aspect of the invention a DNA construct, such as a recombinant DNA construct, is provided comprising at least one sequence as described above. In particular, the recombinant DNA construct may comprise a nucleotide sequence selected from the group consisting of:

a) a nucleotide sequence comprising a sequence selected from SEQ ID NO:1-17, 50, 51, 54-58, 60; such as SEQ ID NO: 1, 2, 5, 6, 10, 13, 15, 16, 17, 50, 51, 54, 55, 56, 57, 58, 60, b) a complementary nucleotide sequence of a nucleotide sequence of a);

c) a sub-sequence or fragment of a nucleotide sequence of a) or b);

d) a nucleic acid sequence being at least 60% identical to any one of the sequences in a), b) and c); and e) a nucleotide sequence which hybridizes under stringent conditions to a nucleotide sequence of a), b) or c).

In selected embodiments of the invention the nucleic acid sequence in d) is at least 65% identical to any one of the sequences in a), b) and c), such as at least 70% identical, at least 75% identical, at least 80% identical, at least 85% identical, at least 87% identical, at least 90% identical, at least 95% identical, at least 97% identical, at least 98% identical, at least 99% identical, or at least 99.5% identical to any one of the sequences in a), b) and c).

In further embodiments relating to this aspect of the invention the nucleotide sequence comprises a sequence selected from those of SEQ ID NOs:18-38, 48, 49, 51-60; such as SEQ ID NO: 20, 29, 36, 37, 38, 48, 49, 51-60 or a complementary nucleotide sequence thereof.

Also in relation to this aspect of the invention it will be apparent that the sub-sequences or fragment in c) as described above comprises at least 15 nucleotides, such as at least 16 nucleotides, at least 17 nucleotides, at least 18 nucleotides, at least 19 nucleotides, at least 20 nucleotides, at least 21 nucleotides, at least 22 nucleotides, at least 23 nucleotides, at least 24 nucleotides, at least 25 nucleotides, e.g. at least 30 nucleotides, at least 35 nucleotides, at least 40 nucleotides, at least 45 nucleotides, at least 50 nucleotides, at least 55 nucleotides, at least 60 nucleotides, at least 65 nucleotides, at least 70 nucleotides, at least 75 nucleotides, at least 80 nucleotides, at least 85 nucleotides, at least 90 nucleotides, at least 95 nucleotides, or such as at least 100 nucleotides. In certain embodiments, the sub-sequences or fragment in c) as described above comprises at least about 150 nucleic acid residues, such as at least about 200, 250, 300, 330, 360, 375, 400, 425, 450, 460, 480, 500, 600, 700, 800 such as at least about 900 nucleotides or such as at least about 1 kb, 1.1 kb, 1.2 kb, 1.3 kb, 1.4 kb, 1.5 kb, 1.6 kb, 1.7 kb, 1.8 kb, 1.9 kb, 2 kb, 2.1 kb, 2.2 kb, 2.3 kb, 2.4 kb, 2.5 kb, 2.6 kb, 2.7 kb, 2.8 kb, 2.9 kb or such as at least about 3 kb.

Also, in accordance with the discussion above, the nucleotide sequence encodes a polypeptide comprising a conservatively substituted variant of a polypeptide of (a). Further, the nucleotide sequence comprises a silent substitution in a nucleotide sequence. In additional embodiments of the pertaining to this aspect of the invention, the sub-sequences or fragments have at least 65% sequence identity to a conserved domain of a nucleotide sequence as described above under item a). such as at least 70% identical, at least 75% identical, at least 80% identical, at least 85% identical, at least 87% identical, at least 90% identical, at least 95% identical, at least 97% identical, at least 98% identical, at least 99% identical, or at least 99.5% identical to a conserved domain of a nucleotide sequence as described above under item a).

In particular embodiments, the sub-sequences or fragments in c) comprises the sequences of SEQ ID NOs: 18-38, 48, 49, 51-60; such as SEQ ID NO: 20, 29, 36, 37, 38, 48, 49, 51-60.

In further embodiments and in accordance with the description above, the recombinant DNA construct further comprising a constitutive, inducible, or tissue specific promoter operably linked to said nucleotide sequence. In particular, the recombinant DNA construct may further comprise a strong constitutive promoter in front of a transcribed cassette consisting of part of the target gene followed by a plant functional intron followed by the same part of the target gene in reverse orientation as described above. Another preferred type of recombinant DNA construct has a promoter driving the transcription of a DNA fragment from a target gene followed of an shorter sequence that are present in an inverted repeat, as also explained above.

In the presently exemplified embodiments of the invention the recombinant DNA construct comprises the sequence of SEQ ID NO: 47.

Transgenic Plants

A third aspect of the invention provides a transgenic plant comprising a recombinant polynucleotide (DNA construct) comprising a nucleotide sequence capable of altering in the plant the level of a gene product of at least one gene specifically expressed during wood formation phases. By analogy to the description above it will be understood that in one embodiment the at least one gene is selected for conforming to the criteria that RNAi down-regulation of said gene in a group of 3-8 transgenic plants causes:
  a) a difference of 5% or more in average final height (AFH) and maximum final height (MFH) and average maximum height growth rate (AMHGR) and maximum maximum height growth rate (MMHGR); and/or
  b) a difference of 5% or more in average final diameter (AFD) and maximum final diameter (MFD) and average diameter growth rate (ADGR) and maximum diameter coefficient (MDC); and/or
  c) a difference of 18% or more in average final height (AFH) and/or average final diameter (AFD) and/or average maximum height growth rate (AMHGR) and/or average diameter growth rate (ADGR); and/or
  d) a difference of 18% or more in maximum final height (MFH) and/or maximum final diameter (MFD) and/or maximum maximum height growth rate (MMHGR) and/or maximum diameter coefficient (MDC);
when comparing said group of transgenic plants grown for 8 weeks in a greenhouse under a photoperiod of 18 hours, a temperature of 22° C./15° C. (day/night) and a weekly fertilization with N 84 g/l, PI 2 g/l, K 56 g/l, with a group of wild-type plants grown under identical conditions;
wherein the maximum height growth rate is defined by calculating the slope of a linear function fitted over four consecutive height data points, a height growth rate value is calculated for data point 1-4, data point 2-5 etc. in a step-wise manner and the maximum height growth rate value is finally selected from the growth rate values for each plant.

According to a further embodiment of this aspect of the invention, the gene expressed during the wood formation phases is selected for conforming to the criteria that RNAi down-regulation of the gene in a group of 3-8 transgenic plants causes:
  a) a difference of 8% or more in average final height (AFH) and maximum final height (MFH) and average maximum height growth rate (AMHGR) and maximum height growth rate (MMHGR); and/or
  b) a difference of 8% or more in average final diameter (AFD) and maximum final diameter (MFD) and average diameter growth rate (ADGR) and maximum diameter coefficient (MDC); and/or
  c) a difference of 22% or more in average final height (AFH) and/or average final diameter (AFD) and/or average maximum height growth rate (AMHGR) and/or average diameter growth rate (ADGR); and/or
  d) a difference of 22% or more in maximum final height (MFH) and/or maximum final diameter (MFD) and/or maximum maximum height growth rate (MMHGR) and/or maximum diameter coefficient (MDC);
when comparing said group of transgenic plants grown for 8 weeks in a greenhouse under a photoperiod of 18 hours, a temperature of 22° C./15° C. (day/night) and a weekly fertilization with N 84 g/l, PI 2 g/l, K 56 g/l, with a group of wild-type plants grown under identical conditions;
wherein the maximum height growth rate is defined by calculating the slope of a linear function fitted over four consecutive height data points, a height growth rate value is calculated for data point 1-4, data point 2-5 etc. in a step-wise manner and the maximum height growth rate value is finally selected from the growth rate values for each plant.

According to particular embodiments of the invention the level of a gene product of at least one gene comprising a nucleotide sequence selected from the group consisting of:
  a) a nucleotide sequence from SEQ ID NO:1-17, 50, 51, 54-58, 60; such as SEQ ID NO: 1, 2, 5, 6, 10, 13, 15, 16, 17, 50, 51, 54, 55, 56, 57, 58, 60.
  b) a nucleotide sequence being at least 60% identical to a nucleotide sequence from SEQ ID NO:1-17, 50, 51, 54-58, 60; such as SEQ ID NO: 1, 2, 5, 6, 10, 13, 15, 16, 17, 50, 51, 54, 55, 56, 57, 58, 60,
  c) a subsequence or fragment of a nucleotide sequence of a) or b) has been altered relative to the level found in the respective corresponding wild-type plant.

According to yet another embodiment of the invention, the transgenic plant comprises a recombinant polynucleotide (DNA construct) comprising a nucleotide sequence selected from the group consisting of:
  d) a nucleotide sequence comprising a sequence selected from SEQ ID NO:1-17, 50, 51, 54-58, 60; such as SEQ ID NO: 1, 2, 5, 6, 10, 13, 15, 16, 17, 50, 51, 54, 55, 56, 57, 58, 60,
  e) a complementary nucleotide sequence of a nucleotide sequence of d);
  f) a sub-sequence or fragment of a nucleotide sequence of d) or e);
  g) a nucleic acid sequence being at least 60% identical to any one of the sequences in d), e) and f); and
  h) a nucleotide sequence which hybridizes under stringent conditions to a nucleotide sequence of d), e) or f).

In further embodiments of this aspect of the invention the nucleic acid sequence in c) or g) is at least 65% identical to any one of the sequences in a), b), d), e) or f), such as at least 70% identical, at least 75% identical, at least 80% identical, at least 85% identical, at least 87% identical, at least 90% identical, at least 95% identical, at least 97% identical, at least 98% identical, at least 99% identical, or at least 99.5% identical to any one of the sequences in a), b), d), e) or f).

As mentioned above the skilled person will realize that a variety of methods exist in the art for producing the nucleic acid sequences and polynucleotide constructs of the invention, e.g. by cloning techniques, assembly of fragments generated by solid phase synthesis. Again, the skilled person will understand, homologues of the described sequences may be isolated from other species, non-limiting examples of which include acacia, eucalyptus, hornbeam, beech, mahogany, walnut, oak, ash, hickory, birch, chestnut, alder, maple, sycamore, ginkgo, palm tree, sweet gum, cypress, Douglas fir, fir, *sequoia*, hemlock, cedar, juniper, larch, pine, redwood, spruce and yew, apple, plum, pear, banana, orange, kiwi, lemon, cherry, grapevine, fig, cotton, bamboo, switchgrass, red canary grass and rubber plants. Useful homologues of the described sequences may also be isolated from hardwood plants from the Salicaceae family, such as from willow, poplar or aspen.

In particular, the nucleotide sequence according to the invention comprises a sequence selected from those of SEQ ID NOs: 18-38, 48, 49, 51-60; such as SEQ ID NO: 20, 29, 36, 37, 38, 48, 49, 51-60, or a complementary nucleotide sequence thereof.

Again, it will be apparent that the sub-sequences or fragment in c) or f) as described above comprises at least 15 nucleotides, such as at least 16 nucleotides, at least 17 nucleotides, at least 18 nucleotides, at least 19 nucleotides, at least 20 nucleotides, at least 21 nucleotides, at least 22 nucleotides, at least 23 nucleotides, at least 24 nucleotides, at least 25 nucleotides, e.g. at least 30 nucleotides, at least 35 nucleotides, at least 40 nucleotides, at least 45 nucleotides, at least 50 nucleotides, at least 55 nucleotides, at least 60 nucleotides, at least 65 nucleotides, at least 70 nucleotides, at least 75 nucleotides, at least 80 nucleotides, at least 85 nucleotides, at least 90 nucleotides, at least 95 nucleotides, or such as at least 100 nucleotides. In certain embodiments, the sub-sequences or fragment in c) or f) as described above comprises at least about 150 nucleic acid residues, such as at least about 200, 250, 300, 330, 360, 375, 400, 425, 450, 460, 480, 500, 600, 700, 800 such as at least about 900 nucleotides or such as at least about 1 kb, 1.1 kb, 1.2 kb, 1.3 kb, 1.4 kb, 1.5 kb, 1.6 kb, 1.7 kb, 1.8 kb, 1.9 kb, 2 kb, 2.1 kb, 2.2 kb, 2.3 kb, 2.4 kb, 2.5 kb, 2.6 kb, 2.7 kb, 2.8 kb, 2.9 kb or such as at least about 3 kb.

In particular, the transgenic plant according to the present invention may comprise a recombinant DNA construct comprising a nucleotide sequence which relative to the particular sequences described, comprises conservative variations altering only one, or a few amino acids in the encoded polypeptide may also be provided and used according to the present invention. Accordingly, it is within the scope of the invention to provide a transgenic plant comprising a recombinant DNA construct comprising a nucleotide sequence which encodes a polypeptide comprising a conservatively substituted variant of a polypeptide of a) or d).

Accordingly, the present invention may also provide a recombinant DNA construct, wherein the nucleotide sequence comprises a silent substitution in a nucleotide sequence, that is, the recombinant DNA construct may comprise a sequence alteration that does not change the amino acid sequence encoded by the polynucleotide.

In certain further embodiments of the invention, the sub-sequences or fragments have at least 65% sequence identity to a conserved domain of a nucleotide sequence as described above under item a) or d), such as at least 70% identical, at least 75% identical, at least 80% identical, at least 85% identical, at least 87% identical, at least 90% identical, at least 95% identical, at least 97% identical, at least 98% identical, at least 99% identical, or at least 99.5% identical to a conserved domain of a nucleotide sequence as described above under item a) or d).

In the particular embodiments by which the present invention is exemplified the sub-sequences or fragments in c) comprise the sequences of SEQ ID NOs: 18-38, 48, 49, 51-60; such as SEQ ID NO: 20, 29, 36, 37, 38, 48, 49, 51-60.

In further embodiments the transgenic plant provided according to the invention comprises a recombinant polynucleotide construct which further comprises a constitutive, inducible, or tissue specific promoter operably linked to said nucleotide sequence.

In still further embodiments the recombinant polynucleotide construct further comprises a strong constitutive promoter in front of a transcribed cassette consisting of part of the target gene followed by a plant functional intron followed by the same part of the target gene in reverse orientation as described above. Another preferred type of recombinant polymucleotide construct has a promoter driving the transcription of a DNA fragment from a target gene followed of an shorter sequence that are present in an inverted repeat, as also explained above.

In the particular embodiments by which the present invention is exemplified, the transgenic plant comprises a recombinant polynucleotide construct in which the sub-sequences or fragments in c) comprise the sequences of SEQ ID NOs: 18-38, 48, 49, 51-60; such as SEQ ID NO: 20, 29, 36, 37, 38, 48, 49, 51-60.

In a presently preferred embodiment of the invention, the transgenic plant according to the invention comprises a recombinant DNA construct comprising the sequence of SEQ ID NO: 47.

Plant Species

In accordance with the present invention, the transgenic plant may be a perennial plant which preferable is a woody plant or a woody species. In a useful embodiment, the woody plant is a hardwood plant which may be selected from the group consisting of acacia, eucalyptus, hornbeam, beech, mahogany, walnut, oak, ash, willow, hickory, birch, chestnut, poplar, alder, maple, sycamore, ginkgo, a palm tree and sweet gum. Hardwood plants from the Salicaceae family, such as willow, poplar and aspen including variants thereof, are of particular interest, as these two groups include fast-growing species of tree or woody shrub which are grown specifically to provide timber and bio-fuel for heating.

In further embodiments, the woody plant is a conifer which may be selected from the group consisting of cypress, Douglas fir, fir, *sequoia*, hemlock, cedar, juniper, larch, pine, redwood, spruce and yew.

In useful embodiments, the woody plant is a fruit bearing plant which may be selected from the group consisting of apple, plum, pear, banana, orange, kiwi, lemon, cherry, grapevine and FIG.

Other woody plants which may be useful in the present method may also be selected from the group consisting of cotton, bamboo and rubber plants.

The present invention extends to any plant cell of the above transgenic plants obtained by the methods described herein, and to all plant parts, including harvestable parts of a plant, seeds and propagules thereof, and plant explant or plant tissue. The present invention also encompasses a plant, a part thereof, a plant cell or a plant progeny comprising a DNA construct according to the invention. The present invention extends further to encompass the progeny of a primary transformed or transfected cell, tissue, organ or whole plant that has been produced by any of the aforementioned methods, the only requirement being that progeny exhibit the same genotypic and/or phenotypic characteristic(s) as those produced in the parent by the methods according to the invention.

It should be noted that embodiments and features described in the context of one of the aspects of the present invention also apply to the other aspects of the invention.

All patent and non-patent references cited in the present application, are hereby incorporated by reference in their entirety.

The invention will now be described in further details in the following non-limiting examples.

EXAMPLES

Example 1

Identification of Useful Genes Involved in Wood Formation and Wood Growth 1.1 Introduction In order to find and elucidate the function of genes involved in wood formation and wood growth, an extensive gene mining program was performed, resulting in the identification of genes useful in wood industrial applications.

1.2. Materials and Methods 1.2.1 Gene Selection

The first step in this gene mining program was to select some genes from a large gene pool in order to narrow the genes to be tested for their function. The gene selection method is based on gene expression patterns as described in Hertzberg et al. (2001) and Schrader et al. (2004).

In Hertzberg et al. (2001) a study of the developing secondary xylem of poplar is described. The secondary xylem of poplar is highly organised with easily recognized and distinct boundaries between the different developmental stages. Wood formation is initiated in the vascular cambium. Cambial derivatives develop into xylem cells through the processes of division, expansion, secondary wall formation, lignification and, finally, programmed cell death.

The large physical size of the vascular meristem in trees was used to obtain samples from defined developmental stages by tangential cryo sectioning. To determine the steady state mRNA levels at specific stages during the ontogeny of wood formation in *Populus tremula×tremuloides* (hybrid aspen) samples of 30 μm thick sections were obtained through the wood development region and subsequently the samples were analysed using a spotted cDNA-microarray consisting of 2995 unique ESTs from hybrid aspen (Hertzberg et al, 2001).

Figure 1A:
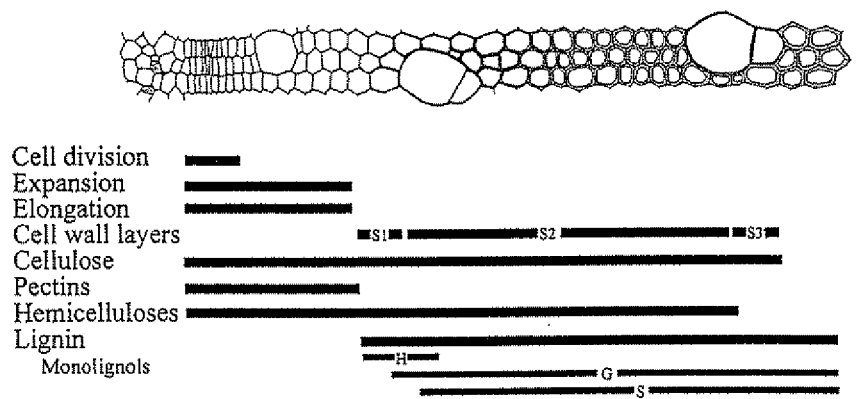
Figure 1B:
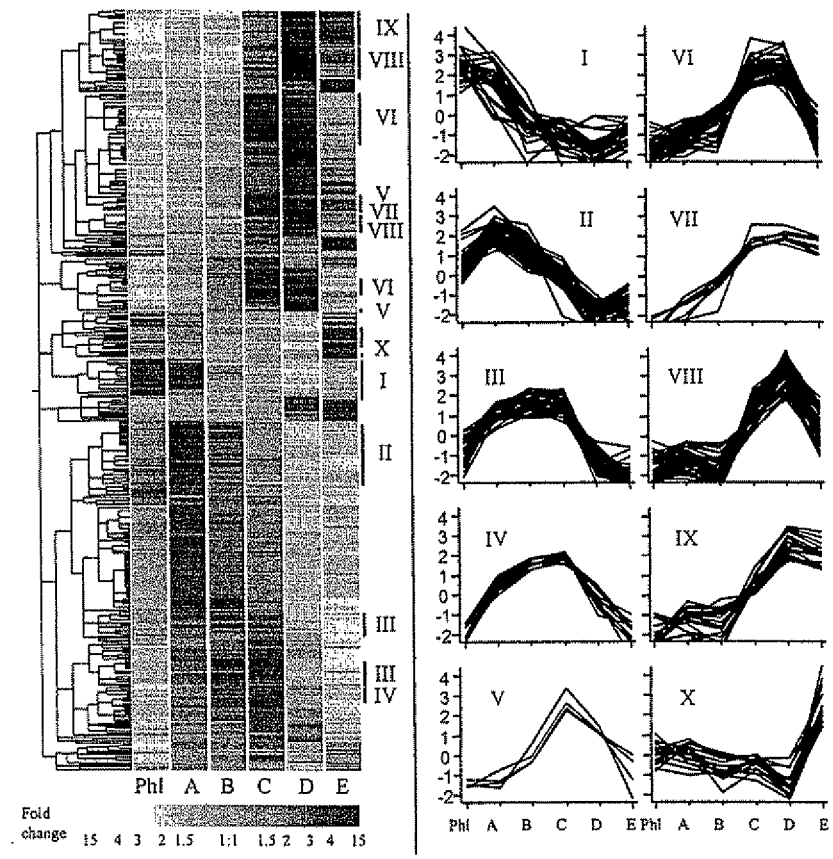

These samples were also subsequent re-hybridized to the spotted micro array as described in Schrader et al. (2004). From these experiments, genes with a clear specific expression during the different phases of wood formation where selected (see FIG. 1). Basis for this is the assumption that genes usually have their function where they are expressed. Thus, genes that are specifically expressed during the different wood formation phases such as cell-division, cell expansion and cell commitment in the cambial zone, and genes expressed during the secondary cell wall formation in the maturation zone (see Wilson, et al., 1966 for definitions), are more likely to be important for wood formation processes than any randomly chosen gene. Like other plant meristems, the main function of the vascular cambium (FIG. 1, zone A) is cell division and the initiation of differentiation. Sequences expressed primarily in the meristem and in the zone of early cell expansion (FIG. 1, zone B) represent candidate genes involved in cell cycling, cell expansion, tip growth of fibres and biosynthesis of the primary cell wall. Zones A and B are also expected to express genes that regulate cell fate and cell identity. Cell expansion takes place in the meristem (zone A) and in zones B and C. Genes with an expression across the zones A, B and C (FIG. 1) may therefore function in cell expansion. As soon as cell expansion is completed, the secondary cell wall is deposited in all xylem cells (zone D). The majority of genes involved in the biosynthesis of the secondary cell wall, were predicted to be found in zones C (where the vessels initiate their secondary cell wall), D and E (FIG. 1). Genes strongly up-regulated in zone E (FIG. 1) include many wall-degrading enzymes required for cell wall sculpturing through final stages of the formation of pits and pores, or genes related to late phases of fibre maturation such as lignification and programmed cell death. Genes expressed in this zone also contains genes specifically involved in metabolism and transport in ray cells, which as opposed to the fibres, remain alive and maintain their metabolic activity.

Figure 2:
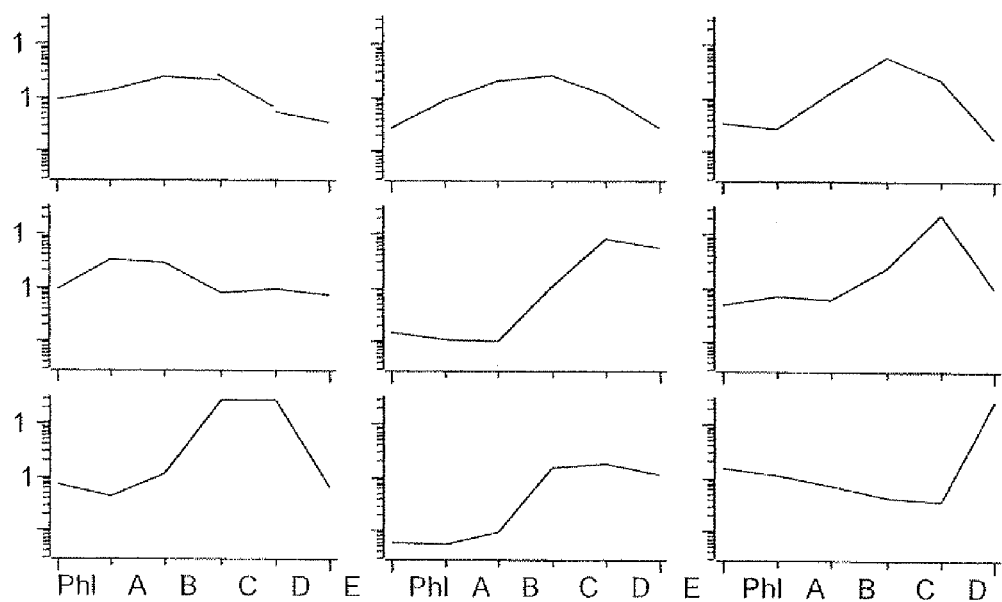
FIG. 2 shows the expression patterns for the selected genes, from the xylem differentiation data. Nine principal examples of genes selected from the Hertzberg et al (2001) data set for functional analysis in Hybrid aspen. The same samples and figure as in FIG. 1D, The graph shows the expression pattern of those genes over the xylem differentiation zone. Expression ratios are on log scale.

A large number of different genes expressed during different stages of xylem development were selected for functional genomic analysis using RNAi down regulation in transgenic poplar plants. FIG. 2 shows examples of expression patterns for genes that were selected and tested for their function.

In addition to this selection, genes were selected based on the meristem array gene expression experiment described in Schrader et al. (2004). In this experiment only the cambial zone were sampled. However, the samples were thinner resulting in a higher resolution over the cambial meristem, i.e. one section corresponded to approximately three cell layers of the cambial zone, thus, providing near cell-specific resolution for the obtained expression profiles. From this experiment, genes with a peak within the cambial zone or having a steep change in expression over the cambial meristem (Schrader et al. 2004) were selected for functional genomic analysis using RNAi down regulation in transgenic poplar plants.

Subsequent to the selections based on expression patterns, the genes were screened based on gene annotations, and genes with apparently uninteresting gene annotations, such as ribosomal protein genes, were excluded. The use of careful selection of the genes to be functionally tested in a functional genomic program directed towards growth and wood properties is very beneficial in order to reduce cost and to search out to the interesting genes faster.

Although the selection of the genes, for which functions are analysed, are an important part of the discovery of genes with functions interesting for forest biotechnology in an economic efficient way, it is the actual testing of the gene function of the selected genes which is the crucial step for finding their use in industrial applications. Gene selection such as it is performed here is merely important in order to maximize the positive output of a functional genomics program (e.g. large scale testing of genes using mutants or transgenic plants/organisms) directed against certain properties/functions.

Figure 3:
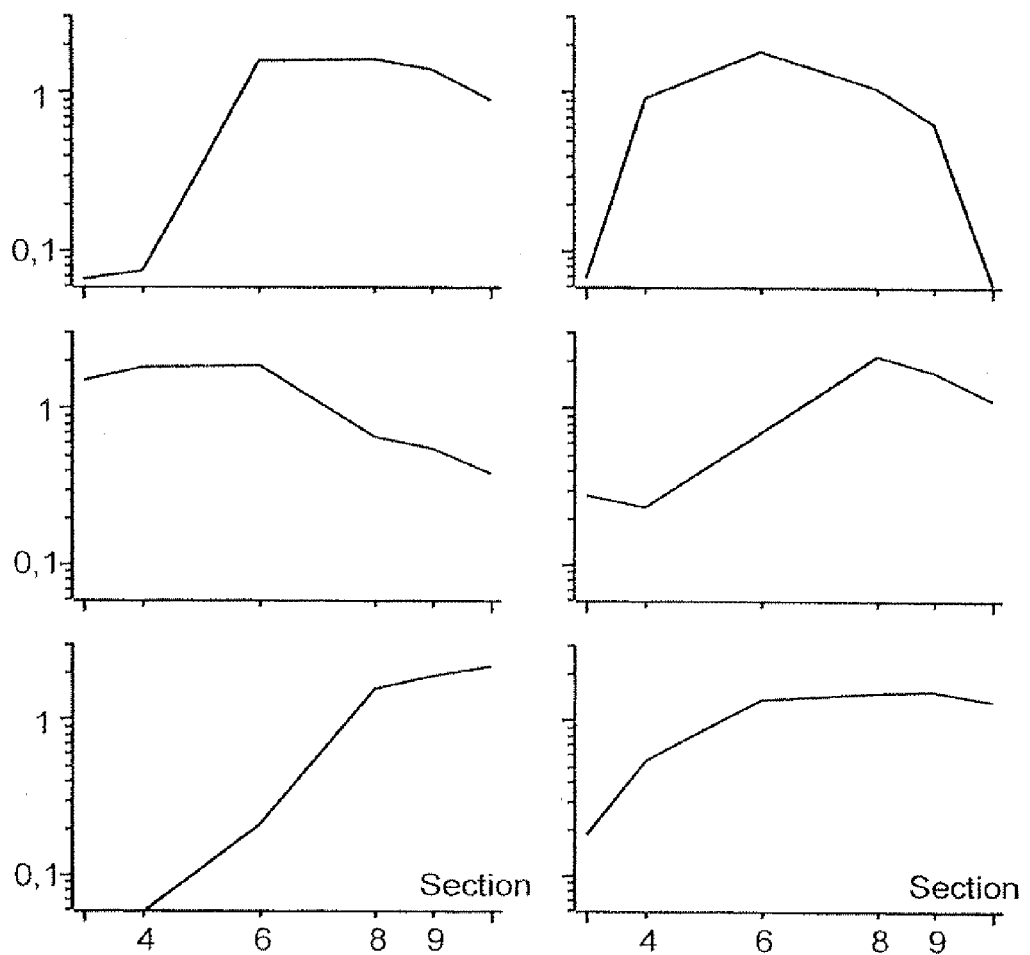
FIG. 3 shows the expression patterns for the selected genes from the meristem experiment data. Six principal examples of genes selected from the Schrader et al (2004) data set for functional analysis in Hybrid aspen. The same samples and figure as in FIG. 1D. The graphs show the expression pattern of those genes over the cambial zone. Expression data is from the B serie from Schrader et al 2004. Expression values are on log scale, for an explanation of the normalization and data preparation (See Schrader et al 2004)

The result of the gene selection was 184 potential genes, 150 of these were finally functionally analysed, 17 genes of which were further selected for their involvement and use in changing and/or modifying the phenotype of the tree with regard to growth and improved wood chemistry. Examples of expression patterns from the 184 selected genes are shown in FIG. 2 and FIG. 3.

1.2.2 Cloning of the Selected Genes

Selected genes were subsequently cloned into a RNAi vector under the control of the CaMV 35S promoter (RNA interference vector, pK7GWIWG2(I)) using Gateway technology (Invitrogen USA). Two principal sets of cloning primers were used, one set was a universal primer pair binding to the vector and the poly-A tail, and the other set were gene-specific primers. The PCR product was first transferred into the pDONR vector (Invitrogen USA) and subsequently transferred into the destination vector pK7GWIWG2(I) according to manufacturers recommendations (Invitrogen USA). The sequences of the selected genes, their gene bank accession numbers and PCR primers etc. are listed in Table 1.1.

TABLE 1.1

Gene bank accession numbers, sequences and PCR primers etc.

Table 1.1a

| Construct | Name cloning Forward primer FW name | FW sequence | Name cloning Reverse primer Rev name | Rev sequence |
|---|---|---|---|---|
| KR121 | attB1-T12VN | SEQ ID NO: 39 | attB2-T7 | SEQ ID NO: 43 |
| KR125 | attB1-T12VN | | attB2-T7 | |
| KR129B | attB1-T12VN | | attB2-T7 | |
| KR140 | attB1-T12VN | | attB2-T7 | |
| KR152 | attB1-T12VN | | attB2-T7 | |
| KR163 | attB1-T12VN | | attB2-T7 | |
| KR221 | attB1-T12VN | | attB2-T7 | |
| KR224 | attB1-T12VN | | attB2-T7 | |
| KR235 | attB1-T12VN | | attB2-T7 | |
| KR240 | attB1-T12VN | | attB2-T7 | |
| KR242 | attB1-T12VN | | attB2-T7 | |
| KR292 | attB1-T12VN | | attB2-T7 | |
| KR313 | attB1-T12VN | | attB2-T7 | |
| KR318 | attB1-T12VN | | attB2-T7 | |
| KR459 | KR459FwAttB2 | SEQ ID NO: 40 | KR459ReAttB1 | SEQ ID NO: 44 |
| KR463 | KR463FwAttB2 | SEQ ID NO: 41 | KR463ReAttB1 | SEQ ID NO: 45 |
| KR465 | KR465FwAttB2 | SEQ ID NO: 42 | KR465ReAttB1 | SEQ ID NO: 46 |

Table 1.1b

| Construct | Sequence used for RNAi construct: | Full sequence |
|---|---|---|
| KR121 | SEQ ID NO: 18 | SEQ ID NO: 1 |
| KR125 | SEQ ID NO: 19 | SEQ ID NO: 2 |
| KR129B | SEQ ID NO: 20 | SEQ ID NO: 3 |
| KR140 | SEQ ID NO: 21 | SEQ ID NO: 4 |
| KR152 | SEQ ID NO: 22 | SEQ ID NO: 5 |
| KR163 | SEQ ID NO: 23 | SEQ ID NO: 6 |
| | SEQ ID NO: 24 | |
| KR221 | SEQ ID NO: 25 | SEQ ID NO: 7 |
| KR224 | SEQ ID NO: 26 | SEQ ID NO: 8 |
| KR235 | SEQ ID NO: 27 | SEQ ID NO: 9 |
| | SEQ ID NO: 28 | |
| KR240 | SEQ ID NO: 29 | SEQ ID NO: 10 |
| KR242 | SEQ ID NO: 30 | SEQ ID NO: 11 |
| KR292 | SEQ ID NO: 31 | SEQ ID NO: 12 |
| KR313 | SEQ ID NO: 32 | SEQ ID NO: 13 |
| | SEQ ID NO: 33 | |
| KR318 | SEQ ID NO: 34 | SEQ ID NO: 14 |
| | SEQ ID NO: 35 | |
| KR459 | SEQ ID NO: 36 | SEQ ID NO: 15 |
| KR463 | SEQ ID NO: 37 | SEQ ID NO: 16 |
| KR465 | SEQ ID NO: 38 | SEQ ID NO: 17 |

Table 1.1c

| Construct | New Seq ID No | Updated or complemented sequence used for RNAi construct | Updated or complemented full sequence |
|---|---|---|---|
| KR121 | SEQ ID NO: 48 | SEQ ID NO: 18 | |
| KR125 | SEQ ID NO: 49 | SEQ ID NO: 19 | |
| KR129B | SEQ ID NO: 50 | | SEQ ID NO: 3 |
| KR140 | SEQ ID NO: 51 | SEQ ID NO: 21 | SEQ ID NO: 4 |
| KR152 | SEQ ID NO: 52 | SEQ ID NO: 22 | |
| KR163 | SEQ ID NO: 53 | SEQ ID NO: 23 | |
| | | SEQ ID NO: 24 | |
| KR221 | SEQ ID NO: 54 | SEQ ID NO: 25 | SEQ ID NO: 7 |
| KR224 | SEQ ID NO: 55 | SEQ ID NO: 26 | SEQ ID NO: 8 |
| KR235 | SEQ ID NO: 56 | SEQ ID NO: 27 | SEQ ID NO: 9 |
| | | SEQ ID NO: 28 | |
| KR242 | SEQ ID NO: 57 | SEQ ID NO: 30 | SEQ ID NO: 11 |
| KR292 | SEQ ID NO: 58 | SEQ ID NO: 31 | SEQ ID NO: 12 |
| KR313 | SEQ ID NO: 59 | SEQ ID NO: 32 | |
| | | SEQ ID NO: 33 | |
| KR318 | SEQ ID NO: 60 | SEQ ID NO: 34 | SEQ ID NO: 14 |
| | | SEQ ID NO: 35 | |

KR121
Further sequencing analysis of KR121 resulted in new sequence, referred to as SEQ ID NO:48. This new sequence complements SEQ ID NO:18 by adding about 28 bases in the five prime end and updating about 10 bases within the sequence.
KR125
Further sequencing analysis of KR125 resulted in new sequence, referred to as SEQ ID NO:49. This sequence complements SEQ ID NO:19 by adding about 32 bases in the five prime end, updating about 10 bases within the sequence and adding another 881 bases of three prime sequence.
KR129B
SEQ ID NO:50 fully replace SEQ ID NO:3 because the wrong Gene Model sequence was given as full sequence.
KR140
Further sequencing analysis of KR140 resulted in new sequence, referred to as SEQ ID NO:51. This sequence complements SEQ ID NO:21 by adding about 287 bases in the three prime end and it will also update SEQ ID NO:4 as the full sequence of KR140.
KR152
Further sequencing analysis of KR152 resulted in new sequence, referred to as SEQ ID NO:52. This sequence complements SEQ ID NO:22 by updating 7 bases.
KR163
Further sequencing analysis of KR163 resulted in new sequence, referred to as SEQ ID NO:53. This sequence cover the whole cDNA where SEQ ID NO:23 and SEQ ID NO:24 cover the five and three prime part respectively. SEQ ID NO:53 is adding 351 bases in between the sequences. It is also adding about 46 bases in the five prime end and updating about 10 bases in the sequences.
KR221
Further sequencing analysis of KR221 resulted in new sequence, referred to as SEQ ID NO:54. This sequence complements SEQ ID NO:25 and SEQ ID NO:7 by addition of about 11 bases in the five prime end and updating the sequence from the 500:th base up to the three prime end.
KR224
Further sequencing analysis of KR224 resulted in new sequence, referred to as SEQ ID NO:55. This sequence complements SEQ ID NO:26 by addition of about 778 bases tree prime of the sequence and updating about 10 bases within the sequence. It will also update the SEQ ID NO:8 as the full sequence of 224.
KR235
Further sequencing analysis of KR235 resulted in new sequence, referred to as SEQ ID NO:56. This sequence cover the whole cDNA where SEQ ID NO:27 and SEQ ID NO:28 cover the five and three prime part respectively. SEQ ID NO:56 is adding 161 bases in between the sequences. It will also update the SEQ ID NO:9 as the full sequence of KR235.
KR242
Further sequencing analysis of KR242 resulted in new sequence, referred to as SEQ ID NO:57. This sequence complements the SEQ ID NO:30 and SEQ ID NO:11 by updates of about 30 bases in the sequence.
KR292
Further sequencing analysis of KR292 resulted in new sequence, referred to as SEQ ID NO:58. This sequence complements SEQ ID NO:31 and SEQ ID NO:12 by adding about 36 bases in the five prime end and updating about 20 bases within the sequence.
KR313
Further sequencing analysis of KR313 resulted in new sequence, referred to as SEQ ID NO:59. This sequence cover the whole cDNA where SEQ ID NO:32 and SEQ ID NO:33 cover the five and three prime part respectively. SEQ ID NO:59 is adding 84 bases in between the sequences and updating about 6 bases within the sequences.
KR318
Further sequencing analysis of KR318 resulted in new sequence, referred to as SEQ ID NO:60. This sequence fully replace SEQ ID NO:34, SEQ ID NO:35 and SEQ ID NO:14. The first presented sequences were wrong due to a clone mix up. The transgenes presented are based on the new SEQ ID NO:60.

1.2.3 Plant Transformation

CaMV 35S: Inverted repeat DNA constructs were transformed into *Agrobacterium* and subsequent into Hybrid aspen, *Populus tremula* L.×*P. tremuloides* Minch. Clone T89, hereafter called "poplar", was transformed and regenerated essentially as described in Nilsson et al. (1992). Approximately 3-8 independent lines were generated for each construct. One such group of transgenic trees produced using one construct is hereafter called a "construction group", e.g. different transgenic trees emanating from one construct. Each transgenic line within each construction group, e.g. KR555-2B KR555-3A, KR555-2B and so on, are different transformation events and therefore most probably have the recombinant DNA inserted into different locations in the plant genome. This makes the different lines within one construction group partly different. For example it is known that different transformation events will produce plants with different levels of gene down-regulation when using RNAi constructs of the type used here.

1.2.4 Plant Growth

The transgenic poplar lines were grown together with their wild type control (wt) trees, in a greenhouse under a photoperiod of 18 h and a temperature of 22° C./15° C. (day/night). The plants were fertilized weekly Weibulls Rika S NPK 7-1-5 diluted 1 to 100 (final concentrations NO3, 55 g/l; NH4, 29 g/l; P, 12 g/l; K, 56 g/l; Mg 7.2 g/l; S, 7.2 g/l; B, 0.18 g/l; Cu, 0.02 g/l; Fe, 0.84 g/l; Mn, 0.42 g/l; Mo, 0.03 g/l; Zn, 0.13 g/L). The plants were grown for 8-9 weeks before harvest. During this time their height and diameter was measured 1 to 2 times per week. A number of wild type trees (typically 15-25 trees) and a number of transgenic trees comprising several construction groups (typically 6-20 construction groups) were grown in parallel in the greenhouse under the same above conditions. All comparisons between the wild type trees and construction groups are made within each growth group.

1.2.5 Sampling

Two principal types of harvest and sampling were performed. One general type was for example for chemical analysis, wood morphological analysis, gene expression analysis, wood density analysis and metabolomics analysis. And another type for dry weight measurements of bark, wood, leafs and roots.

1.2.6 Selection of Construction Groups

In the first round of growth for each group of trees with a specific gene down regulated using RNAi, i.e. a construction group, a number of the following analyses were performed: Growth measurements. These data were analysed in order to single out the Construction Groups that showed a phenotypic variation compared to wild type control trees.

Based on the growth data a number of analyses and factors were performed and calculated in order to select the construction groups and thereby the genes which are possible to use for altering growth characters. Selection criteria's and methods were as described below.

Growth Analysis

Growth During Exponential Phase

Under the above defined growth conditions, plants exhibit an exponential growth pattern (plant height) up to an approximate height of 80 cm or up to day 40 in the greenhouse. For each plant, data points of plant height within these bounds were used for fitting of an exponential function in the form of:

$$h(t)=h_0 * e^{at}$$

where $h_0$ is a constant (height at t=0) and a is defined as the rate of exponential growth.

Maximum Height Growth Rate

Figure 4:
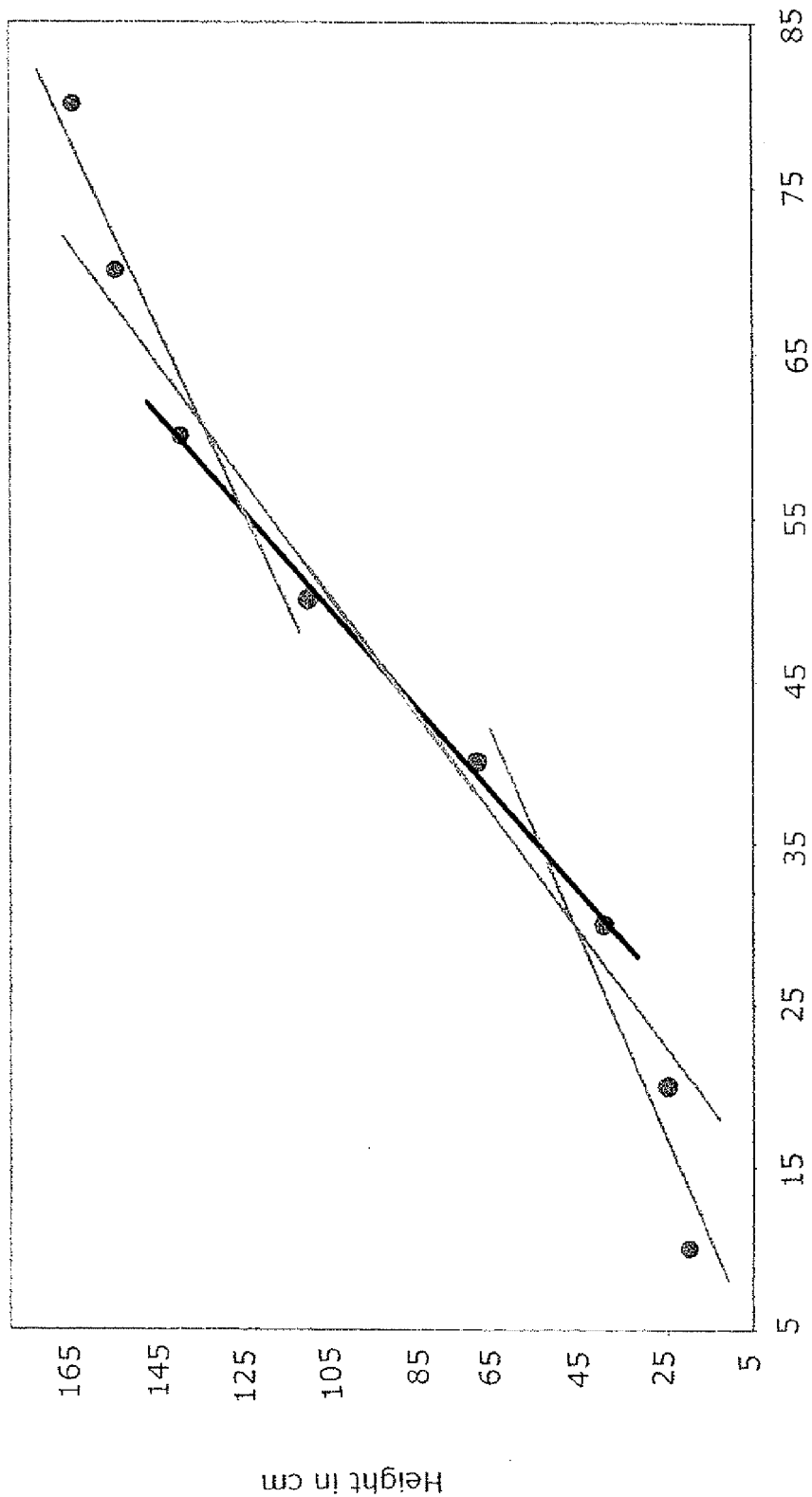
FIG. 4 shows an example of a height growth curve with four different data point linear regression lines shown, the black regression line shows the maximum height growth rate.

Another height growth rate measure (here named "Maximum height growth rate") was defined as the slope of a linear function fitted over four consecutive height data points. A height growth rate value was calculated for data point 1-4, data point 2-5 etc. in a step-wise manner, se FIG. 4 for an example. A maximum growth rate defined as the maximum value, produced from step-wise linear regression analysis, for each plant was computed. The primary data for high Maximum height growth rate values from individual transformants in a construction group were checked so they were not based on bad values. From FIG. 4, showing an example of a height growth curve, it can be seen that the height growth rate increases during the first part of growth then the plants reach their maximum height growth and then the growth rate declines as the plants become larger. Because these phases have different timing in different plants and there are some noise added measuring the plants our above described Maximum height growth using rate method is very useful in calculating the maximum growth speed in these conditions for the different individual trees.

Diameter Growth Rate

Under the above defined growth conditions, stem width exhibit a comparatively linear increase over time. Linear regression on diameter data was used for estimating diameter growth.

$$d(t)=c*t+d_0$$

where $d_0$ is the initial width and c is the rate of diameter growth (slope).

Final Height and Diameter

The final height and diameter were also used to select altered construction groups. These values take into account both the trees growth capacity and the trees ability to start their growth when transferred from tissue culture into soil and placed in a greenhouse.

Selection Parameters

Construction groups that showed a significant or pronounced increase compared to the wild type population in the above mentioned growth parameters, i.e. diameter growth rate, maximum height growth rate, final height and final diameter, were scored as Construction Groups that are altered in their growth properties, and therefore, the corresponding genes can be used to alter these properties. The selection criteria's are stated below. Two different selection levels were used, one basic level and one for constructs giving growth phenotypes of extra interest.

Growth Difference Selection Criteria

In Table 1.2 the abbreviations used for the phenotypes used for the growth selection criteria are listed.

TABLE 1.2

Abbreviations for the phenotypes

| | |
|---|---|
| AFH | Average final height of the wild type population and each Construction group population |
| AFD | average final diameter of the wild type population and each Construction group population |
| AMHGR | average Maximum height growth rate of the wild type population and each Construction group population |
| ADGR | Average diameter coefficient of the wild type population and each Construction group population |
| MFH | Maximum final height of the wild type population and each Construction group population |
| MFD | Maximum final diameter of the wild type population and each Construction group population |
| MMHGR | Maximum of Maximum height growth rate of the wild type population and each Construction group population |
| MDC | Maximum diameter coefficient of the wild type population and each Construction group population |

The growth difference selection criteria are as follows:
1. If construction group AFH, MFH, AMHGR and MMHGR are at least 5% (or 8% in a second higher level) greater than corresponding wild type group AFH, MFH, AMHGR and MMHGR, or
2. If construction group AFD, MFD, ADGR and MDC are at least 5% (or 8% in a second higher level) greater than corresponding wild type group AFD, MFD, ADGR and MDC, or
3. If construction group AFH, AFD, AMHGR or ADGR is at least 18% (or 22% in the second higher level) greater than corresponding wild type group AFH, AFD, AMHGR or ADGR, or
4. If construction group MFH, MFD, MMHGR or MDC is at least 18% (or 22% in the second higher level) greater than corresponding wild type group MFH, MFD, MMHGR or MDC Running a large scale functional genomics program produces a certain amount of variation and uncertainty in the data produced. In this set up variation is produced from sources such as: that the different lines within an construction group have different amounts of down regulation resulting in that one to all tested lines within an construction group can show the phenotype; the variation in growth that occur during the experimental procedure due to small variations in plant status when transferring the plants from tissue culture to the greenhouse and variations based on different positions in the greenhouse during different time points during the growth cycle. These variations have to be dealt with when analysing the data. Based on these two different thresholds of increase 5% and 18% were used for selecting construction groups with increased growth. The selection criteria 1 and 2 uses an 5% increase, however this increase have to be present in all the phenotypes AFH, MFH, AMHGR and MMHGR corresponding to height growth or all the phenotypes AFD, MFD, ADGR and MDC corresponding to diameter growth. In the cases that the phenotype only can be seen in some or one of the plants and only in one phenotype class, an higher 18% increase were used to select positive construction groups in order not to select construction groups based on random variations (selection criteria's 3 and 4 selecting on average values and maximum individual values respectively). These numbers were checked against the wild type data. The 18% level for filter 3 and 4 were passed by no wild type plants, e.g. no wild type plant in any of the growth groups had an more than a 18% higher value than the wild type with the $2^{nd}$ highest value in any of the used growth phenotypes. The 5% level used for filter 1 and 2 produce less than 4% false positives (1 in genes), e.g. randomly removing 5 wild type plants from the wild type control population and testing them for passing filters 1 and 2 and performing that for all the growth groups and repeating this 10 times gives that in 4% of the times the removed wild type plants will pass the filter. This is a very tough method to estimate the false positives, because the wild type control group is lowered with 5 plants. For the higher value 8% used for the genes of extra interest, this produce less than 1.5% false positives.

Construction groups meeting one or more of these criteria were selected.

Internod Length Measurement

All the nodes from the FDL node and included 60 cm downwards the stem was counted and the average internode length was calculated.

1.3 Results

The growth raw data for the specified construction group and the corresponding wild type group are shown in tables 1.3 to 1.20. Table rows contain height and diameter measurements of individuals of specified construction group (named "KR") and corresponding wild type group (named "T89"). Time of measurement, i.e. no. of days in greenhouse, is shown in the table header.

Construction Group KR221

Construct KR221 corresponding to EST A013P18U gene bank number A1162169. This gene is selected from the Hertzberg et al 2001 data and is up-regulated in the D zone. This construct induces increased growth. The construction group population shows a 21% average increase in diameter growth rate compared to the wt population. Construction group meets Growth Filter criterion (3).

TABLE 1.3

Growth data for KR221

| Days in greenhouse | Height (cm) | | | | | | | Diameter (mm) | | | |
|---|---|---|---|---|---|---|---|---|---|---|---|
| | 18 | 21 | 26 | 29 | 33 | 43 | 56 | 26 | 29 | 33 | 56 |
| KR221rp1-4B-1 | 13 | 18 | 26 | 33 | 47 | 84 | 115 | 3.5 | 4.0 | 4.8 | 8.7 |
| KR221rp1-4B-2 | 16 | 22 | 33 | 41 | 54 | 93 | 120 | 3.8 | 4.4 | 5.4 | 9.4 |

TABLE 1.3-continued

Growth data for KR221

| Days in greenhouse | Height (cm) | | | | | | | Diameter (mm) | | | |
|---|---|---|---|---|---|---|---|---|---|---|---|
| | 18 | 21 | 26 | 29 | 33 | 43 | 56 | 26 | 29 | 33 | 56 |
| KR221rp1-4B-3 | 18 | 23 | 33 | 44 | 59 | 104 | 137 | 3.7 | 4.9 | 5.9 | 9.1 |
| T89-1 | 26 | 33 | 46 | 57 | 71 | 109 | 139 | 4.1 | 4.9 | 5.8 | 8.9 |
| T89-2 | 28 | 36 | 48 | 58 | 75 | 113 | 141 | 5.1 | 6.3 | 7.1 | 9.5 |
| T89-3 | 25 | 32 | 45 | 55 | 70 | 110 | 136 | 5.2 | 5.5 | 7.1 | 9.6 |
| T89-4 | 23 | 29 | 41 | 52 | 67 | 110 | 142 | 4.4 | 4.9 | 5.9 | 9.1 |
| T89-5 | 27 | 37 | 48 | 59 | 74 | 120 | 150 | 4.9 | 5.7 | 6.9 | 9.4 |
| T89-6 | 25 | 32 | 45 | 54 | 67 | 107 | 137 | 4.7 | 5.9 | 5.9 | 9.2 |
| T89-7 | 27 | 34 | 47 | 58 | 72 | 113 | 140 | 4.4 | 5.3 | 6.2 | 9.5 |
| T89-8 | 27 | 34 | 45 | 55 | 70 | 111 | 140 | 5.0 | 6.1 | 6.7 | 10.2 |
| T89-9 | 24 | 30 | 42 | 51 | 67 | 110 | 138 | 4.1 | 5.0 | 6.6 | 9.5 |
| T89-10 | 24 | 31 | 42 | 51 | 66 | 104 | 135 | 4.6 | 5.5 | 6.1 | 8.5 |
| T89-11 | 23 | 30 | 43 | 55 | 70 | 110 | 139 | 4.4 | 5.2 | 6.3 | 8.6 |
| T89-12 | 26 | 32 | 43 | 53 | 68 | 105 | 132 | 5.4 | 6.3 | 7.2 | 10.1 |
| T89-13 | 25 | 32 | 44 | 53 | 68 | 106 | 137 | 4.8 | 6.0 | 6.6 | 9.5 |
| T89-14 | 26 | 31 | 45 | 55 | 71 | 108 | 134 | 4.4 | 5.1 | 6.3 | 8.7 |
| T89-15 | 27 | 35 | 49 | 58 | 73 | 118 | 148 | 4.9 | 5.6 | 6.5 | 9.6 |
| T89-16 | 27 | 35 | 47 | 57 | 70 | 109 | 134 | 5.8 | 5.9 | 6.9 | 8.8 |
| T89-17 | 21 | 27 | 39 | 50 | 64 | 105 | 136 | 3.7 | 5.6 | 5.9 | 8.7 |
| T89-18 | 20 | 29 | 38 | 48 | 63 | 108 | 137 | 4.2 | 5.2 | 6.3 | 9.5 |
| T89-19 | 23 | 29 | 40 | 48 | 65 | 106 | 137 | 4.2 | 5.7 | 5.9 | 9.3 |
| T89-20 | 17 | 23 | 35 | 44 | 59 | 95 | 125 | 3.7 | 4.2 | 4.8 | 7.6 |
| T89-22 | 25 | 32 | 44 | 53 | 67 | 106 | 133 | 4.0 | 5.9 | 6.2 | 9.0 |
| T89-23 | 24 | 31 | 45 | 56 | 71 | 111 | 139 | 4.7 | 6.1 | 7.0 | 9.8 |

Construction Group KR224

Construct KR224 corresponding to EST A013P46U gene bank number A1162193. This gene is selected from data from Schrader et al 2004, and has its highest expression in sample 8 in the B series. This construct induces increased growth. This construction group shows an increased final height compared to the wild types when comparing the tallest individuals (11%). The construction group also shows an 11% increase in maximum height growth rate compared to the wild types when comparing the fastest growing individuals. The construction group meets growth Filter criteria (1) as shown in the below table 1.21.

Table 1.4a Growth data for KR224

| | Height (cm) Days in greenhouse | | | | | | | | | | |
|---|---|---|---|---|---|---|---|---|---|---|---|
| | 25 | 28 | 32 | 34 | 38 | 41 | 45 | 48 | 55 | 59 | 60 |
| KR224-1A | 28 | 31 | 39 | 42.5 | 52 | 61.5 | 74 | 82 | N/A | 117 | 120 |
| KR224-1B | 23 | 24.5 | 35 | 34.5 | 43 | 50.5 | 60 | 68 | 92 | 106 | 111 |
| KR224-2A | 31 | 36 | 45 | 49.5 | 61 | 72 | 87 | 95 | 126.5 | 140 | 147 |
| KR224-4A | 33 | 37.5 | 48 | 54 | 65 | 75 | 90 | 100 | 130 | N/A | 153 |
| KR224-5B | 28.5 | 34 | 42 | 47 | 57.5 | 66.5 | 79 | 87.5 | 114 | 125 | 128 |
| T89-23 | 28 | 34 | 42 | 47 | 55 | 63 | 76 | 83 | N/A | 82 | N/A |
| T89-24 | 29.5 | 33 | 42 | 47 | 55 | 65 | 75 | 83 | 108 | 120 | 125 |
| T89-25 | 31 | 35 | 45 | 50.5 | 60 | 68.5 | 80 | 89 | N/A | 128 | 132 |
| T89-26 | 28 | 32.5 | 41 | 46 | 56 | 65 | 79 | 88 | 115 | 126 | 132 |
| T89-27 | 29.5 | 34.5 | 43 | 47 | 56 | 66 | 79 | 86 | N/A | 127.5 | 132 |
| T89-28 | 28.5 | 33 | 42 | 46.5 | 56 | 64 | 76 | 86 | N/A | 125 | 130 |
| T89-29 | 31 | 35 | 42 | 49 | 57.5 | 67 | 80 | 89 | 118 | 131 | 137.5 |
| T89-30 | 26 | 29.5 | 38 | 43 | 52 | 58 | 70.5 | 78 | N/A | 116 | 120 |
| T89-31 | 25.5 | 31 | 38.5 | 43.5 | 53.5 | 62 | 74 | 82 | N/A | 123 | 128 |
| T89-32 | 28 | 33.5 | 41 | 47 | 56 | 64 | 78 | 87 | 113 | 128 | 134 |
| T89-33 | 27.5 | 29.5 | 37 | 42 | 50 | 56 | 67 | 73 | N/A | 72 | N/A |
| T89-34 | 29.5 | 34 | 43 | 47 | 56 | 66 | 73 | 81.5 | 112 | 123.5 | 129 |
| T89-35 | 16 | 19.5 | 25 | 28 | 35.5 | 42 | 52 | 58 | 80 | 90 | 94 |
| T89-36 | 25 | 30 | 36 | 44 | 53 | 62.5 | 74 | 82.5 | 110 | 124 | 129 |
| T89-37 | 16 | 19 | 27 | 30.5 | 38 | 45 | 53 | 58 | 80 | 92 | 96 |
| T89-38 | 24 | 29 | 37 | 41 | 51 | 60 | 73.5 | 81 | 108 | 122 | 129 |
| T89-39 | 26 | 30 | 40 | 45 | 55 | 64 | 79 | 88 | 116 | 130 | 137 |
| T89-40 | 28 | 32 | 39.5 | 44 | 52.5 | 61 | 73 | 81 | 108.5 | 124 | 129 |

-continued

| | | | | | | | | | | |
|---|---|---|---|---|---|---|---|---|---|---|
| T89-41 | 23 | 28 | 35 | 40.5 | 49 | 55 | 68 | 76 | 103 | 117 | 122 |

Table 1.4b Growth data for KR224

| | Diameter (mm) Days in greenhouse | | | | | | |
|---|---|---|---|---|---|---|---|
| | 28 | 32 | 38 | 45 | 55 | 59 | 60 |
| KR224-1A | 3.0 | 3.7 | 5.1 | 6.5 | N/A | 9.5 | 9.7 |
| KR224-1B | 2.7 | 2.6 | 3.5 | 5.3 | 7.5 | 8.0 | 8.4 |
| KR224-2A | 3.5 | 3.8 | 5.4 | 6.9 | 8.7 | N/A | 10.3 |
| KR224-4A | 3.4 | 3.9 | 5.0 | 6.7 | 8.5 | N/A | 9.6 |
| KR224-5B | 3.5 | 3.6 | 5.0 | 6.9 | 9.6 | 9.7 | 10.6 |
| T89-23 | 3.2 | 3.6 | 5.2 | 6.8 | N/A | N/A | N/A |
| T89-24 | 3.4 | 3.9 | 5.3 | 7.4 | 9.3 | 10.4 | 10.3 |
| T89-25 | 3.6 | 4.3 | 5.4 | 6.5 | N/A | 9.3 | 9.9 |
| T89-26 | 2.9 | 3.1 | 4.2 | 6.0 | 7.7 | N/A | 9.1 |
| T89-27 | 3.6 | 4.0 | 5.2 | 7.1 | N/A | 9.2 | 9.5 |
| T89-28 | 3.6 | 3.8 | 5.1 | 6.9 | N/A | 9.7 | 9.5 |
| T89-29 | 3.7 | 4.2 | 4.8 | 6.1 | 8.2 | 9.5 | 8.4 |
| T89-30 | 3.1 | 3.1 | 4.9 | 6.8 | N/A | 8.9 | 8.7 |
| T89-31 | 3.1 | 3.5 | 4.7 | 6.0 | N/A | N/A | 8.7 |
| T89-32 | 3.2 | 3.5 | 4.9 | 6.6 | 8.6 | N/A | 9.1 |
| T89-33 | 3.1 | 3.1 | 4.1 | 6.2 | N/A | N/A | N/A |
| T89-34 | 3.2 | 3.8 | 5.0 | 6.0 | 9.3 | 10.3 | 11.0 |
| T89-35 | 1.8 | 1.9 | 2.9 | 4.3 | 6.2 | 7.0 | 7.5 |
| T89-36 | 3.1 | 3.4 | 4.7 | 6.4 | 8.1 | N/A | 9.6 |
| T89-37 | 2.0 | 2.5 | 4.1 | 6.0 | 7.8 | 9.1 | 9.0 |
| T89-38 | 2.8 | 3.3 | 4.4 | 6.4 | 7.6 | N/A | 8.5 |
| T89-39 | 3.0 | 3.4 | 4.3 | 6.5 | 8.0 | N/A | 9.4 |
| T89-40 | 3.1 | 3.3 | 4.5 | 5.8 | 7.9 | N/A | 8.6 |
| T89-41 | 2.7 | 3.1 | 4.2 | 5.9 | 7.9 | N/A | 9.6 |

Construction Group KR240

Construct KR240 corresponding to EST A018P19U gene bank number A1162476. This gene is selected from the Hertzberg et al 2001 data and is up-regulated in the C and D zone. This construct induces increased growth. This construction group shows an increase in the diameter growth rate compared to the wild type controls of 20% when comparing the average values. The KR240 construction group meets Growth Filter criteria (3) and (4) as shown in the below table 1.21.

Construction Group KR292

Construct KR292 corresponding to EST A041P18U gene bank number A1163398. This gene is selected from the Schrader et al 2004 data and has its highest expression in samples 6-8 in the B series. This construct induces increased growth. This construction group shows an increased final width compared to the wild types when comparing the widest individuals of 14%. The construction group also shows a 15% increase in diameter growth rate compared to the wild types

TABLE 1.5

Growth data for KR240

| Days in greenhouse | Height (cm) | | | | | | | Diameter (mm) | | | | | |
|---|---|---|---|---|---|---|---|---|---|---|---|---|---|
| | 18 | 26 | 33 | 39 | 47 | 53 | 65 | 33 | 39 | 47 | 53 | 59 | 65 |
| KR240-1A-A | 20 | 34 | 50 | 80 | 98 | 117 | 161 | 5.2 | 7.3 | 7.9 | 9.0 | 9.3 | 9.6 |
| KR240-1A-B | 18 | 31 | 44 | 75 | 92 | 111 | 151 | 4.5 | 5.8 | 6.5 | 6.8 | 7.5 | 7.7 |
| KR240-2B | 19 | 32 | 47 | 76 | 90 | 108 | 147 | 5.0 | 6.6 | 7.3 | 8.7 | 8.8 | 9.0 |
| KR240-3B-A | 17 | 29 | 39 | 66 | 79 | 95 | 127 | 4.7 | 6.5 | 6.9 | 8.2 | 9.8 | 10.1 |
| KR240-5B-A | 16 | 30 | 46 | 76 | 92 | 108 | 146 | 4.6 | 6.1 | 7.0 | 7.5 | 8.2 | 9.0 |
| T89-133 | 23 | 37 | 51 | 84 | 103 | 121 | 156 | 4.7 | 6.7 | 7.7 | 8.4 | 9.1 | 9.7 |
| T89-134 | 25 | 38 | 50 | 80 | 95 | 112 | 149 | 4.4 | 6.2 | 7.1 | 7.6 | 7.6 | 8.4 |
| T89-135 | 17 | 29 | 43 | 71 | 86 | 104 | 140 | 4.8 | 6.6 | 7.7 | 8.6 | 9.1 | 9.1 |
| T89-136 | 19 | 31 | 45 | 72 | 85 | 103 | 138 | 4.6 | 5.3 | 6.0 | 6.4 | 7.3 | 7.8 |
| T89-137 | 22 | 37 | 52 | 82 | 96 | 112 | 151 | 5.0 | 6.5 | 7.3 | 7.8 | N/A | 10.0 |
| T89-138 | 21 | 33 | 47 | 78 | 94 | 109 | 140 | 4.9 | 6.0 | 7.0 | 7.8 | 8.4 | 9.0 |
| T89-139 | 24 | 39 | 56 | 92 | 108 | 124 | 159 | 4.8 | 5.7 | 6.3 | 7.0 | 7.6 | 8.4 |
| T89-140 | 25 | 41 | 56 | 88 | 101 | 115 | 148 | 4.9 | 6.0 | 6.0 | 6.8 | 7.0 | 7.8 |
| T89-141 | 17 | 30 | 45 | 77 | 87 | 104 | 132 | 5.0 | 5.3 | 6.2 | 6.4 | 6.9 | 7.2 |
| T89-142 | 24 | 38 | 54 | 85 | 99 | 116 | 146 | 5.3 | 5.9 | 6.3 | 6.6 | 7.6 | 8.3 |
| T89-143 | 24 | 40 | 56 | 89 | 107 | 122 | 155 | 4.7 | 5.7 | 6.3 | 6.8 | 7.3 | 8.4 |
| T89-144 | 23 | 37 | 52 | 76 | 89 | 107 | 139 | 4.5 | 5.9 | 6.5 | 6.9 | 7.1 | 7.9 |
| T89-146 | 27 | 43 | 58 | 84 | 99 | 116 | 153 | 4.6 | 6.0 | 6.7 | 7.4 | 7.8 | 8.5 |
| T89-147 | 26 | 44 | 62 | 95 | 111 | 130 | 167 | 5.4 | 6.5 | 6.9 | 7.4 | 8.0 | 8.7 |
| T89-148 | 21 | 32 | 47 | 77 | 91 | 109 | 146 | 4.2 | 5.4 | 6.1 | 6.6 | 6.9 | 7.8 | when comparing the fastest growing individuals. This construct induces meets Growth Filter criteria (2) as shown in the below table 1.21.

TABLE 1.6

Growth data for KR292

| Days in greenhouse | Height (cm) | | | | | | | Diameter (mm) | | | | |
|---|---|---|---|---|---|---|---|---|---|---|---|---|
| | 19 | 21 | 29 | 35 | 42 | 49 | 53 | 21 | 29 | 35 | 42 | 53 |
| KR292-1B | 27 | 32 | 51 | 69 | 98 | 131 | 147 | 3.4 | 5.0 | 6.0 | 7.6 | 8.2 |
| KR292-2B-A | 33 | 39 | 61 | 85 | 117 | 145 | 158 | 4.1 | 6.1 | 7.5 | 9.8 | 11.4 |
| KR292-2B-B | 28 | 33 | 55 | 77 | 109 | 138 | 152 | 3.5 | 5.7 | 7.2 | 9.0 | 10.7 |
| KR292-5A | 32 | 37 | 60 | 82 | 112 | 138 | 153 | 4.3 | 6.0 | 7.3 | 8.7 | 10.4 |
| T89-66 | 23 | 27 | 49 | 69 | 97 | 127 | 141 | 3.2 | 5.7 | 6.9 | 7.9 | 10.0 |
| T89-67 | 34 | 39 | 61 | 83.5 | 116 | 144 | 159 | 4.1 | 5.4 | 6.7 | 8.0 | 9.7 |
| T89-68 | 27 | 32 | 51 | 69 | 99 | 129 | 143 | 3.4 | 4.8 | 5.9 | 7.9 | 9.5 |
| T89-69 | 35 | 40 | 61 | 81 | N/A | 136 | 153 | 3.6 | 5.4 | 6.8 | N/A | 9.0 |
| T89-70 | 29 | 32 | 51 | 68 | 97 | 125 | 140 | 3.1 | 4.7 | 5.7 | 7.5 | 8.6 |
| T89-71 | 29 | 44 | 55 | 74 | 107 | 135 | 148 | 3.4 | 4.9 | 6.6 | 7.6 | 9.0 |
| T89-72 | 33 | 38 | 57 | 75 | 102 | 129 | 145 | 3.2 | 4.7 | 6.0 | 8.0 | 9.3 |
| T89-73 | 34 | 40 | 59 | 78 | 106 | 132 | 149 | 3.5 | 5.7 | 6.2 | 8.2 | 9.5 |

Construction Group KR313

Construct KR313 corresponding to EST A047P40U gene bank number A1163745. This gene is selected from the Schrader et al 2004 data and has its highest expression in samples 8-10 in the B series, in the Hertzberg et al 2001 data the gene has its highest expression in the B sample. This construct induces increased growth. This construct induces a 20% increased maximum height growth speed. This construct meets Growth Filter criterion (4) as shown in the below table 1.21.

TABLE 1.7

Growth data for KR313

| | Height (cm) | | | | | | | Diameter (mm) | | | | |
|---|---|---|---|---|---|---|---|---|---|---|---|---|
| | Days in greenhouse | | | | | | | | | | | |
| | 19 | 21 | 29 | 35 | 42 | 49 | 53 | 21 | 29 | 35 | 42 | 53 |
| KR313-2B | 29 | 35 | 53 | 73 | 103 | 131 | 147 | 3.2 | 4.5 | 6.1 | 6.9 | 8.3 |
| KR313-6B | 20 | 25 | 49 | 70 | 107 | 142 | 161 | 2.8 | 3.8 | 5.3 | 7.7 | 9.9 |
| KR313-7B | 26 | 31 | 54 | 75 | 105 | 136 | 151 | 3.8 | 5.0 | 6.2 | 7.9 | 10.1 |
| KR313-9A | 15 | 19 | 37 | 56 | 84 | 110 | 126 | 2.2 | 3.2 | 4.5 | 6.6 | 8.6 |
| KR313-9B | 21 | 26 | 48 | 68 | 98 | 134 | 151 | 3.1 | 4.0 | 5.4 | 7.7 | 9.5 |
| T89-66 | 23 | 27 | 49 | 69 | 97 | 127 | 141 | 3.2 | 5.7 | 6.9 | 7.9 | 10.0 |
| T89-67 | 34 | 39 | 61 | 83.5 | 116 | 144 | 159 | 4.1 | 5.4 | 6.7 | 8.0 | 9.7 |
| T89-68 | 27 | 32 | 51 | 69 | 99 | 129 | 143 | 3.4 | 4.8 | 5.9 | 7.9 | 9.5 |
| T89-69 | 35 | 40 | 61 | 81 | N/A | 136 | 153 | 3.6 | 5.4 | 6.8 | N/A | 9.0 |
| T89-70 | 29 | 32 | 51 | 68 | 97 | 125 | 140 | 3.1 | 4.7 | 5.7 | 7.5 | 8.6 |
| T89-71 | 29 | 44 | 55 | 74 | 107 | 135 | 148 | 3.4 | 4.9 | 6.6 | 7.6 | 9.0 |
| T89-72 | 33 | 38 | 57 | 75 | 102 | 129 | 145 | 3.2 | 4.7 | 6.0 | 8.0 | 9.3 |

Construction Group KR459

Construct KR459 corresponding to EST UB12CPEO3 gene bank number BU820650. This gene is selected from the Schrader et al 2004 data and has its highest expression in sample 6 in the B series. This construct induces increased growth. This construct induces increased height growth, the final height is 24% and the maximum height growth rate is 23% larger comparing the fastest growing individuals from the construction group and wild type control group. This construct meets Growth Filter criteria (4) as shown in the below table 1.21.

TABLE 1.8

Growth data for KR459

| | Height (cm) | | | | | | Diameter (mm) | | | | | |
|---|---|---|---|---|---|---|---|---|---|---|---|---|
| | Days in greenhouse | | | | | | | | | | | |
| | 21 | 28 | 34 | 40 | 49 | 61 | 21 | 28 | 34 | 40 | 49 | 61 |
| KR459-3B | 27 | 42 | 59 | 79 | 128 | 146 | 3.1 | 4.3 | 6.4 | 7.9 | 9.9 | 10.9 |
| KR459-4B | 28 | 42 | 58 | 78 | 127 | 160 | 3.3 | 4.6 | 6.3 | 7.0 | 8.9 | 10.5 |
| KR459-5B | 25 | 40 | 57 | 76 | 125 | 158 | 3.3 | 4.1 | 6.4 | 7.8 | 9.3 | 10.5 |
| KR459-6A | 31 | 48 | 72 | 104 | 167 | 207 | 3.2 | 4.6 | 6.6 | 8.3 | 10.5 | 11.0 |
| KR459-7A | 28 | 42 | 62 | 83 | 136 | 170 | 3.1 | 4.5 | 6.4 | 7.9 | 9.3 | 10.8 |
| T89-1 | 26 | 39 | 56 | 74 | 120 | 150 | 3.3 | 3.7 | 6.7 | 7.5 | 9.7 | 11.4 |
| T89-2 | 24 | 40 | 62 | 85 | 132 | 159 | 3.0 | 4.4 | 6.9 | 7.9 | 10.4 | 11.5 |
| T89-3 | 24 | 37 | 54 | 75 | 127 | 158 | 2.8 | 3.7 | 6.4 | 7.1 | 8.9 | 10.3 |
| T89-4 | 24 | 37 | 54 | 79 | 126 | 151 | 2.9 | 4.0 | 6.0 | 7.2 | 9.4 | 11.2 |
| T89-5 | 20 | 34 | 52 | 76 | 125 | 155 | 2.8 | 3.5 | 6.0 | 7.2 | 9.6 | 11.0 |
| T89-6 | 26 | 40 | 56 | 76 | 121 | 149 | 3.2 | 3.8 | 6.2 | 7.9 | 10.3 | 11.4 |
| T89-7 | 25 | 40 | 60 | 86 | 137 | 167 | 3.0 | 4.8 | 6.1 | 7.6 | 9.7 | 10.3 |
| T89-8 | 26 | 41 | 59 | 81 | 129 | 150 | 3.3 | 4.5 | 6.9 | 8.1 | 10.7 | 11.9 |
| T89-9 | 26 | 39 | 56 | 78 | 129 | 160 | 3.2 | 4.4 | 6.3 | 7.9 | 10.2 | 10.8 |
| T89-10 | 26 | 39 | 58 | 84 | 134 | 166 | 2.8 | 4.1 | 5.8 | 7.5 | 9.2 | 9.7 |

Construction Group KR463

Construct KR463 corresponding to EST UB24CPA08 gene bank number CK106533. This gene is selected from the Schrader et al 2004 data and has its highest expression in sample 6 in the B series. This construct induces increased growth. This construction group shows an 18% increase in the average diameter growth rate compared to the wild type control trees. This construct meets Growth Filter criteria (3) and (4) as shown in the below table 1.21.

TABLE 1.9

Growth data for KR463

| | Height (cm) | | | | | | | Diameter (mm) | | | | |
|---|---|---|---|---|---|---|---|---|---|---|---|---|
| | Days in greenhouse | | | | | | | | | | | |
| | 18 | 26 | 33 | 39 | 47 | 53 | 65 | 33 | 39 | 47 | 53 | 59 | 65 |
| KR463-1A | 22 | 35 | 49 | 79 | 93 | 110 | 143 | 2.9 | 6.3 | 5.9 | 6.6 | 7.6 | 8.7 |
| KR463-2A | 23 | 35 | 50 | 78 | 92 | 107 | 148 | 4.2 | 5.4 | 5.8 | 6.6 | 6.9 | 7.5 |
| KR463-2B | 23 | 37 | 52 | 83 | 99 | 115 | 150 | 5.1 | 6.4 | 6.7 | 7.4 | 8.4 | 9.1 |
| KR463-4A | 24 | 40 | 56 | N/A | 108 | 129 | 163 | 5.2 | N/A | 8.0 | 9.0 | 9.8 | 10.6 |
| KR463-4B | 23 | 38 | 54 | 81 | 95 | 112 | 152 | 4.6 | 6.4 | 6.8 | 7.6 | 7.9 | 8.3 |
| T89-133 | 23 | 37 | 51 | 84 | 103 | 121 | 156 | 4.7 | 6.7 | 7.7 | 8.4 | 9.1 | 9.7 |
| T89-134 | 25 | 38 | 50 | 80 | 95 | 112 | 149 | 4.4 | 6.2 | 7.1 | 7.6 | 7.6 | 8.4 |
| T89-135 | 17 | 29 | 43 | 71 | 86 | 104 | 140 | 4.8 | 6.6 | 7.7 | 8.6 | 9.1 | 9.1 |
| T89-136 | 19 | 31 | 45 | 72 | 85 | 103 | 138 | 4.6 | 5.3 | 6.0 | 6.4 | 7.3 | 7.8 |
| T89-137 | 22 | 37 | 52 | 82 | 96 | 112 | 151 | 5.0 | 6.5 | 7.3 | 7.8 | N/A | 10.0 |
| T89-138 | 21 | 33 | 47 | 78 | 94 | 109 | 140 | 4.9 | 6.0 | 7.0 | 7.8 | 8.4 | 9.0 |
| T89-139 | 24 | 39 | 56 | 92 | 108 | 124 | 159 | 4.8 | 5.7 | 6.3 | 7.0 | 7.6 | 8.4 |
| T89-140 | 25 | 41 | 56 | 88 | 101 | 115 | 148 | 4.9 | 6.0 | 6.0 | 6.8 | 7.0 | 7.8 |
| T89-141 | 17 | 30 | 45 | 77 | 87 | 104 | 132 | 5.0 | 5.3 | 6.2 | 6.4 | 6.9 | 7.2 |
| T89-142 | 24 | 38 | 54 | 85 | 99 | 116 | 146 | 5.3 | 5.9 | 6.3 | 6.6 | 7.6 | 8.3 |
| T89-143 | 24 | 40 | 56 | 89 | 107 | 122 | 155 | 4.7 | 5.7 | 6.3 | 6.8 | 7.3 | 8.4 |
| T89-144 | 23 | 37 | 52 | 76 | 89 | 107 | 139 | 4.5 | 5.9 | 6.5 | 6.9 | 7.1 | 7.9 |
| T89-146 | 27 | 43 | 58 | 84 | 99 | 116 | 153 | 4.6 | 6.0 | 6.7 | 7.4 | 7.8 | 8.5 |
| T89-147 | 26 | 44 | 62 | 95 | 111 | 130 | 167 | 5.4 | 6.5 | 6.9 | 7.4 | 8.0 | 8.7 |
| T89-148 | 21 | 32 | 47 | 77 | 91 | 109 | 146 | 4.2 | 5.4 | 6.1 | 6.6 | 6.9 | 7.8 |

Construction Group KR465

Construct KR465 corresponding to EST UB29DPEO2 gene bank number CK106678. This gene is selected from the Schrader et al 2004 data and is highest expression in sample 9 in the B series. This construct induces increased growth. This construction group shows a 23% increase in the diameter growth rate. This construct meets Growth Filter criterion (3) as shown in the below table 1.21.

TABLE 1.10

| | Height (cm) | | | | | | | Diameter (mm) | | | | | |
|---|---|---|---|---|---|---|---|---|---|---|---|---|---|
| | Days in greenhouse | | | | | | | | | | | | |
| | 18 | 26 | 33 | 39 | 47 | 53 | 65 | 33 | 39 | 47 | 53 | 59 | 65 |
| KR465-1A | 13 | 28 | 47 | 81 | 98 | 119 | 158 | 3.9 | 5.3 | 6.2 | 7.5 | 8.0 | 9.3 |
| KR465-1B | 20 | 29 | 40 | 69 | 84 | 102 | 143 | 3.2 | 4.7 | 5.6 | 6.4 | 7.4 | 7.7 |
| KR465-2A-B | 10 | 22 | 36 | N/A | 88 | 107 | 147 | 4.0 | N/A | 6.3 | 7.2 | 7.7 | 8.3 |
| KR465-2B | 22 | 33 | 50 | 80 | 94 | 109 | 140 | 4.2 | 5.4 | 5.8 | 6.1 | 6.8 | 7.1 |
| KR465-3A | 26 | 41 | 57 | 93 | 107 | 122 | 154 | 4.6 | 5.6 | 6.4 | 7.6 | 7.7 | 8.2 |
| KR465-4B-B | 16 | 30 | 47 | 83 | 100 | 118 | 162 | 4.0 | 6.0 | 6.9 | 7.9 | 9.2 | 9.3 |
| T89-133 | 23 | 37 | 51 | 84 | 103 | 121 | 156 | 4.7 | 6.7 | 7.7 | 8.4 | 9.1 | 9.7 |
| T89-134 | 25 | 38 | 50 | 80 | 95 | 112 | 149 | 4.4 | 6.2 | 7.1 | 7.6 | 7.6 | 8.4 |
| T89-135 | 17 | 29 | 43 | 71 | 86 | 104 | 140 | 4.8 | 6.6 | 7.7 | 8.6 | 9.1 | 9.1 |
| T89-136 | 19 | 31 | 45 | 72 | 85 | 103 | 138 | 4.6 | 5.3 | 6.0 | 6.4 | 7.3 | 7.8 |
| T89-137 | 22 | 37 | 52 | 82 | 96 | 112 | 151 | 5.0 | 6.5 | 7.3 | 7.8 | N/A | 10.0 |
| T89-138 | 21 | 33 | 47 | 78 | 94 | 109 | 140 | 4.9 | 6.0 | 7.0 | 7.8 | 8.4 | 9.0 |
| T89-139 | 24 | 39 | 56 | 92 | 108 | 124 | 159 | 4.8 | 5.7 | 6.3 | 7.0 | 7.6 | 8.4 |
| T89-140 | 25 | 41 | 56 | 88 | 101 | 115 | 148 | 4.9 | 6.0 | 6.0 | 6.8 | 7.0 | 7.8 |
| T89-141 | 17 | 30 | 45 | 77 | 87 | 104 | 132 | 5.0 | 5.3 | 6.2 | 6.4 | 6.9 | 7.2 |
| T89-142 | 24 | 38 | 54 | 85 | 99 | 116 | 146 | 5.3 | 5.9 | 6.3 | 6.6 | 7.6 | 8.3 |
| T89-143 | 24 | 40 | 56 | 89 | 107 | 122 | 155 | 4.7 | 5.7 | 6.3 | 6.8 | 7.3 | 8.4 |
| T89-144 | 23 | 37 | 52 | 76 | 89 | 107 | 139 | 4.5 | 5.9 | 6.5 | 6.9 | 7.1 | 7.9 |
| T89-146 | 27 | 43 | 58 | 84 | 99 | 116 | 153 | 4.6 | 6.0 | 6.7 | 7.4 | 7.8 | 8.5 |
| T89-147 | 26 | 44 | 62 | 95 | 111 | 130 | 167 | 5.4 | 6.5 | 6.9 | 7.4 | 8.0 | 8.7 |
| T89-148 | 21 | 32 | 47 | 77 | 91 | 109 | 146 | 4.2 | 5.4 | 6.1 | 6.6 | 6.9 | 7.8 |

Construction Group KR121

Construct KR121 corresponding to EST A043P46U gene bank number A1163516. This gene is selected from the Hertzberg et al 2001 data and is down-regulated in the E zone. This construct induces increased growth. This construction group shows an increased final height, final diameter, final maximum height growth rate and diameter growth rate of 14%, 16%, 9%, 15% respectively as compared to the wt control trees. This construct meets Growth Filter criteria (2), and (3) as shown in the below table 1.21.

Table 1.11a Growth data for KR121

| | Height (cm) | | | | | | | | | | |
|---|---|---|---|---|---|---|---|---|---|---|---|
| | Days in greenhouse | | | | | | | | | | |
| | 25 | 28 | 32 | 34 | 38 | 41 | 45 | 48 | 55 | 59 | 60 |
| KR121-1A | 35 | 40 | 50 | 56 | 67 | 76 | 91 | 100 | 130 | 145 | 150 |
| KR121-1B | 31 | 36 | 45 | 51 | 62 | 70 | 85 | 96.5 | 127 | 141 | 147.5 |
| KR121-4B | 31.5 | 37 | 47.5 | 53 | 63.5 | 73 | 90 | 100 | N/A | 135 | 140 |
| KR121-5A | 32 | 37 | 46 | 52 | 60 | 69 | 81 | 92 | N/A | 132.5 | 138 |
| KR121-5B | 29.5 | 34.5 | 44 | 49 | 60 | 70 | 85 | 93.5 | N/A | 132 | 137.5 |
| T89-23 | 28 | 34 | 42 | 47 | 55 | 63 | 76 | 83 | N/A | 82 | N/A |
| T89-24 | 29.5 | 33 | 42 | 47 | 55 | 65 | 75 | 83 | 108 | 120 | 125 |
| T89-25 | 31 | 35 | 45 | 50.5 | 60 | 68.5 | 80 | 89 | N/A | 128 | 132 |
| T89-26 | 28 | 32.5 | 41 | 46 | 56 | 65 | 79 | 88 | 115 | 126 | 132 |
| T89-27 | 29.5 | 34.5 | 43 | 47 | 56 | 66 | 79 | 86 | N/A | 127.5 | 132 |
| T89-28 | 28.5 | 33 | 42 | 46.5 | 56 | 64 | 76 | 86 | N/A | 125 | 130 |
| T89-29 | 31 | 35 | 42 | 49 | 57.5 | 67 | 80 | 89 | 118 | 131 | 137.5 |
| T89-30 | 26 | 29.5 | 38 | 43 | 52 | 58 | 70.5 | 78 | N/A | 116 | 120 |
| T89-31 | 25.5 | 31 | 38.5 | 43.5 | 53.5 | 62 | 74 | 82 | N/A | 123 | 128 |
| T89-32 | 28 | 33.5 | 41 | 47 | 56 | 64 | 78 | 87 | 113 | 128 | 134 |
| T89-33 | 27.5 | 29.5 | 37 | 42 | 50 | 56 | 67 | 73 | N/A | 72 | N/A |
| T89-34 | 29.5 | 34 | 43 | 47 | 56 | 66 | 73 | 81.5 | 112 | 123.5 | 129 |
| T89-35 | 16 | 19.5 | 25 | 28 | 35.5 | 42 | 52 | 58 | 80 | 90 | 94 |
| T89-36 | 25 | 30 | 36 | 44 | 53 | 62.5 | 74 | 82.5 | 110 | 124 | 129 |
| T89-37 | 16 | 19 | 27 | 30.5 | 38 | 45 | 53 | 58 | 80 | 92 | 96 |
| T89-38 | 24 | 29 | 37 | 41 | 51 | 60 | 73.5 | 81 | 108 | 122 | 129 |
| T89-39 | 26 | 30 | 40 | 45 | 55 | 64 | 79 | 88 | 116 | 130 | 137 |
| T89-40 | 28 | 32 | 39.5 | 44 | 52.5 | 61 | 73 | 81 | 108.5 | 124 | 129 |
| T89-41 | 23 | 28 | 35 | 40.5 | 49 | 55 | 68 | 76 | 103 | 117 | 122 |

Table 1.11b Growth data for KR121

| | Diameter (mm) Days in greenhouse | | | | | | |
|---|---|---|---|---|---|---|---|
| | 28 | 32 | 38 | 45 | 55 | 59 | 60 |
| KR121-1A | 3.6 | 4.1 | 5.2 | 7.1 | 9.0 | N/A | 10.1 |
| KR121-1B | 3.4 | 3.9 | 5.4 | 6.7 | 8.8 | N/A | 10.2 |
| KR121-4B | 3.6 | 4.3 | 6.0 | 8.2 | N/A | 12.0 | 12.0 |
| KR121-5A | 3.4 | 4.2 | 5.0 | 7.1 | N/A | 10.5 | 10.6 |
| KR121-5B | 3.2 | 4.0 | 5.5 | 7.4 | N/A | 10.1 | 10.4 |
| T89-23 | 3.2 | 3.6 | 5.2 | 6.8 | N/A | N/A | N/A |
| T89-24 | 3.4 | 3.9 | 5.3 | 7.4 | 9.3 | 10.4 | 10.3 |
| T89-25 | 3.6 | 4.3 | 5.4 | 6.5 | N/A | 9.3 | 9.9 |
| T89-26 | 2.9 | 3.1 | 4.2 | 6.0 | 7.7 | N/A | 9.1 |
| T89-27 | 3.6 | 4.0 | 5.2 | 7.1 | N/A | 9.2 | 9.5 |
| T89-28 | 3.6 | 3.8 | 5.1 | 6.9 | N/A | 9.7 | 9.5 |
| T89-29 | 3.7 | 4.2 | 4.8 | 6.1 | 8.2 | 9.5 | 8.4 |
| T89-30 | 3.1 | 3.1 | 4.9 | 6.8 | N/A | 8.9 | 8.7 |
| T89-31 | 3.1 | 3.5 | 4.7 | 6.0 | N/A | N/A | 8.7 |
| T89-32 | 3.2 | 3.5 | 4.9 | 6.6 | N/A | 8.6 | 9.1 |
| T89-33 | 3.1 | 3.1 | 4.1 | 6.2 | N/A | N/A | N/A |
| T89-34 | 3.2 | 3.8 | 5.0 | 6.0 | 9.3 | 10.3 | 11.0 |
| T89-35 | 1.8 | 1.9 | 2.9 | 4.3 | 6.2 | 7.0 | 7.5 |
| T89-36 | 3.1 | 3.4 | 4.7 | 6.4 | 8.1 | N/A | 9.6 |
| T89-37 | 2.0 | 2.5 | 4.1 | 6.0 | 7.8 | 9.1 | 9.0 |
| T89-38 | 2.8 | 3.3 | 4.4 | 6.4 | 7.6 | N/A | 8.5 |
| T89-39 | 3.0 | 3.4 | 4.3 | 6.5 | 8.0 | N/A | 9.4 |
| T89-40 | 3.1 | 3.3 | 4.5 | 5.8 | 7.9 | N/A | 8.6 |
| T89-41 | 2.7 | 3.1 | 4.2 | 5.9 | 7.9 | N/A | 9.6 |

Construction Group KR125

Construct KR125 corresponding to EST A045P41U gene bank number A1163624. This gene is selected from the Hertzberg et al 2001 data and is up-regulated in the D zone. This construct induces increased growth. This construct shows an increased final diameter and increased diameter growth rate of 12 and 6% respectively. This construct meets Growth Filter criterion (2) as shown in the below table 1.21.

TABLE 1.12

Growth data for KR125

| | Height (cm) | | | | | | Diameter (mm) | | | |
|---|---|---|---|---|---|---|---|---|---|---|
| | Days in greenhouse | | | | | | | | | |
| | 25 | 35 | 40 | 42 | 50 | 57 | 35 | 42 | 50 | 57 |
| KR125-4A-1 | 41.5 | 70 | 89 | 96 | 123 | 149 | 6.4 | 8.0 | 8.5 | 9.4 |
| KR125-4A-2 | 40 | 67 | 86 | 95 | 128 | 153 | 5.7 | 6.6 | 7.8 | 9.1 |
| KR125-5A-1 | 40.5 | 66 | 85 | 94 | 125 | 152 | 5.9 | 7.2 | 8.3 | 9.5 |
| KR125-6A-1 | 37 | 64 | 83 | 90 | 118 | 143 | 5.4 | 7.1 | 8.3 | 9.1 |
| KR125-6A-2 | 43 | 69 | 89 | 98 | 129 | 156 | 6.0 | 7.3 | 9.0 | 10.3 |
| T89-44 | 35 | 60 | 79 | 85 | 115 | 139 | 4.5 | 5.4 | 5.9 | 6.9 |
| T89-47 | 33 | 61 | 79 | 88 | 121 | 147 | 5.3 | 6.5 | 8.1 | 9.2 |
| T89-49 | 33.5 | 57 | 76 | 85 | 115 | 143 | 5.3 | 6.4 | 8.1 | 9.3 |
| T89-53 | 35 | 58 | 76 | 82 | 115 | 140 | 5.7 | 6.8 | 7.3 | 8.7 |
| T89-57 | 33 | 55 | 71 | 78 | 107 | 137 | 5.0 | 6.6 | 7.3 | 8.0 |
| T89-58E-1 | 28 | 50 | 62 | 68 | 92 | 120 | 4.6 | 5.8 | 7.5 | 7.4 |

TABLE 1.12-continued

Growth data for KR125

| | Height (cm) | | | | | | Diameter (mm) | | | |
|---|---|---|---|---|---|---|---|---|---|---|
| | Days in greenhouse | | | | | | | | | |
| | 25 | 35 | 40 | 42 | 50 | 57 | 35 | 42 | 50 | 57 |
| T89-58E-2 | 28 | 51 | 71 | 79 | 113 | 139 | 5.0 | 6.9 | 7.5 | 8.5 |
| T89-59E-1 | 26.5 | 51.5 | 71 | 78 | 108 | 138 | 4.8 | 6.5 | 7.9 | 8.4 |
| T89-60E-1 | 31.5 | 56 | 76 | 84 | 114 | 137 | 5.2 | 6.6 | 8.0 | 8.9 |
| T89-60E-2 | 34 | 57 | 75 | 83 | 110 | 134 | 5.4 | 7.0 | 8.4 | 9.5 |
| T89-61E-1 | 27 | 48 | 65 | 72 | 102 | 133 | 4.4 | 5.6 | 7.0 | 6.9 |
| T89-61E-2 | 29 | 52 | 70 | 80 | 111 | 139 | 5.0 | 6.2 | 7.5 | 8.4 |
| T89-62 | 30 | 55 | 72 | 79 | 112 | 140 | 5.2 | 6.4 | 7.7 | 8.9 |
| T89-63 | 30 | 55 | 72 | 80 | 110 | 133 | 5.4 | 6.3 | 6.8 | 8.7 |
| T89-64 | 34 | 59 | 77 | 85 | 113 | 139 | 5.2 | 6.8 | 7.4 | 8.5 |
| T89-65 | 36 | 64 | 82 | 90 | 120 | 148 | 5.9 | 7.2 | 8.9 | 9.8 |

Construction Group KR140

Construct KR140 corresponding to EST A061P49U gene bank number A1164435. This gene is selected from the Hertzberg et al 2001 data and is up-regulated in the D zone. This construct induces increased growth. This construct induces increased height growth, the maximum height growth rate is 12% larger comparing the average of the construction group and wild type control group. This construct meets Growth Filter criteria (1) as shown in the below table 1.21.

Table 1.13a Growth data for KR140

| | Height (cm) Days in greenhouse | | | | | | | | | | |
|---|---|---|---|---|---|---|---|---|---|---|---|
| | 25 | 28 | 32 | 34 | 38 | 41 | 45 | 48 | 55 | 59 | 60 |
| KR140-1A | 34 | 37.5 | 49 | 54 | 66 | N/A | 91.5 | 100 | 130 | 145 | 151 |
| KR140-2A | 26.5 | 30 | 38 | 44 | 54 | 64 | 78 | 87 | 117 | 132 | 139 |
| KR140-4A | 20 | 22 | 30 | 35 | 44 | 52 | 64.5 | 73 | 102 | 116 | 122.5 |
| KR140-5A | 15 | 18.5 | 23 | 27 | 36.5 | 44 | 54 | 62.5 | 89 | 101 | 107 |

-continued

| | | | | | | | | | | | |
|---|---|---|---|---|---|---|---|---|---|---|---|
| KR140-5B | 35 | 40 | 49 | 55 | 66.5 | 74 | 89 | 99 | 127.5 | 142 | 149 |
| T89-23 | 28 | 34 | 42 | 47 | 55 | 63 | 76 | 83 | N/A | 82 | N/A |
| T89-24 | 29.5 | 33 | 42 | 47 | 55 | 65 | 75 | 83 | 108 | 120 | 125 |
| T89-25 | 31 | 35 | 45 | 50.5 | 60 | 68.5 | 80 | 89 | N/A | 128 | 132 |
| T89-26 | 28 | 32.5 | 41 | 46 | 56 | 65 | 79 | 88 | 115 | 126 | 132 |
| T89-27 | 29.5 | 34.5 | 43 | 47 | 56 | 66 | 79 | 86 | N/A | 127.5 | 132 |
| T89-28 | 28.5 | 33 | 42 | 46.5 | 56 | 64 | 76 | 86 | N/A | 125 | 130 |
| T89-29 | 31 | 35 | 42 | 49 | 57.5 | 67 | 80 | 89 | 118 | 131 | 137.5 |
| T89-30 | 26 | 29.5 | 38 | 43 | 52 | 58 | 70.5 | 78 | N/A | 116 | 120 |
| T89-31 | 25.5 | 31 | 38.5 | 43.5 | 53.5 | 62 | 74 | 82 | N/A | 123 | 128 |
| T89-32 | 28 | 33.5 | 41 | 47 | 56 | 64 | 78 | 87 | 113 | 128 | 134 |
| T89-33 | 27.5 | 29.5 | 37 | 42 | 50 | 56 | 67 | 73 | N/A | 72 | N/A |
| T89-34 | 29.5 | 34 | 43 | 47 | 56 | 66 | 73 | 81.5 | 112 | 123.5 | 129 |
| T89-35 | 16 | 19.5 | 25 | 28 | 35.5 | 42 | 52 | 58 | 80 | 90 | 94 |
| T89-36 | 25 | 30 | 36 | 44 | 53 | 62.5 | 74 | 82.5 | 110 | 124 | 129 |
| T89-37 | 16 | 19 | 27 | 30.5 | 38 | 45 | 53 | 58 | 80 | 92 | 96 |
| T89-38 | 24 | 29 | 37 | 41 | 51 | 60 | 73.5 | 81 | 108 | 122 | 129 |
| T89-39 | 26 | 30 | 40 | 45 | 55 | 64 | 79 | 88 | 116 | 130 | 137 |
| T89-40 | 28 | 32 | 39.5 | 44 | 52.5 | 61 | 73 | 81 | 108.5 | 124 | 129 |
| T89-41 | 23 | 28 | 35 | 40.5 | 49 | 55 | 68 | 76 | 103 | 117 | 122 |

Table 1.13b Growth data for KR140

| | Diameter (mm) Days in greenhouse | | | | | | |
|---|---|---|---|---|---|---|---|
| | 28 | 32 | 38 | 45 | 55 | 59 | 60 |
| KR140-1A | 4.0 | 4.5 | 5.7 | 6.9 | 8.8 | N/A | 10.0 |
| KR140-2A | 2.7 | 3.3 | 4.8 | 6.0 | 7.9 | N/A | 8.8 |
| KR140-4A | 2.8 | 3.2 | 4.3 | 6.0 | 7.9 | N/A | 9.2 |
| KR140-5A | 1.6 | 2.0 | 3.1 | 4.5 | 6.7 | N/A | 7.7 |
| KR140-5B | 3.7 | 4.3 | 5.4 | 7.5 | 9.2 | N/A | 10.1 |
| T89-23 | 3.2 | 3.6 | 5.2 | 6.8 | N/A | N/A | N/A |
| T89-24 | 3.4 | 3.9 | 5.3 | 7.4 | 9.3 | 10.4 | 10.3 |
| T89-25 | 3.6 | 4.3 | 5.4 | 6.5 | N/A | 9.3 | 9.9 |
| T89-26 | 2.9 | 3.1 | 4.2 | 6.0 | 7.7 | N/A | 9.1 |
| T89-27 | 3.6 | 4.0 | 5.2 | 7.1 | N/A | 9.2 | 9.5 |
| T89-28 | 3.6 | 3.8 | 5.1 | 6.9 | N/A | 9.7 | 9.5 |
| T89-29 | 3.7 | 4.2 | 4.8 | 6.1 | 8.2 | 9.5 | 8.4 |
| T89-30 | 3.1 | 3.1 | 4.9 | 6.8 | N/A | 8.9 | 8.7 |
| T89-31 | 3.1 | 3.5 | 4.7 | 6.0 | N/A | N/A | 8.7 |
| T89-32 | 3.2 | 3.5 | 4.9 | 6.6 | 8.6 | N/A | 9.1 |
| T89-33 | 3.1 | 3.1 | 4.1 | 6.2 | N/A | N/A | N/A |
| T89-34 | 3.2 | 3.8 | 5.0 | 6.0 | 9.3 | 10.3 | 11.0 |
| T89-35 | 1.8 | 1.9 | 2.9 | 4.3 | 6.2 | 7.0 | 7.5 |
| T89-36 | 3.1 | 3.4 | 4.7 | 6.4 | 8.1 | N/A | 9.6 |
| T89-37 | 2.0 | 2.5 | 4.1 | 6.0 | 7.8 | 9.1 | 9.0 |
| T89-38 | 2.8 | 3.3 | 4.4 | 6.4 | 7.6 | N/A | 8.5 |
| T89-39 | 3.0 | 3.4 | 4.3 | 6.5 | 8.0 | N/A | 9.4 |
| T89-40 | 3.1 | 3.3 | 4.5 | 5.8 | 7.9 | N/A | 8.6 |
| T89-41 | 2.7 | 3.1 | 4.2 | 5.9 | 7.9 | N/A | 9.6 |

Construction Group KR152

Construct KR152 corresponding to EST A077P51U gene bank number A1165178. This gene is selected from the Hertzberg et al 2001 data and is down-regulated in the E zone. This construct induces increased growth. This construct induces increased height growth, the final height is 10% and the maximum height growth rate is 11% larger comparing the average of the construction group and wild type control group. This construct induct meets Growth Filter criteria (1) as shown in the below table 1.21.

Table 1.14a Growth data for KR152

| | Height (cm) Days in greenhouse | | | | | | | | | | |
|---|---|---|---|---|---|---|---|---|---|---|---|
| | 25 | 28 | 32 | 34 | 38 | 41 | 45 | 48 | 55 | 59 | 60 |
| KR152-1B | 26 | 30 | 37.5 | 42.5 | 54 | 63 | 76 | 87 | 117 | 135 | 137 |
| KR152-2B | 24 | 28.5 | 38 | 43 | 53 | 61.5 | 74 | 82 | 112 | 126 | 130 |
| KR152-3B | 32.5 | 38 | 48 | 54 | 60 | 73 | 87 | 93 | N/A | 91 | N/A |
| KR152-4A | 28.5 | 33 | 41 | 45 | 53.5 | 64 | 76 | 85 | N/A | 124 | 137 |
| KR152-4B | 29 | N/A | 42 | 46 | 58 | 68 | 81 | 89.5 | 117 | 132 | 136 |
| T89-23 | 28 | 34 | 42 | 47 | 55 | 63 | 76 | 83 | N/A | 82 | N/A |
| T89-24 | 29.5 | 33 | 42 | 47 | 55 | 65 | 75 | 83 | 108 | 120 | 125 |
| T89-25 | 31 | 35 | 45 | 50.5 | 60 | 68.5 | 80 | 89 | N/A | 128 | 132 |
| T89-26 | 28 | 32.5 | 41 | 46 | 56 | 65 | 79 | 88 | 115 | 126 | 132 |

-continued

| | | | | | | | | | | | |
|---|---|---|---|---|---|---|---|---|---|---|---|
| T89-27 | 29.5 | 34.5 | 43 | 47 | 56 | 66 | 79 | 86 | N/A | 127.5 | 132 |
| T89-28 | 28.5 | 33 | 42 | 46.5 | 56 | 64 | 76 | 86 | N/A | 125 | 130 |
| T89-29 | 31 | 35 | 42 | 49 | 57.5 | 67 | 80 | 89 | 118 | 131 | 137.5 |
| T89-30 | 26 | 29.5 | 38 | 43 | 52 | 58 | 70.5 | 78 | N/A | 116 | 120 |
| T89-31 | 25.5 | 31 | 38.5 | 43.5 | 53.5 | 62 | 74 | 82 | N/A | 123 | 128 |
| T89-32 | 28 | 33.5 | 41 | 47 | 56 | 64 | 78 | 87 | 113 | 128 | 134 |
| T89-33 | 27.5 | 29.5 | 37 | 42 | 50 | 56 | 67 | 73 | N/A | 72 | N/A |
| T89-34 | 29.5 | 34 | 43 | 47 | 56 | 66 | 73 | 81.5 | 112 | 123.5 | 129 |
| T89-35 | 16 | 19.5 | 25 | 28 | 35.5 | 42 | 52 | 58 | 80 | 90 | 94 |
| T89-36 | 25 | 30 | 36 | 44 | 53 | 62.5 | 74 | 82.5 | 110 | 124 | 129 |
| T89-37 | 16 | 19 | 27 | 30.5 | 38 | 45 | 53 | 58 | 80 | 92 | 96 |
| T89-38 | 24 | 29 | 37 | 41 | 51 | 60 | 73.5 | 81 | 108 | 122 | 129 |
| T89-39 | 26 | 30 | 40 | 45 | 55 | 64 | 79 | 88 | 116 | 130 | 137 |
| T89-40 | 28 | 32 | 39.5 | 44 | 52.5 | 61 | 73 | 81 | 108.5 | 124 | 129 |
| T89-41 | 23 | 28 | 35 | 40.5 | 49 | 55 | 68 | 76 | 103 | 117 | 122 |

Table 1.14b Growth data for KR152

| | Diameter (mm) Days in greenhouse | | | | | | |
|---|---|---|---|---|---|---|---|
| | 28 | 32 | 38 | 45 | 55 | 59 | 60 |
| KR152-1B | 3.0 | 3.5 | 4.8 | 6.1 | 8.0 | N/A | 9.4 |
| KR152-2B | 2.9 | 3.3 | 4.7 | 6.6 | 8.6 | N/A | 9.6 |
| KR152-3B | 3.8 | 4.1 | 5.7 | 7.5 | N/A | N/A | N/A |
| KR152-4A | 3.1 | 4.1 | 5.3 | 6.9 | N/A | 9.9 | 9.4 |
| KR152-4B | N/A | 3.5 | 5.0 | 6.4 | 8.4 | N/A | 10.0 |
| T89-23 | 3.2 | 3.6 | 5.2 | 6.8 | N/A | N/A | N/A |
| T89-24 | 3.4 | 3.9 | 5.3 | 7.4 | 9.3 | 10.4 | 10.3 |
| T89-25 | 3.6 | 4.3 | 5.4 | 6.5 | N/A | 9.3 | 9.9 |
| T89-26 | 2.9 | 3.1 | 4.2 | 6.0 | 7.7 | N/A | 9.1 |
| T89-27 | 3.6 | 4.0 | 5.2 | 7.1 | N/A | 9.2 | 9.5 |
| T89-28 | 3.6 | 3.8 | 5.1 | 6.9 | N/A | 9.7 | 9.5 |
| T89-29 | 3.7 | 4.2 | 4.8 | 6.1 | 8.2 | 9.5 | 8.4 |
| T89-30 | 3.1 | 3.1 | 4.9 | 6.8 | N/A | 8.9 | 8.7 |
| T89-31 | 3.1 | 3.5 | 4.7 | 6.0 | N/A | N/A | 8.7 |
| T89-32 | 3.2 | 3.5 | 4.9 | 6.6 | 8.6 | N/A | 9.1 |
| T89-33 | 3.1 | 3.1 | 4.1 | 6.2 | N/A | N/A | N/A |
| T89-34 | 3.2 | 3.8 | 5.0 | 6.0 | 9.3 | 10.3 | 11.0 |
| T89-35 | 1.8 | 1.9 | 2.9 | 4.3 | 6.2 | 7.0 | 7.5 |
| T89-36 | 3.1 | 3.4 | 4.7 | 6.4 | 8.1 | N/A | 9.6 |
| T89-37 | 2.0 | 2.5 | 4.1 | 6.0 | 7.8 | 9.1 | 9.0 |
| T89-38 | 2.8 | 3.3 | 4.4 | 6.4 | 7.6 | N/A | 8.5 |
| T89-39 | 3.0 | 3.4 | 4.3 | 6.5 | 8.0 | N/A | 9.4 |
| T89-40 | 3.1 | 3.3 | 4.5 | 5.8 | 7.9 | N/A | 8.6 |
| T89-41 | 2.7 | 3.1 | 4.2 | 5.9 | 7.9 | N/A | 9.6 |

Construction Group KR163

Construct KR163 corresponding to EST A086P08U gene bank number A1165576. This gene is selected from the Hertzberg et al 2001 data and is up-regulated in the C zone. This construct induces increased growth. This construct gave an increased diameter growth rate of up to 30% compared to the wild types when comparing the fastest growing individuals. This construct meets Growth Filter criteria (2) and (4) as shown in the below table 1.21.

Table 1.16a Growth data for KR163

| | Height (cm) Days in greenhouse | | | | | | | | | | |
|---|---|---|---|---|---|---|---|---|---|---|---|
| | 25 | 28 | 32 | 34 | 38 | 41 | 45 | 48 | 55 | 59 | 60 |
| KR163-1A | 25 | 28 | 35 | 40 | 48 | 56 | 66 | 74 | 96 | 108 | 112 |
| KR163-1B | 25 | 29.5 | 36.5 | 41.5 | 50 | 59 | 71 | 80 | N/A | 120 | 127.5 |
| KR163-2B | 25.5 | 30.5 | 41 | 44.5 | 54 | 64 | 70 | 86.5 | 117 | 130 | 136 |
| KR163-3A | 21.5 | 26 | 34 | 39 | 48.5 | 56 | 68.5 | 77 | 107 | 126 | 128 |
| KR163-3B | 28.5 | 33 | 42 | 47.5 | 60 | 66.5 | 80 | 89 | N/A | 132 | 136 |
| T89-23 | 28 | 34 | 42 | 47 | 55 | 63 | 76 | 83 | N/A | 82 | N/A |
| T89-24 | 29.5 | 33 | 42 | 47 | 55 | 65 | 75 | 83 | 108 | 120 | 125 |
| T89-25 | 31 | 35 | 45 | 50.5 | 60 | 68.5 | 80 | 89 | N/A | 128 | 132 |
| T89-26 | 28 | 32.5 | 41 | 46 | 56 | 65 | 79 | 88 | 115 | 126 | 132 |
| T89-27 | 29.5 | 34.5 | 43 | 47 | 56 | 66 | 79 | 86 | N/A | 127.5 | 132 |

-continued

| | | | | | | | | | | | |
|---|---|---|---|---|---|---|---|---|---|---|---|
| T89-28 | 28.5 | 33 | 42 | 46.5 | 56 | 64 | 76 | 86 | N/A | 125 | 130 |
| T89-29 | 31 | 35 | 42 | 49 | 57.5 | 67 | 80 | 89 | 118 | 131 | 137.5 |
| T89-30 | 26 | 29.5 | 38 | 43 | 52 | 58 | 70.5 | 78 | N/A | 116 | 120 |
| T89-31 | 25.5 | 31 | 38.5 | 43.5 | 53.5 | 62 | 74 | 82 | N/A | 123 | 128 |
| T89-32 | 28 | 33.5 | 41 | 47 | 56 | 64 | 78 | 87 | 113 | 128 | 134 |
| T89-33 | 27.5 | 29.5 | 37 | 42 | 50 | 56 | 67 | 73 | N/A | 72 | N/A |
| T89-34 | 29.5 | 34 | 43 | 47 | 56 | 66 | 73 | 81.5 | 112 | 123.5 | 129 |
| T89-35 | 16 | 19.5 | 25 | 28 | 35.5 | 42 | 52 | 58 | 80 | 90 | 94 |
| T89-36 | 25 | 30 | 36 | 44 | 53 | 62.5 | 74 | 82.5 | 110 | 124 | 129 |
| T89-37 | 16 | 19 | 27 | 30.5 | 38 | 45 | 53 | 58 | 80 | 92 | 96 |
| T89-38 | 24 | 29 | 37 | 41 | 51 | 60 | 73.5 | 81 | 108 | 122 | 129 |
| T89-39 | 26 | 30 | 40 | 45 | 55 | 64 | 79 | 88 | 116 | 130 | 137 |
| T89-40 | 28 | 32 | 39.5 | 44 | 52.5 | 61 | 73 | 81 | 108.5 | 124 | 129 |
| T89-41 | 23 | 28 | 35 | 40.5 | 49 | 55 | 68 | 76 | 103 | 117 | 122 |

Table 1.16b Growth data for KR163

| | Diameter (mm) Days in greenhouse | | | | | | |
|---|---|---|---|---|---|---|---|
| | 28 | 32 | 38 | 45 | 55 | 59 | 60 |
| KR163-1A | 3.1 | 3.4 | 4.6 | 6.3 | 8.5 | 9.5 | 9.5 |
| KR163-1B | 2.6 | 3.3 | 4.4 | 6.1 | N/A | 8.9 | 8.8 |
| KR163-2B | 3.0 | 3.2 | 5.1 | 6.4 | 9.0 | N/A | 9.8 |
| KR163-3A | 2.7 | 3.1 | 4.7 | 6.2 | 7.4 | N/A | 8.1 |
| KR163-3B | 3.7 | 3.4 | 4.9 | 6.7 | N/A | 12.7 | 13.0 |
| T89-23 | 3.2 | 3.6 | 5.2 | 6.8 | N/A | N/A | N/A |
| T89-24 | 3.4 | 3.9 | 5.3 | 7.4 | 9.3 | 10.4 | 10.3 |
| T89-25 | 3.6 | 4.3 | 5.4 | 6.5 | N/A | 9.3 | 9.9 |
| T89-26 | 2.9 | 3.1 | 4.2 | 6.0 | 7.7 | N/A | 9.1 |
| T89-27 | 3.6 | 4.0 | 5.2 | 7.1 | N/A | 9.2 | 9.5 |
| T89-28 | 3.6 | 3.8 | 5.1 | 6.9 | N/A | 9.7 | 9.5 |
| T89-29 | 3.7 | 4.2 | 4.8 | 6.1 | 8.2 | 9.5 | 8.4 |
| T89-30 | 3.1 | 3.1 | 4.9 | 6.8 | N/A | 8.9 | 8.7 |
| T89-31 | 3.1 | 3.5 | 4.7 | 6.0 | N/A | N/A | 8.7 |
| T89-32 | 3.2 | 3.5 | 4.9 | 6.6 | 8.6 | N/A | 9.1 |
| T89-33 | 3.1 | 3.1 | 4.1 | 6.2 | N/A | N/A | N/A |
| T89-34 | 3.2 | 3.8 | 5.0 | 6.0 | 9.3 | 10.3 | 11.0 |
| T89-35 | 1.8 | 1.9 | 2.9 | 4.3 | 6.2 | 7.0 | 7.5 |
| T89-36 | 3.1 | 3.4 | 4.7 | 6.4 | 8.1 | N/A | 9.6 |
| T89-37 | 2.0 | 2.5 | 4.1 | 6.0 | 7.8 | 9.1 | 9.0 |
| T89-38 | 2.8 | 3.3 | 4.4 | 6.4 | 7.6 | N/A | 8.5 |
| T89-39 | 3.0 | 3.4 | 4.3 | 6.5 | 8.0 | N/A | 9.4 |
| T89-40 | 3.1 | 3.3 | 4.5 | 5.8 | 7.9 | N/A | 8.6 |
| T89-41 | 2.7 | 3.1 | 4.2 | 5.9 | 7.9 | N/A | 9.6 |

Construction Group KR235

Construct KR235 corresponding to EST A017P24U gene bank number AI162414. This gene is selected from the Hertzberg et al 2001 data and is up-regulated in the D and E zones. This construct induces increased growth. This construct gave an increased maximum height growth rate of up to 17% compared to the wild types when comparing the fastest growing individuals. This construct meets Growth Filter criteria (1), and (4) as shown in the below table 1.21.

TABLE 1.17

Growth data for KR235

| | Height (cm) | | | | | | | Diameter (mm) | | | | | |
|---|---|---|---|---|---|---|---|---|---|---|---|---|---|
| | Days in greenhouse | | | | | | | | | | | | |
| | 18 | 26 | 33 | 39 | 47 | 53 | 65 | 33 | 39 | 47 | 53 | 59 | 65 |
| KR235-1A | 22 | 37 | 51 | 83 | 99 | 118 | 146 | 4.7 | 5.9 | 6.3 | 7.0 | 7.1 | 7.8 |
| KR235-3A | 23 | 38 | 53 | 87 | 103 | 118 | 152 | 4.4 | 5.4 | 6.0 | 6.3 | 6.4 | 7.1 |
| KR235-3B | 25 | 44 | 59 | 93 | 111 | 131 | 169 | 5.1 | 6.5 | 6.9 | 7.7 | 7.9 | 8.8 |
| KR235-4B-A | 28 | 45 | 68 | 109 | 126 | 150 | 197 | 4.8 | 6.4 | 7.3 | 7.8 | N/A | 9.6 |
| KR235-6A | 25 | 41 | 58 | 82 | 98 | 118 | 158 | 4.5 | 5.8 | 6.3 | 6.9 | 7.7 | 8.6 |
| T89-133 | 23 | 37 | 51 | 84 | 103 | 121 | 156 | 4.7 | 6.7 | 7.7 | 8.4 | 9.1 | 9.7 |
| T89-134 | 25 | 38 | 50 | 80 | 95 | 112 | 149 | 4.4 | 6.2 | 7.1 | 7.6 | 7.6 | 8.4 |
| T89-135 | 17 | 29 | 43 | 71 | 86 | 104 | 140 | 4.8 | 6.6 | 7.7 | 8.6 | 9.1 | 9.1 |
| T89-136 | 19 | 31 | 45 | 72 | 85 | 103 | 138 | 4.6 | 5.3 | 6.0 | 6.4 | 7.3 | 7.8 |
| T89-137 | 22 | 37 | 52 | 82 | 96 | 112 | 151 | 5.0 | 6.5 | 7.3 | 7.8 | N/A | 10.0 |

TABLE 1.17-continued

Growth data for KR235

| | Height (cm) | | | | | | | Diameter (mm) | | | | | |
|---|---|---|---|---|---|---|---|---|---|---|---|---|---|
| | Days in greenhouse | | | | | | | | | | | | |
| | 18 | 26 | 33 | 39 | 47 | 53 | 65 | 33 | 39 | 47 | 53 | 59 | 65 |
| T89-138 | 21 | 33 | 47 | 78 | 94 | 109 | 140 | 4.9 | 6.0 | 7.0 | 7.8 | 8.4 | 9.0 |
| T89-139 | 24 | 39 | 56 | 92 | 108 | 124 | 159 | 4.8 | 5.7 | 6.3 | 7.0 | 7.6 | 8.4 |
| T89-140 | 25 | 41 | 56 | 88 | 101 | 115 | 148 | 4.9 | 6.0 | 6.0 | 6.8 | 7.0 | 7.8 |
| T89-141 | 17 | 30 | 45 | 77 | 87 | 104 | 132 | 5.0 | 5.3 | 6.2 | 6.4 | 6.9 | 7.2 |
| T89-142 | 24 | 38 | 54 | 85 | 99 | 116 | 146 | 5.3 | 5.9 | 6.3 | 6.6 | 7.6 | 8.3 |
| T89-143 | 24 | 40 | 56 | 89 | 107 | 122 | 155 | 4.7 | 5.7 | 6.3 | 6.8 | 7.3 | 8.4 |
| T89-144 | 23 | 37 | 52 | 76 | 89 | 107 | 139 | 4.5 | 5.9 | 6.5 | 6.9 | 7.1 | 7.9 |
| T89-146 | 27 | 43 | 58 | 84 | 99 | 116 | 153 | 4.6 | 6.0 | 6.7 | 7.4 | 7.8 | 8.5 |
| T89-147 | 26 | 44 | 62 | 95 | 111 | 130 | 167 | 5.4 | 6.5 | 6.9 | 7.4 | 8.0 | 8.7 |
| T89-148 | 21 | 32 | 47 | 77 | 91 | 109 | 146 | 4.2 | 5.4 | 6.1 | 6.6 | 6.9 | 7.8 |

Construction Group KR242

Construct KR242 corresponding to EST A018P65U gene bank number A1162510. This gene is selected from the Schrader et al 2004 data and is up-regulated in samples 8-10 in the B series. This construct induces increased growth. This construction group shows both increased height growth (up to 16% increased height when comparing the tallest individuals from the construction group and the wt control plants) and increased diameter growth (with an 16% increased diameter growth rate when comparing the averages between construction group and control plants). This construct meets Growth Filter criteria (1), (3) and (4) as shown in the below table 1.21.

Table 1.18a Growth data for KR242

| | Height (cm) | | | | | | | | | | |
|---|---|---|---|---|---|---|---|---|---|---|---|
| | Days in green house | | | | | | | | | | |
| | 25 | 28 | 32 | 34 | 38 | 41 | 45 | 48 | 55 | 59 | 60 |
| KR242-1A | 34 | 39 | 48 | 53.5 | 63.5 | 73.5 | 86 | 95 | 125 | 134 | 139 |
| KR242-1B | 33 | 38 | 47 | 52.5 | 65 | 74 | 78 | 97 | N/A | 139 | 146 |
| KR242-2B | 37 | 42.5 | 53 | 59 | 72.5 | 85 | 100 | 110.5 | 140 | 155 | 160 |
| KR242-3A | 29 | 34 | 44 | 50 | 59.5 | 66.5 | 80 | 89.5 | 115 | 130 | 136 |
| KR242-4A | 31 | 36 | 45 | 51 | 62 | 71.5 | 86 | 95 | N/A | 132 | 136 |
| KR242-4B | 27 | 32 | 42 | 48 | 59 | 68 | 83 | 92 | 124 | 138 | 146 |
| KR242-5A | 31 | 35 | 44.5 | 50 | 60.5 | 70 | 85 | 93 | 124 | 140 | 146 |
| KR242-5B | 27 | 31.5 | 39 | 43 | 52 | 59.5 | N/A | 76 | N/A | 115 | 119 |
| T89-23 | 28 | 34 | 42 | 47 | 55 | 63 | 76 | 83 | N/A | 82 | N/A |
| T89-24 | 29.5 | 33 | 42 | 47 | 55 | 65 | 75 | 83 | 108 | 120 | 125 |
| T89-25 | 31 | 35 | 45 | 50.5 | 60 | 68.5 | 80 | 89 | N/A | 128 | 132 |
| T89-26 | 28 | 32.5 | 41 | 46 | 56 | 65 | 79 | 88 | 115 | 126 | 132 |
| T89-27 | 29.5 | 34.5 | 43 | 47 | 56 | 66 | 79 | 86 | N/A | 127.5 | 132 |
| T89-28 | 28.5 | 33 | 42 | 46.5 | 56 | 64 | 76 | 86 | N/A | 125 | 130 |
| T89-29 | 31 | 35 | 42 | 49 | 57.5 | 67 | 80 | 89 | 118 | 131 | 137.5 |
| T89-30 | 26 | 29.5 | 38 | 43 | 52 | 58 | 70.5 | 78 | N/A | 116 | 120 |
| T89-31 | 25.5 | 31 | 38.5 | 43.5 | 53.5 | 62 | 74 | 82 | N/A | 123 | 128 |
| T89-32 | 28 | 33.5 | 41 | 47 | 56 | 64 | 78 | 87 | 113 | 128 | 134 |
| T89-33 | 27.5 | 29.5 | 37 | 42 | 50 | 56 | 67 | 73 | N/A | 72 | N/A |
| T89-34 | 29.5 | 34 | 43 | 47 | 56 | 66 | 73 | 81.5 | 112 | 123.5 | 129 |
| T89-35 | 16 | 19.5 | 25 | 28 | 35.5 | 42 | 52 | 58 | 80 | 90 | 94 |
| T89-36 | 25 | 30 | 36 | 44 | 53 | 62.5 | 74 | 82.5 | 110 | 124 | 129 |
| T89-37 | 16 | 19 | 27 | 30.5 | 38 | 45 | 53 | 58 | 80 | 92 | 96 |
| T89-38 | 24 | 29 | 37 | 41 | 51 | 60 | 73.5 | 81 | 108 | 122 | 129 |
| T89-39 | 26 | 30 | 40 | 45 | 55 | 64 | 79 | 88 | 116 | 130 | 137 |
| T89-40 | 28 | 32 | 39.5 | 44 | 52.5 | 61 | 73 | 81 | 108.5 | 124 | 129 |
| T89-41 | 23 | 28 | 35 | 40.5 | 49 | 55 | 68 | 76 | 103 | 117 | 122 |

Table 1.18b Growth data for KR242

| | Diameter (mm) | | | | | | |
|---|---|---|---|---|---|---|---|
| | Days in greenhouse | | | | | | |
| | 28 | 32 | 38 | 45 | 55 | 59 | 60 |
| KR242-1A | 3.3 | 4.0 | 5.6 | 7.8 | 9.5 | 11.2 | 11.2 |
| KR242-1B | 3.9 | 4.2 | 5.4 | 8.1 | N/A | N/A | 10.4 |
| KR242-2B | 3.8 | 4.2 | 5.6 | 7.5 | 9.4 | N/A | 10.8 |
| KR242-3A | 3.2 | 4.0 | 5.0 | 8.0 | 10.1 | 10.8 | 11.1 |
| KR242-4A | 3.5 | 4.1 | 5.7 | 7.9 | N/A | 11.0 | 11.2 |
| KR242-4B | 3.1 | 3.4 | 4.6 | 6.3 | 8.9 | N/A | 9.3 |
| KR242-5A | 3.1 | 3.7 | 4.5 | 6.3 | 8.7 | N/A | 9.8 |
| KR242-5B | 3.2 | 3.4 | 5.2 | N/A | N/A | 10.2 | 10.7 |

-continued

| | | | | | | | |
|---|---|---|---|---|---|---|---|
| T89-23 | 3.2 | 3.6 | 5.2 | 6.8 | N/A | N/A | N/A |
| T89-24 | 3.4 | 3.9 | 5.3 | 7.4 | 9.3 | 10.4 | 10.3 |
| T89-25 | 3.6 | 4.3 | 5.4 | 6.5 | N/A | 9.3 | 9.9 |
| T89-26 | 2.9 | 3.1 | 4.2 | 6.0 | 7.7 | N/A | 9.1 |
| T89-27 | 3.6 | 4.0 | 5.2 | 7.1 | N/A | 9.2 | 9.5 |
| T89-28 | 3.6 | 3.8 | 5.1 | 6.9 | N/A | 9.7 | 9.5 |
| T89-29 | 3.7 | 4.2 | 4.8 | 6.1 | 8.2 | 9.5 | 8.4 |
| T89-30 | 3.1 | 3.1 | 4.9 | 6.8 | N/A | 8.9 | 8.7 |
| T89-31 | 3.1 | 3.5 | 4.7 | 6.0 | N/A | N/A | 8.7 |
| T89-32 | 3.2 | 3.5 | 4.9 | 6.6 | 8.6 | N/A | 9.1 |
| T89-33 | 3.1 | 3.1 | 4.1 | 6.2 | N/A | N/A | N/A |
| T89-34 | 3.2 | 3.8 | 5.0 | 6.0 | 9.3 | 10.3 | 11.0 |
| T89-35 | 1.8 | 1.9 | 2.9 | 4.3 | 6.2 | 7.0 | 7.5 |
| T89-36 | 3.1 | 3.4 | 4.7 | 6.4 | 8.1 | N/A | 9.6 |
| T89-37 | 2.0 | 2.5 | 4.1 | 6.0 | 7.8 | 9.1 | 9.0 |
| T89-38 | 2.8 | 3.3 | 4.4 | 6.4 | 7.6 | N/A | 8.5 |
| T89-39 | 3.0 | 3.4 | 4.3 | 6.5 | 8.0 | N/A | 9.4 |
| T89-40 | 3.1 | 3.3 | 4.5 | 5.8 | 7.9 | N/A | 8.6 |
| T89-41 | 2.7 | 3.1 | 4.2 | 5.9 | 7.9 | N/A | 9.6 |

Construction Group KR318
Construction Group KR318

Construct KR318 corresponding to EST A050P08U gene bank number AI163860. This gene is selected from the Schrader et al 2004 data and is up-regulated in samples 6-9 in the B series. This construct induces increased growth. This construct gives both an increased height and increased diameter growth. When comparing the individuals with the highest values from the construction group and the wild type control group the increase in maximum height growth rate was 21% and the increase in diameter growth rate was 13%. This construct meets Growth Filter criteria (1), and (4) as shown in the below table 1.21.

TABLE 1.19

Growth data for KR318

| | Height (cm) | | | | | | | Diameter (mm) | | | | |
|---|---|---|---|---|---|---|---|---|---|---|---|---|
| | Days in greenhouse | | | | | | | | | | | |
| | 19 | 21 | 29 | 35 | 42 | 49 | 53 | 21 | 29 | 35 | 42 | 53 |
| KR318-1B | 30 | 35 | 62 | 85 | 114 | 139 | 150 | 3.6 | 5.4 | 6.5 | 8.0 | 11.1 |
| KR318-3A-A | 33 | 37 | 66 | 93.5 | 132 | 167 | 183 | 3.6 | 5.1 | 7.1 | 8.3 | 9.5 |
| KR318-3A-B | 28 | 33 | 57 | 81 | 112 | 138 | 149 | 3.0 | 4.5 | 5.9 | 6.2 | 7.5 |
| KR318-4A | 28 | 33 | 56 | 74.5 | 106 | 136 | 150 | 3.3 | 4.8 | 6.0 | 8.2 | 9.8 |
| KR318-4B-B | 30 | 35 | 57 | 79 | 108 | 138 | 153 | 3.4 | 4.9 | 6.0 | 7.2 | 8.6 |
| T89-66 | 23 | 27 | 49 | 69 | 97 | 127 | 141 | 3.2 | 5.7 | 6.9 | 7.9 | 10.0 |
| T89-67 | 34 | 39 | 61 | 83.5 | 116 | 144 | 159 | 4.1 | 5.4 | 6.7 | 8.0 | 9.7 |
| T89-68 | 27 | 32 | 51 | 69 | 99 | 129 | 143 | 3.4 | 4.8 | 5.9 | 7.9 | 9.5 |
| T89-69 | 35 | 40 | 61 | 81 | N/A | 136 | 153 | 3.6 | 5.4 | 6.8 | N/A | 9.0 |
| T89-70 | 29 | 32 | 51 | 68 | 97 | 125 | 140 | 3.1 | 4.7 | 5.7 | 7.5 | 8.6 |
| T89-71 | 29 | 44 | 55 | 74 | 107 | 135 | 148 | 3.4 | 4.9 | 6.6 | 7.6 | 9.0 |
| T89-72 | 33 | 38 | 57 | 75 | 102 | 129 | 145 | 3.2 | 4.7 | 6.0 | 8.0 | 9.3 |
| T89-73 | 34 | 40 | 59 | 78 | 106 | 132 | 149 | 3.5 | 5.7 | 6.2 | 8.2 | 9.5 |

Construction Group KR1298

Construct KR129 corresponding to EST A047P55U gene bank number AI163758. This gene is selected from the Hertzberg et al 2001 data and is up-regulated in the C and D zones. This construct induces increased growth. This construction group shows an increased height growth with an 14% increased final height and an 8% increased maximum height growth rate. This construct meets Growth Filter criterion (1) as shown in the below table 1.21.

TABLE 1.20

Growth data for KR129B

| | Height (cm) | | | | | | Diameter (mm) | | | | |
|---|---|---|---|---|---|---|---|---|---|---|---|
| | Days in greenhouse | | | | | | | | | | |
| | 21 | 28 | 35 | 42 | 49 | 55 | 28 | 35 | 42 | 49 | 55 |
| KR129B-2A | 33 | 48 | 75 | 105 | 135 | 155 | 3.6 | 5.1 | 6.2 | 6.6 | 7.1 |
| KR129B-2B | 33 | 46 | 69 | 96 | 124 | 143 | 4.2 | 5.1 | 6.5 | 6.5 | 7.4 |
| KR129B-3A | 37 | 53 | 77 | 105 | 133 | 151 | 4.5 | 5.3 | 6.5 | 7.1 | 7.6 |
| KR129B-3B | 19 | 28 | 47 | 71 | 98 | 118 | 3.0 | 4.3 | 5.4 | 6.2 | 6.5 |
| T89-89 | 10 | 13 | 25 | 45 | 64 | 77 | N/A | 4.9 | 4.3 | 4.4 | 5.7 |
| T89-92 | 27 | 39 | 61 | 89 | 118 | 135 | 3.6 | 5.1 | 6.2 | 6.6 | 7.3 |
| T89-93 | 23 | 33 | 51 | 75 | 102 | 120 | 3.0 | 4.1 | 4.9 | 6.0 | 6.7 |
| T89-94 | 25 | 35 | 59 | 85 | 115 | 134 | 3.5 | 4.8 | 6.1 | 6.9 | 7.3 |
| T89-95 | 25 | 32 | 49 | 72 | 96 | 115 | 2.8 | 4.0 | 5.0 | 5.3 | 5.9 |
| T89-96 | 30 | 47 | 73 | 99 | 110 | 113 | 5.0 | 5.8 | 7.3 | 8.1 | 8.6 |
| T89-97 | 27 | 36 | 58 | 86 | 115 | 135 | 3.4 | 4.3 | 5.4 | 6.2 | 6.9 |
| T89-98 | 29 | 41 | 65 | 93 | 120 | 140 | 3.9 | 5.6 | 5.9 | 6.9 | 7.5 |
| T89-99 | 28 | 39 | 62 | 89 | 115 | 136 | 3.4 | 4.8 | 5.9 | 6.3 | 7.1 |
| T89-100 | 29 | 41 | 65 | 92 | 118 | 134 | 4.0 | 5.3 | 6.3 | 7.3 | 8.3 |
| T89-101 | 24 | 37 | 57 | 81 | 110 | 124 | 3.6 | 4.8 | 6.1 | 6.9 | 7.7 |
| T89-102 | 31 | 47 | 71 | 96 | 125 | 144 | 4.6 | 5.5 | 6.6 | 7.0 | 7.4 |

In the below Table 1.21 shows the ratios of height and diameter growth measures of specified construction group relative to corresponding wildtype group (e.g. average final height (AFH) ratio: $\text{AFH}_{Construction\_group}/\text{AFH}_{Wildtype\_group}$). Table 1.22 contain ratios of computed growth measures AFH, AFD, AMHGR, ADGR, MFH, MFD, MMHGR and MDC. (Declaration of growth measures described above).

TABLE 1.21

Overall results of selected constructs - for the overall phenotype "increased growth"

| | Phenotypes | | | | | | | |
|---|---|---|---|---|---|---|---|---|
| Construct | Average Final Height (KRmean/ WTmean) AFH | Average Final Diameter (KRmean/ WTmean) AFD | Average MAXIMUM HEIGHT GROWTH rate (KRmean/ WTmean) AMHGR | Average Diameter Coefficient (KRmean/ WTmean) ADGR | Maximum Final Height (KRmax/ WTmax) MFH | Maximum Final Diameter (KRmax/ WTmax) MFD | Maximum MAXIMUM HEIGHT GROWTH RATE KRmax/ WTmax MMHGR | Maximum Diameter Coefficient (KRmax/ WTmax) MDC |
| KR121 | 1.14 | 1.16 | 1.09 | 1.15 | 1.09 | 1.09 | 1.05 | 1.12 |
| KR125 | 1.09 | 1.12 | 1.00 | 1.06 | 1.05 | 1.05 | 0.99 | 1.06 |
| KR129B | 1.14 | 0.98 | 1.08 | 0.98 | 1.08 | 0.88 | 1.07 | 0.84 |
| KR140 | 1.09 | 1.00 | 1.12 | 0.98 | 1.10 | 0.92 | 1.07 | 0.85 |
| KR152 | 1.10 | 1.05 | 1.11 | 1.06 | 1.11 | 0.91 | 1.08 | 0.93 |
| KR162 | 1.09 | 1.07 | 1.09 | 1.08 | 1.01 | 1.03 | 1.02 | 1.06 |
| KR163 | 1.02 | 1.07 | 1.09 | 1.13 | 0.99 | 1.18 | 1.09 | 1.30 |
| KR221 | 0.90 | 0.98 | 0.97 | 1.21 | 0.91 | 0.92 | 0.99 | 1.09 |
| KR224 | 1.07 | 1.05 | 1.05 | 0.97 | 1.11 | 0.96 | 1.11 | 0.94 |
| KR235 | 1.11 | 0.99 | 1.11 | 0.97 | 1.18 | 0.96 | 1.17 | 0.96 |
| KR240 | 0.99 | 1.07 | 0.99 | 1.20 | 0.96 | 1.01 | 0.92 | 1.15 |
| KR242 | 1.12 | 1.15 | 1.10 | 1.16 | 1.16 | 1.02 | 1.10 | 1.05 |
| KR292 | 1.04 | 1.09 | 1.04 | 1.09 | 0.99 | 1.14 | 1.04 | 1.15 |
| KR313 | 1.00 | 1.00 | 1.09 | 1.10 | 1.01 | 1.01 | 1.20 | 1.15 |
| KR318 | 1.07 | 1.00 | 1.06 | 1.01 | 1.15 | 1.11 | 1.21 | 1.13 |
| KR459 | 1.07 | 0.98 | 1.05 | 0.94 | 1.24 | 0.92 | 1.23 | 0.92 |
| KR463 | 1.02 | 1.04 | 1.02 | 1.18 | 0.98 | 1.06 | 1.05 | 1.16 |
| KR465 | 1.02 | 0.98 | 1.10 | 1.23 | 0.97 | 0.93 | 1.03 | 1.13 |

1.4 Discussion

By using the right amount of data and information for the selection of genes to be functionally analysed in a functional genomics program, in the present case directed towards growth properties, allowed us to find a number of genes that can be utilized in modifying growth in plants, specifically trees.

Of all the gene tested in this program less than 18% passed the first level of selection and less than 9% passed the second level of the growth criteria's set up here for genes of extra interest. Construction groups passing the second level of the growth criteria's set up here for genes of extra interest are KR121, KR152, KR163, KR235, KR242, KR292, KR459 and KR465. Although this is only a smaller part of the genes selected to be tested, the numbers are high compared to what one would expect from a random choice of genes to be tested, showing the importance and utility for our kind of selection of genes to be tested.

The foregoing example also illustrate the following: when comparing phenotypes according to single criteria, such as height or diameter, one are able to record and select genes causing strong phenotypes such as the ones selected by growth criteria filters 3 and 4.

However, comparing the phenotypes according to multiple criteria, such as average final height, maximum final height, average MAXIMUM HEIGHT GROWTH RATE, and maximum MAXIMUM HEIGHT GROWTH RATE reveals that the down-regulation of the expression of some genes has a surprisingly large effect of the overall growth characteristics. As illustrated, this has allowed the identification of a subset of genes, wherein down-regulation of their expression leads to a considerable effect on plant growth. Having identified this subset of genes provides a clear advance over the state of the art and has significantly facilitated the generation and selection of promising transformation events for generation of transgenic plants with improved phenotypic traits.

When producing commercial lines using any of the different ways possible to down regulate gene expression one could produce many lines with different methods and test those for the desired properties. This could be done because different down regulation levels of the trait gene will often give different results. This can be clearly seen in the data in this example. One would then select the most promising transformation events.

References
1. Sterky et al. 1998 (Proc. Natl. Acad. Sci. USA, 1998 (95), 13330-13335
2. Hertzberg et al. 2001 (Proc. Natl. Acad. Sci. USA, 2001 (98), 14372-14737,
3. Schrader et al. 2005 (Plant Cell, (16), 2278-2292
4. White et al. 1999 (Science 1999 (286) 2187-2184
5. Aharoni et al. 2000 (Plant Cell 2000 (12) 647-662
6. Uggla et al. 1996 Proc. Natl. Acad. Sci. USA, 1996 (93), 9282-9286
7. Schena et al. 1995 Science 1995 (270) 467-470
8. Wilson, B. F., Wodzicki, T. J. and Zhaner, R. (1966), Forest Science 12, pp 438-440
9. Sambrook et al., Molecular Cloning: A Laboratory Manual, 2nd Ed., Cold Spring Harbor,
10. Rognes T, 2001, Nucleic Acids Research, 29, 1647-1652, 1989.
11. Smith TF and Waterman M S, 1981, Journal of Molecular Biology, 147, 195-197.
12. H. Neurath and R. L. Hill, 1979, *In, The Proteins*, Academic Press, New York.
13. WO2004097024
14. U.S. Pat. No. 4,987,071
15. U.S. Pat. No. 5,543,508.
16. U.S. Pat. No. 5,231,020
17. U.S. Pat. No. 5,583,021.
18. WO2006/078431
19. Slade and Knauf, *Transgenic Res.* 2005 April; 14(2):109-15
20. Henikoff, Till, and Comai, *Plant Physiol.* 2004 June; 135(2):630-6.
21. Ichikawa et al. (1997) Nature 390 698-701;
22. Kakimoto et al. (1996) Science 274: 982-985
23. WO 96/06166
24. WO 98/53057
25. Lichtenstein and Nellen (1997), Antisense Technology: A Practical Approach IRL Press at Oxford University, Oxford, England.
26. U.S. Pat. No. 5,107,065
27. U.S. Pat. No. 6,506,559,
28. US Patent Application Publication No. 2002/0168707 A1
29. U.S. patent application Ser. No. 09/423,143 (see WO 98/53083),
30. U.S. patent application Ser. No. 09/127,735 (see WO 99/53050)
31. U.S. patent application Ser. No. 09/084,942 (see WO 99/61631),
32. Brummel D. A. et al. Plant Journal 2003, 33, pages 793-800
33. Karimi, M. et al., Trends In plant Sciences, Vol 7 no 5 pp 193-195.
34. Wesley S. V. et al., Plant Journal 2001, 27, pages 581-590.
35. Vasil et al. 1984, Cell Culture and Somatic Cell Genetics of Plants, Vol I, II and III, Laboratory Procedures
36. Niu et al., Science 2006, vol 24, No. 11 pp 1420-1428)
37. G. A Tuskan et al, Science vol 313 No. 5793, pages 1596-1604.

---

The invention claimed is:

1. A method of producing a transgenic tree, the method comprising;
transforming one or more regenerable cells of a tree expressing a gene product encoded by the nucleotide sequence of SEQ ID NO:15 with a recombinant DNA construct, such that the expression of the gene product encoded by the nucleotide sequence SEQ ID NO: 15 is suppressed, wherein the expression is suppressed by RNA interference, and wherein the RNA interference is effected by an RNA polynucleotide that is at least 95% identical to an at least 30 consecutive nucleotide portion of an RNA transcript of SEQ ID NO: 15.

2. The method according to claim 1, wherein said recombinant DNA construct comprises a nucleotide sequence selected from the group consisting of:

a) the polynucleotide sequence of SEQ ID NO: 36;
b) a complementary polynucleotide sequence of the entire polynucleotide sequence of a); and
c) a polynucleotide sequence of at least 30 consecutive nucleotide residues, that is at least 95% identical to a 30 nucleotide sub-sequence of the polynucleotide sequence of a) or b).

3. The method according to claim 2, wherein the recombinant DNA construct further comprises a promoter selected from the group consisting of a constitutive promoter, an inducible promoter, and a tissue specific promoter, wherein the promoter is operably linked to said nucleotide sequence.

4. The method according to claim 2, wherein the recombinant DNA construct further comprises a strong constitutive promoter in front of a transcribed cassette comprising a nucleotide sequence as defined in claim 2, followed by a plant functional intron, and followed by the nucleotide sequence as defined in claim 2 in reverse orientation.

5. The method according to claim 1, the method further comprising regenerating a transgenic plant from said one or more regenerable cells.

6. The method according to claim 1, wherein the transgenic tree is a hardwood tree and wherein the hardwood tree is selected from the group consisting of acacia, eucalyptus, hornbeam, beech, mahogany, walnut, oak, ash, willow, hickory, birch, chestnut, poplar, alder, maple, sycamore, ginkgo, a palm tree and sweet gum.

7. The method according to claim 1, wherein the transgenic tree is a hardwood tree and wherein the hardwood tree is a plant of the Salicaceae family.

8. The method according to claim 1, wherein the tree is a conifer.

9. The method according to claim 8, wherein the conifer is selected from the group consisting of cypress, Douglas fir, fir, sequoia, hemlock, cedar, juniper, larch, pine, redwood, spruce and yew.

10. The method according to claim 1, wherein the tree is a fruit bearing tree.

11. The method according to claim 1, wherein the tree is selected from the group consisting of bamboo and rubber plants.

12. The method of claim 1, wherein the one or more regenerable cells are from a *Populus tremula* tree.

\* \* \* \* \*

SEQUENCE LISTING

```
<160> NUMBER OF SEQ ID NOS: 60

<210> SEQ ID NO 1
<211> LENGTH: 1440
<212> TYPE: DNA
<213> ORGANISM: Populus tremula x tremuloides KR121

<400> SEQUENCE: 1
atgagcttgc aggtggttct agcgttactt gtggttgcct tcattagctt cagaggtgct        60
gagagcagaa aggcgaggat tttggactcc tttgagtaca gtgccataaa ttgcagggct       120
cacagtgcat cattaactga tttcggagga gttggggatg gaacaacgtc gaacactaaa       180
gcatttaagg atgcaattga tcatttgagt cagttttcat cagatggtgg ctctcagctc       240
tttgttcctg ctggaaaatg gttgactggt agcttcagtc ttaccagcca cttcacactc       300
tacctacaca aggatgctgt gcttcttgcc tctcaggaca tgcaagaatg gccagtgatg       360
aaacctctgc catcatacgg cagagggagg gatgcagcag ctggaaggta cagcagtctc       420 atatttgaa cgaacctcac tgacgttatt attacaggga acaatggcac aattgacggc       480
cagggagctt tctggtggca gaacttccac aagggcaagc taaaatacac caggccttac       540
```

```
ttaattgaga tcatgttctc agatactatc caaatttcaa atctgacgct cctgaattcc    600
ccgtcttgga atgttcatcc tgtttacagc agagatattc ttgtgcaagg cattaccatc    660
atcgctccaa tctcatcacc aaataccgat ggaattaatc cagattcctg tacaaacact    720
aaaattgaag attgttacat agtttctgga cgcgattgtg tggcagttaa aagcggttgg    780
gacgagtacg ggattgcgtt tggaatgccc acaaagcaac tagtcatcag acggctcacg    840
tgcatctctc catacagtgc cacgattgct ctagggagtg aaatgtcggg tgggatagaa    900
gatgttagag cagaggatat cacagccatc cacacagaat ctggggtcag gatcaaaact    960
gctgtaggga gaggagggta tgtgaaagac atatacgtga agagaatgac tatgcatacc   1020
atgaaatggg tcttttggat gactggaaat tatgggtcac atgctgataa gaattatgac   1080
ccaaatgcac tgccattgat tcaaggcatt aattacaggg acatggttgc cgataatgtg   1140
acaatggcag ctagattgga gggcattgca ggcgatccat tcaaggaaat ttgcatctcc   1200
aatgttacaa tcggattggc accgaaggca agaaggtgc cgtggacctg caccgaaatt   1260
gaggggatga caagcggggt aagtccacgg ccatgtgatt tgctaccgga tcaggggcca   1320
gagaaaatca catcctgtga tttccctccg gagaatatac caatcgactt ggtgcagttc   1380
aagatgtgct ccttcggaat gagttacatg tgaactttgc ttctctacta ccatcaagca   1440
```

<210> SEQ ID NO 2
<211> LENGTH: 1899
<212> TYPE: DNA
<213> ORGANISM: Populus tremula x tremuloides KR125

<400> SEQUENCE: 2

```
taaatgaaac atggtactgg aggttaaaag acccaccatg agcaataaca ggaggggggtt     60 ttatgttaga atgaaactat tacacagaca tgctggactt caacaacaag agaagaagaa    120
gaatctttgt ttcaaatatt acaaatggct tctttggttt tctcttcttc tatatttcct    180
tagctcttgc ttcttcaccc acaaacccat tcccctctcc aaaacccatg tctcagaatc    240
taaaactgtt gtttcccgtg ccctctttga atcctccaac tccactttca ttcaacagag    300
caagaacatc aatcgaggat tattaaagga tttgaaggta tacatatatg agttgccatc    360
aaaatacaac acggactggt agcaaatga gaggtgcagc aaccatttgt ttgcatcaga    420
agttgccatt cataaagcac tatcaaacag tcttgatata cggacgtttg acccatacga    480
agctgatttc ttctttgttc ctgtttacgt gtcctgcaat ttcagcaccg ttaatgggtt    540
ccctgcaatt ggtcatgcaa ggtccttatt atcctctgcg gtgcagctca tttcctctaa    600
ctatccattt tggaaccgct ctcaaggatc tgatcatgtc tttgttgcct ctcacgatta    660
cggcgcttgt ttccatgcca tggaggagag agctatggaa gatgggatcc cagagttttt    720
gaagaggtcg atcatattgc agactttttgg tgtcaaattt aaccatccat gccaagacgt    780
tgagaatgtc gtgataccac cttacatctc gccggaaaga gtacgacaa cactcgagaa    840 ttatccgctg aacggccggc gggacatttg gccttctttt agaggcaaaa tggaagtgca    900
ccccaaaaac attagtggac gatattcag caagaaagtg aggacggtaa tatggagaaa    960
atacagcggg gaccggaggt tttatttgca aggcacagg tttgccggtt accagtcaga   1020
aatcgtccgg tcagtgttct gtttatgccc cttgggatgg ccccatggaa gcccgaggct   1080
ggtggaatct gttgcattag ggtgcgtgcc ggtcataatt gcggatggaa tccgttgcc   1140 cttccccact gctgtccggt ggtcggagat atccctaacc gtggccgaaa aggacgtggc   1200
```

| | |
|---|---|
| caatctagga actctactcg atcacgtggc agctaccaat ttgtcagcca ttcagaaaaa | 1260 |
| cttgtgggac ccagacgtta ggcgggccct ccttttcaat gatcgagtgc aggaaggcga | 1320 |
| tgccacgtgg caggtgcttt atgccttggc acggaagctg acaggtcgt acagaaccgt | 1380 |
| gaggcttcca aaccaatagt ggttcgacac gttgaaggta cttttttggg gacccaagtg | 1440 |
| ccagctatgg gggtccgctt tgccagcta agaaacatgg agcacagctg attttttaat | 1500 |
| gttttttcttg gattgatcaa aactacggga attttttagag caacgaggt ggggtccagc | 1560 |
| ctctgcagag tttaagatta tctgcagaaa ttttttggtgg tcccgtgact tgctcggtga | 1620 |
| gttggctgac tgtgattgat ggggctgaac ggtacatata attgtaaagc aatactgtag | 1680 |
| agtagatgat ggggaggttt atgttttgag aaataatgag agaataaatg caaaaatagg | 1740 |
| ccctgtaaat actaataagg agtcgaagtc gattgcaatt tactgaaaac ccaacccagt | 1800 |
| atcaaacttt actatttcat ttgttttttt aaatcagatt tatgtatttt ttattcattt | 1860 |
| atatttgatc ttagacaatg tcgtagtaaa catgataaa | 1899 |

<210> SEQ ID NO 3
<211> LENGTH: 1440
<212> TYPE: DNA
<213> ORGANISM: Populus tremula x tremuloides KR129 B

<400> SEQUENCE: 3

| | |
|---|---|
| atgagcttgc aggtggttct agcgttactt gtggttgcct tcattagctt cagaggtgct | 60 |
| gagagcagaa aggcgaggat tttggactcc tttgagtaca gtgccataaa ttgcagggct | 120 |
| cacagtgcat cattaactga tttcggagga gttggggatg aacaacgtc gaacactaaa | 180 |
| gcatttaagg atgcaattga tcatttgagt cagttttcat cagatggtgg ctctcagctc | 240 |
| tttgttcctg ctggaaaatg gttgactggt agcttcagtc ttaccagcca cttcacactc | 300 |
| tacctacaca aggatgctgt gcttcttgcc tctcaggaca tgcaagaatg ccagtgatg | 360 |
| aaacctctgc catcatacgg cagagggagg gatgcagcag ctggaaggta cagcagtctc | 420 |
| atatttggaa cgaacctcac tgacgttatt attacaggga caatggcac aattgacggc | 480 |
| cagggagctt tctggtggca gaacttccac aagggcaagc taaatacac caggccttac | 540 |
| ttaattgaga tcatgttctc agatactatc caaatttcaa atctgacgct cctgaattcc | 600 |
| ccgtcttgga atgttcatcc tgtttacagc agagatattc ttgtgcaagg cattaccatc | 660 |
| atcgctccaa tctcatcacc aaataccgat ggaattaatc cagattcctg tacaaacact | 720 |
| aaaattgaag attgttacat agtttctgga gacgattgtg tggcagttaa aagcggttgg | 780 |
| gacgagtacg ggattgcgtt tggaatgccc acaaagcaac tagtcatcag acggctcacg | 840 |
| tgcatctctc catacagtgc cacgattgct ctagggagtg aaatgtcggg tgggatagaa | 900 |
| gatgttagag cagaggatat cacagccatc cacacagaat ctgggggtcag gatcaaaact | 960 |
| gctgtaggga gaggagggta tgtgaaagac atatacgtga agagaatgac tatgcatacc | 1020 |
| atgaaatggg tcttttggat gactggaaat tatgggtcac atgctgataa gaattatgac | 1080 |
| ccaaatgcac tgccattgat tcaaggcatt aattacaggg acatggttgc cgataatgtg | 1140 |
| acaatgcag ctagattgga gggcattgca ggcgatccat tcaaggaaat ttgcatctcc | 1200 |
| aatgttacaa tcggattggc accgaaggca aagaaggtgc cgtggacctg caccgaaatt | 1260 |
| gagggggatga caagcgggt aagtccacgg ccatgtgatt tgctaccgga tcaggggcca | 1320 |
| gagaaaatca tcctgtgta tttccctccg gagaatatac caatcgactt ggtgcagttc | 1380 |
| aagatgtgct ccttcggaat gagttacatg tgaactttgc ttctctacta ccatcaagca | 1440 |

<210> SEQ ID NO 4
<211> LENGTH: 474
<212> TYPE: DNA
<213> ORGANISM: Populus tremula x tremuloides KR140

<400> SEQUENCE: 4

```
atgcgggatc atatggaaag atttgtagtt cttccattct ccatcgcctg tgcctctcac      60
tccagtgttg atgtggcctc cagaggacaa gaagggagg aaagctcttg taaagaaaag     120
acgaagaaca atacatttgg tttcctgctg gctcttccaa agccttgcat atccagtagc    180
attcacaaat tgattagggg cattaagact ctctcccaag tatttgtgta caagaagaa     240
gacgaggagc taatggaaag agagatggaa atcggatatc caactgatgt gaagcatgta    300
acacacatag gattggatgg aactactatg acaaatccta ttaagggctg gaatgcctg     360
aaatctccag aaataattcc attcccttca tttactttaa ggcagttcga gcttgcaatg    420
gctgcacaag ctcatggacc tcttgttggg gtcgatcatt ccaagcttgt ttga           474
```

<210> SEQ ID NO 5
<211> LENGTH: 2154
<212> TYPE: DNA
<213> ORGANISM: Populus tremula x tremuloides KR152

<400> SEQUENCE: 5

```
atgccttcaa gacccttgtc tccaagtttt gaccatccta gacccagttt cttaaccaaa     60
accaggatct tgttttgac actcacaatc tcagcctctg tgattttgat tcttaccatt    120
ctttactttg tttaccatct ttggtgcacc cttgtcaatc gttcaagaac catccctttt    180
gactctagtg ctcccttaaa gcttcaaaga ttttcataca aggagttaaa gattgccact    240
aatgattttg atgatgcgaa tattattggc aagggtggtt ctgctactgt ctttagaggc    300
attgcaaggg atgcaagtt atacgctatt aagagactcg atgctctttc tttacaatca    360
gagagagagt ttcagaatga gttgcagatt ctcggtggtt taagatcacc tttcttggtt    420
attcttttgg ggtactgtgt tgaaaagaat aagcgcttac ttgtttacga gtatgtgcca    480
aataaaagtt tgcaagaatt gctgtttgga gatggtcatt tgagtctgtg ctgggagaga    540
aggtttaata tcattcttga tgttgcaaaa gcacttgagt ttttgcaccct tggatgtgac   600
cctccagtga ttcatgggga tgttaagcca agcaatgttt tgcttgattt tgatatgaga    660
gcaaagattt cagatttttgg gttatcaagg attaaggtgg aggggagtt tggagtggat    720
ttgtttagtc aagatttggg aaagagtcaa gagctatgga gagtcaaga gctttcaggg    780
aatttgactc cagaaacacc agcaattggt acccctgtgg agagttgtca cgaggtagac    840
tttgctcttg ctttacaagc ttcttcttcg tcaaaaaaca gtagaacatg ttataatgtt    900
aaggctttga acttgaattc tgtgaattat aacgccaata ttgcgggtga gagtgatgtc    960
aaggtaggga tgggaaggg gaaggaggtt tcaagtgttg atattggcgg ggatgattgg   1020
aattgtagat ttgtgccgta tgatgatgag ttttgtagta atgatcatag taaggagttg   1080
aattgtaata gcttctctgt tgttgacgat tcagctagta gtaaacaatg gggaaaggat   1140
tggtggtgga gacaggatgg gagtggtgaa ttgtgtagta agattatgt tatggagtgg    1200
atagggagcc aaatctgccc ctcaacaaat ccggactggg aagatgaaaa gaaaagtact   1260
cctgaaagaa cagaaatgcg tcgttctgtc gcattagata aattagctga tgcaaatgaa   1320
cctccacgat taaagatttt caagtttgaa atcttgtta gaggattcga gaagaaagaa   1380
```

-continued

| | |
|---|---|
| tctagaggca ggaaaaaccg tcggaagaaa aataggaaga tgcaagagtg gtggaaagaa | 1440 |
| gagcacttgg atgagattaa caagaagggt agtaagctga agaatcttga aacaaagtgg | 1500 |
| agaaaagggt ttaaaatccc acattttgat ctcggtcgca ggtttcgttt tcacaggcga | 1560 |
| aagaaattgg gagaacagaa ccaaaatgag actgatcaaa atgggagtt cagtttcaga | 1620 |
| aggggatgga agaaaaagaa cttgcaatct gctggaagtg atatgtggag tggggatctt | 1680 |
| ttcagtcgtg agttaagcag cacaacaagc atgagaggca ctctctgtta tgttgcgcca | 1740 |
| gaatatggtg ggtgtggata cttgatggag aaggctgata tatacagctt aggggttcta | 1800 |
| atcctcgtga ttgtctccgg taggaggcca ttacatgttc ttgcttcacc aatgaagctt | 1860 |
| gaaaaggcaa atttaataag ttggtgcagg cagttagctc aaactgggaa catcttagaa | 1920 |
| cttgtagatg agagaatgaa ggatgaacac aataaggagc aggcaagctt gtgtataaac | 1980 |
| ttggcgctga catgcttgca gaggatgcct gaattgaggc cagatattgg agagatagtg | 2040 |
| aagattctga aggggagat ggatctaccg catcttcctt tcgaattttc tccctctcca | 2100 |
| ccttccaaat tgtttagtag gtcaaggaga aacaaaaaat ctaatgcaga gtag | 2154 |

<210> SEQ ID NO 6
<211> LENGTH: 2520
<212> TYPE: DNA
<213> ORGANISM: Populus tremula x tremuloides KR163

<400> SEQUENCE: 6

| | |
|---|---|
| atgtgcaata gcagtaatgc gttgctggtt ttattgtttt tggtgagttc tttggcctgt | 60 |
| tctgtcactg cctctgtgtc ttatgactct aaggccatca ccattaatgg ccaaagaagg | 120 |
| attcttattt ctggatccat tcactaccca agaagttccc ctgagatgtg ccagatctt | 180 |
| attcagaagg caaagaagg aggactggat gttattcaga catatgtttt ttggaatggg | 240 |
| catgaacctt caccaggaaa gtattatttt gaggggaact atgatctggt caagtttgtt | 300 |
| aagctggcga aggaagcagg cctttatgtt catctcagga ttggacctta tatctgtgct | 360 |
| gagtggaact ttgggggttt cccagttgg ctcaagtaca ttccaggcat caatttcaga | 420 |
| acagacaatg gccctttcaa ggctcaaatg cagaagttca caacaaaggt tgttaacatg | 480 |
| atgaaagcag aaaggttatt tgagactcaa ggtggtccaa taattctctc ccagattgag | 540 |
| aatgaatatg acccatgga gtatgaaatt ggttcacctg gtaaagctta caccaaatgg | 600 |
| gctgcagaaa tggctgtagg gtctccgtact ggtgtcccat gggtcatgtg caagcaagat | 660 |
| gatgccccag atcctattat caacacctgc aatggtttct actgtgatta cttctctcca | 720 |
| aacaaagctt acaaaccaaa gatgtggact gaagcttgga ctggctggtt tacccaattt | 780 |
| ggtgccccag ttcctcaccg accggctgaa gacatggcat tttcggttgc aaggttcata | 840 |
| cagaaggggg ggtcattcat aaaactattat atgtatcatg gagggacaaa ttttggccga | 900 |
| actgctggtg gtccttttcat tgcaacaagt tacgattatg atgctcctct tgatgaatat | 960 |
| ggactgttaa ggcagcctaa atggggccat ttgaaagatt tgcatcgggc aattaagctg | 1020 |
| tgtgaacccg ctttagtatc tggagatgca actgtgatac cacttggaaa ttaccaagag | 1080 |
| gctcatgtat tcaattataa ggccggaggt tgtgcagcat tccttgcaaa ttaccatcag | 1140 |
| agatcatttg caaaggtgtc atttaggaat atgcattata acctgcctcc atggtccatc | 1200 |
| agcattcttc cagattgcaa gaacactgtt tacaacactg caaggggttgg agctcaaagt | 1260 |
| gcaaggatga agatgacccc tgttcctatg catggagggt tctcttggca agcatataat | 1320 |
| gaagagccgt ctgcaagtgg tgatagcaca ttcactatgg ttgggttgct ggagcaaata | 1380 |

```
aatacaacta gagatgtttc agactatttg tggtacatga cagacgttca tatcgacccc      1440
agcgaaggct ttctgaggag tggaaaatat cctgttcttg gtgttctatc agctgggcac      1500
gctttacatg ttttcatcaa tggtcaacta tcagggaccg cctatggaag tttagatttc      1560
ccaaagttga catttactca aggtgtaaag ttgagagctg cgtcaacaa aatttctctt       1620 ctcagcattg ctgttggtct cccgaatgtt ggcccacact ttgagacatg gaatgctggt      1680
attcttggac ctgtgacgtt gaatggtctc aatgagggaa gaagggactt gtcctggcag      1740
aagtggtctt acaagattgg tcttcatggg gaagcattgg gtctccattc aatcagtggg      1800
agttcctcgg ttgagtgggc agagggatct ttggtggccc aaagacagcc actgtcatgg      1860
tataaaacta ctttcaacgc tcctgctggg aattccccctt tggcattgga tatgggcagc    1920
atgggaaaag gccagatatg gataaatgga caacatgttg gacgtcactg gcctgcttat      1980
aaagcatctg gaacatgtgg ggactgtagt tatattggaa cttataatga aaagaaatgc     2040
tcaactaatt gtggcgaggc ttcccagaga tggtatcatg tccctcagtc atggctaaag     2100
ccaacaggga acttgctggt tgtgtttgaa gaatggggtg gagatccaaa tgggatttct     2160
ttggttagaa gagatgtaga cagtgtgtgc gctgatattt atgagtggca gccaactttg     2220
atgaattatc agatgcaagc atctggtaaa gtcaataagc cactgaggcc taaagctcat     2280
ctgtcatgtg gccctggaca gaaaatcaga tcaatcaagt ttgccagctt tgggacacca     2340
gaagggtttt gtggtagcta tcgccaggga agctgtcatg ccttccactc ttatgatgct     2400
tttaacaatc tttgtgttgg gcagaattca tgctcggtga ctgtagcacc tgaaatgttt     2460
gggggagatc cttgcctgaa tgtcatgaag aaactagcag tagaggccat ttgcagctga     2520

<210> SEQ ID NO 7
<211> LENGTH: 654
<212> TYPE: DNA
<213> ORGANISM: Populus tremula x tremuloides KR221
<220> FEATURE:
<221> NAME/KEY: misc_feature
<222> LOCATION: (1)...(654)
<223> OTHER INFORMATION: n = A,T,C or G

<400> SEQUENCE: 7
ctcagccaga tgtgtcctga gcttgcttgg atgacaacaa gcaactggaa ttattgctgc       60
attaactata ttataagaag cagttactca gtggggattc tggtgggcat ttgctgtcat      120
ggacactacc agatgagagc ttgctgaacg tcatctaatc aggggtgaga gggggggaaa      180
ctgatttaag cgtgattgtt tcagctcgtg gcagctattt attatctatt gaaatcctat      240
gcgggttttg tctgccacca cggcaaagga agtaaaggat tctatgttcg taatacattg      300
agaagggaga acaaggcagc aggctggcct gggattgaaa gaggacagca aaagaagat       360 gagatcttta tagatgactg ataaatgtcg atttcctggc aagcatgaag actctcgtgc      420
caggcttctt attgagaatg gaaagtggag tcttgcttct tgttgtactc tgggttcttg     480
gcgaggacnt tttgatttgc acgtgacaga gtcattaggt gtttgtcca tgtncatggt      540 gggattaccc acagtgtgtt ntgagttgtn tagagaaaag tgtccccagg gatggagact     600
gtgaccccct ggccagttta ttggctattg tatcctcgct tattttttaa atgt            654

<210> SEQ ID NO 8
<211> LENGTH: 880
<212> TYPE: DNA
<213> ORGANISM: Populus tremula x tremuloides KR224
```

<400> SEQUENCE: 8

```
gccaaataga gattttttcg agctagctgt atagttgaag agaagctgaa gaggaagaga      60
tggcagagca ggaggtgaag aaggtagagg ctgtaacgcc cgtggctcca gctccagtgg     120
aaactaaaag tgatgtggcc gatgggaaag ttacggctcc accacctcca gtggctgcag     180
agaaacagaa ggcagctact gctgctgagg aatcaaaagc tcttgctgtt gttgaaaaga     240
cagaacctgc tccgaagaag gtttcaggcg atcaattga cagagatgta gctcttgctg     300
accttgaaaa agaaaagaga cttctccttta tcaaggcatg ggaagacagc gagaaaacta     360
aagccgagaa caagtctcag aaaaatttct ctgctgttgc tgcctgggag aacagcaaaa     420
aggcagctct ggaagccaaa ctgagaaaga tggaggaaaa actggagaag caaaaggcag     480
aatatgcaga gaaaatgaaa acaagattg cttta attca caagaagct gaggaaaaga     540
aggcaattgt tgaagccaaa cgcggggaag aggtcttaaa ggcaggggag acggctgcaa     600
ataccgtgc tactgggcaa accccaaaga agctccttgg ttgcttctga agtcgcaact     660
ttaggagcct agcatggaag cggaaagttg aatcatcatt cttcctctgc atatagtgtt     720
ttttaactcc ttgttttttct tgcttgcttg cttcttcttt ttttcccaca tggtttcatg     780
tcttctttca ttaaacatcg gaaaatttaa atattcagtg tgtttatgta taggaataca     840
atatttgatc tgtgagaaac aagtttaaca tgtttgtgaa                            880
```

<210> SEQ ID NO 9
<211> LENGTH: 1020
<212> TYPE: DNA
<213> ORGANISM: Populus tremula x tremuloides KR235

<400> SEQUENCE: 9

```
atggaacttg ggcttgtgga gttgttgaga gcagcttgga ttgcagggac actgcctata      60
cttatagctt cactgccatg ttcttggctg ggttctttc atggacttgt tttggggttt     120
gcaaggagag gaaagatcat gcaatcatca tctcatcgta aattcactgt tccccaaaga     180
ttctttactc atttctatgt ggtggctgtg gcgtggacaa ctctcttgct tcttggaaca     240
tcgatatatg cttatagaat gacaccaata gtttctgagc cgttttttcta ctctgatctt     300
ggcagctact tggcaggacg atcaaacata ttctcatttc atcgatcacg ttgatgagt     360
ttagagaata gatacagggt ttggcattct gtgtttctgc ttttgctaat ggaagttcaa     420
gtctcgaggc gtcttttcga gacagcatat gtatttaatt atagcgcctc tgctcggatg     480
cacatttttg gctatcttac tggcttattc ttctacacag cagcgcctct gacactctgc     540
tgtacctgtg cacccgaagt actcaaattt ggcataaatg aagtgtctga gttcattctt     600
aaaggcacaa gctcaatgca aaacattgaa tttcactggt gggactttgt taacccttta     660
ttgaagcttg gatggtgcca gtggattggc gcagttatat ttctttgggg ttggattcat     720
cagcatcgtt gccatgcaat tcttggctca ctaagggaac acgtgggaaa ggctgatgaa     780
tatgtaattc cccgtggtga ttggttcgag attgtttcat ctccacacta tttggcagag     840
attgttatat atgctggcat ggttttttgct agtggagggg cagacctcac catttggtta     900
gttttttggat ttgtggtgtc aaatctggtg tttgcagctg cagaaacaca caggtggtat     960
cttcagaaat ttgacaatta tccaagcaac cgtgttgcaa ttattccatt tttatgttaa    1020
```

<210> SEQ ID NO 10
<211> LENGTH: 1344
<212> TYPE: DNA
<213> ORGANISM: Populus tremula x tremuloides KR240

<400> SEQUENCE: 10

```
gagactgaga tgatgaagga aaggttttca aaattgctgc tcggagaaga tatgtctggt      60
tgtggaaatg gggtttgtac agcattggcg atctcaaatg ccattactaa tctatgcgct     120
accttgttcg ggcaactatg gaggttggag cctctaccac ttgagaagaa agctatgtgg     180
cgaagagaga tggaatggct tctttgtgtg agtgatcaca ttgtggagtt gatgccttct     240
tggcagacat ttccagatgg aagcaagctc gaggttatga cctgcggacc tagatcggat     300
ctctacataa atcttccagc tctgcgcaaa ttggacaaca tgcttcttga gatattagat     360
agttttgaca atactgagtt ctggtacgtc gaccaaggga tcctggcccc tgatactgat     420
gggtcagcct ctttccgaag aaccctgcag cgccaagaag agaagtggtg gctacctgtg     480
cctcaggtac ctcctggagg cctccatgaa aattcaagaa agaagttgca gcacaaacgt     540
gattctacaa atcaaatatt gaaagctgcc atggctatca acagtattac tttagctgaa     600
atggaaatcc ctgaatctta cttggaggct cttccaaaga atggaaaagc cagcctagga     660
gacctcatct atcgatatat ttcttcagat caattttatc cagaatgtct ccttgattgc     720
ctagatttgt cttctgaaca tcaagctata gaacttgcga accgagtgga ggcctcaatc     780
tatatatggc gcaaaagaac caattataaa cctgccagta gtacaaatcg atccagttca     840
aagtcgtcat gggaattggt caaggaactg atgattgatg cagacaagag ggaattgctt     900
gctgatagag cagaaagcct cctactttgc ctgaagcagc gattccctgg tcttccacag     960
acaactttgg atatgagcaa aatccagtac aacaaggatg ttgggaaatc cattttggag    1020
agctactcga gagtcttaga gagcttggca tttaatattg tggcccgaat tgacgacctg    1080
ctctacgtgg atgatttgac aaaacattcg gatcatttct cttcaatctc taaagtcagt    1140
gtgattgctc acaaaagtgt aacaattcca tactcggtcc ccgtctcaaa cactccatac    1200
aaaacagctt tcaacacacc aagcttttca ccaggtcaac aacgaataag ccctgcaaag    1260
ggagaccgat cgcctttcat gaccagtggc aaaattcctc agcgtggttt aggcgtaaaa    1320
aaggtattga cagagtatct cagt                                           1344
```

<210> SEQ ID NO 11
<211> LENGTH: 1026
<212> TYPE: DNA
<213> ORGANISM: Populus tremula x tremuloides KR242
<220> FEATURE:
<221> NAME/KEY: misc_feature
<222> LOCATION: (1)...(1026)
<223> OTHER INFORMATION: n = A,T,C or G

<400> SEQUENCE: 11

```
agtcccattc tttttcctag ccccaagttt nntnttgagg ggtgataaaa aatgaaccaa      60
gagatgaatg gtgttgacac tgagattgat cagaaccacc aagagaatgt gcaagagaaa     120
atcgattatg tgtttaaggt ggtggtgatc ggtgactctg cagtgggcaa gacgcaaatt     180
cttttccaggt ttaccaagaa tgaatntctg ctttgattca naagtctacc atcggtgtcg     240
anttccanga ctaggactgt catcattaaa gacaaggtca tcaaggctca gatctgggat     300
actgctggcc aagaaaggta ccgggcagtg acaagcgcat actataggg gcactatgg      360
gccatgttag tctacgacat taccaagaga ccaacgtttg atcatgtggc taggtgggtg     420
gangagctcc gagcccatgc tgacagctca attgtgatca tgctgatcgg aaacaaggct     480
gatcttgtgg acctcagggc agttccaaca gaagacgcgg tggaatttgc agaggatcaa    540
```

```
ggcctctttt tttctgagac atcagcccct agtggtgaca atgtggacgg tgcattttc      600 aggctgctag aagaaattta cggtgtgatt tgtaagaagt cattggaatg tggcaatgga     660
aaaccccatg ctgctgatgc cataacgctt agaggttcta agattgatgg catatcaggg    720
acggatctgg agattagtga gatgaagaaa ttatctgctt gctcgtgttg atttgatcat    780
ttttcttgtg aattgtgtac tataagactt caccactccc atgttcttaa ttgattctgt    840
ggctttcttt ggaaagtggt gatcggtcgt gtggtgaggg tggcaagttt tttcttttct    900
gtgacctgtc aagattttag cagtattgta cttgtcttac agaacccatg aattgtggtt    960 ttttatatg tattgatttg gatggatggt tttccttttc cttcaaaaaa aaaaaaaaaa    1020
aaaaaa                                                               1026
```

<210> SEQ ID NO 12
<211> LENGTH: 820
<212> TYPE: DNA
<213> ORGANISM: Populus tremula x tremuloides KR292
<220> FEATURE:
<221> NAME/KEY: misc_feature
<222> LOCATION: (1)...(820)
<223> OTHER INFORMATION: n = A,T,C or G

<400> SEQUENCE: 12

```
atatgaacgc ttctctatgg gttttgtcatg tggagaggat gattttgaaa agaatggaag   60
tcatgaagtt ccgttaatag ttgatagcag agggactaga gtcagcggtg ctatatgga   120 ttnacaacat cttcatcatg cagttganta cgaggtcgaa ttctggccag ttgaacaccc   180
aatgaaacca caggatgaag atcgtcctgt caaatgtcca atgccaacct cttctgntat   240
caagaatgga aggncgcatg aggagagatt agagaagaga gcggacgact ccaactacct   300
gcggtaatga acaaacaagg cattgttgtg gtggctgcag agcccaagt ccgagcagtg    360 cgtaaaaggc accatacact tacccgccag gaccaccgtg taatagcacc tgatctaaca   420
aggatggctt cnacntntcc tgctctgcca anctcagaac gtcaccnatt tttcaaatgc   480
ttcaagaact cngacaagtt cgatcagtat taaaaggta taaagaataa attaggaaac    540
ccacatttcc gctccatcta gctttaatag ctacttttca atccattgcg gagcggtcaa    600
tgaattcttc atgattgta tttcgggcca atagggaaag aaatatcata gatatgcggt     660
ataagaagca ctcttattgt actagatttt tatttttat atattctgta gaatgtgtct    720
tccagcctaa ttgtaggttt cctttatcat ttctttgttc agatttggat ggataattag    780
catgacactc tgcaatacca aaaaaaaaaa aaaaaaaaaa                           820
```

<210> SEQ ID NO 13
<211> LENGTH: 1149
<212> TYPE: DNA
<213> ORGANISM: Populus tremula x tremuloides KR313

<400> SEQUENCE: 13

```
atgcctcagt tggtttcttt taaggaggaa agtactaaag ttgctgatct tcttgattct     60
gagaagaaag cacttcaaga atttaagcag cttgttcaag aagcacttaa caagcatgaa    120
tttatgacac cagaagaagt atcaatctgg ggaataccac ttcttgctga tgacagaagt    180
gatgtgattc tcttgaaatt tctcagagcc agagatttca aggtgaaaga tgcattcacc    240
atgctcaaga gcacaattcg ctggagaaag gagtttggca ttgatgaatt gcttgaacaa    300
gatttaggct tgatgatttt ggggaaggtg gtatttatgc atggtcttga taagagggga    360
cacccagtgt gctataatgt ctatggagaa ttccaaaaca aggaacttta caagaattca    420
```

```
ttttctgatg aggagaagag gcagagattc ttaaggtgga ggattcaatt cctggaaaaa      480
agtatcagga cattggattt cagtcccggt ggaatttcca caattgttca ggttaatgac      540
ttgaaaaatt ctcctggacc agctaagaga gagcttagac aagctactag acaggcactt      600
caattgcttc aagacaacta ccagaatttt gtggccaaac agatcttcat caatgttccc      660
tggtggtacc taacagtaaa tagaatgata agtccatttt taacccagag gaccagaagc      720
aagtttgtct ttgttggtcc ttccaaatct gccgaaaccc ttatcaggta catagccgct      780
gagcaaatac cagtgaagta cggaggacta agcaaagatg gtgaatttgg ctcagctgat      840
gctgttactg agattaccgt gaagccagca gcaaagcaca ctgtagaatt cccagttact      900
gagacatgcc ttttaacatg gaagtgagag gttgcgggat gggatgtgag ctatagtgca      960
gaatttgtac caagtgctga agatagctac acagtgatca tccaaaaggc tagaaaggtt     1020
gctgcaactg aagaaccagt ggtttgcaac agtttcaaaa ttggtgaacc tggtaaagtt     1080
gttctcacca ttgacaactc cacatccaag aagaagaaga agctcctcta tcgcttgaaa     1140
accaagccc                                                             1149

<210> SEQ ID NO 14
<211> LENGTH: 1511
<212> TYPE: DNA
<213> ORGANISM: Populus tremula x tremuloides KR318

<400> SEQUENCE: 14
gcataataat tgtttaagag aagaatattt gtctcgcatt ggcgctccca tgtcttctaa       60
atcactactt tcttttgtga tttatggttt tcttcttctt tccccttgta actctttgaa      120
ggacaatgcc gatgaaggaa cgagagcata tttcatact  ctcaaaatca gttctctccc      180
atcaacagaa gtctgcaagg aatcttccaa agctctcaac gagggttcat catccctaaa      240
attagtacac aggttcggtc catgcaatcc acacagaaca tcaactgctc cagcatcatc      300
cttcaacgaa atcctccgtc gagacaaact tcgagtggac tcaattattc aggcccggcg      360
ttcaatgaac ttgaccagca gtgttgagca catgaagagt agtgtcccgt tctatggtct      420
atccaaaatc actgcaagtg actatattgt caacgttgga atcggcacgc caagaagga       480 aatgccactt atatttgaca caggcagtgg tctcatttgg actcaatgta agccgtgcaa      540
ggcttgctat ccaaaagtac ctgtgttcga tccaaccaag tcagcttcat tcaaaggcct      600
tccatgttcc tcaaagctat gccaatcaat caggcaagga tgctcctctc cgaagtgcac      660
ctacttaact gcatatgtag acaacagcag ctccacagga actttggcca ccgaaacaat      720
atcctttagc catttaaagt acgacttcaa gaacattttg attggatgca gcgatcaagt      780
atctggtgaa tcacttggag aatctggtat aatgggacta aaccgctcac ctatatcttt      840
agcatcacaa actgctaata tatacgacaa actcttctct tattgtatac cgtcaactcc      900
tggctcaact ggtcatctta ctttcggcgg caaagtgccg aatgatgtca gattctcccc      960
agtatctaaa acagcaccat cttcggacta cgacatcaaa atgactggaa ttagtgttgg     1020
aggccgtaaa ctattgatag atgcatcggc ttttaagatt gctagcacca tcgactctgg     1080
tgcagtgctc actcggctgc ctccgaaggc atactcggca ctgaggtcag tgttccgaga     1140
aatgatgaaa ggttatcctt tgttggacca agatgacttt ctagacacat gctatgactt     1200
cagtaattat agcacggttg caataccttc gattagtgtg ttcttcgaag gtggcgtgga     1260
gatggatatc gatgtttcgg ggatcatgtg gcaggttcca gggagcaagg tgtactgctt     1320
```

```
ggcatttgcg gaattggatg acgaagtttc aatctttggg aattttcagc aaaagactta    1380
cacagtagtc tttgatggtg cgaaggaaag gattgggttt gccccggtg gctgtgacta    1440 aaatggaaaa aaaatcttg gagcactagc tctaaattat aatatatcaa taaaatggtt    1500
tgattttaca t                                                          1511
```

<210> SEQ ID NO 15
<211> LENGTH: 1125
<212> TYPE: DNA
<213> ORGANISM: Populus tremula x tremuloides KR459

<400> SEQUENCE: 15

```
gacacctgca catcgtttag ttgattttgt tgccaggaaa gatatcgtca ccgtcatgac     60
agaagttgtc agcaatattt ctccccctcc tggttctgta gcaaccgtat cagatgcacc    120
tcccatccat tacatggtta aaatagagtc attttcgtca cttgggaaaa atgcagtgga    180
gacatatgaa tcagggggttt ttgaagctgg aggctataga tggaaattag ttctctatcc    240
gaacggaaac aagagcaata atgtaaaaga ttccatctct ctctatttag caatggttga    300
cgcaagttct cttccacgtg gttgggaggt caacgtgatt tttcggttgt ttttgcttga    360
ccaaaacaag gacagctact tggtaattca agcaggaaag gaaagacgct ttcacggatt    420
gaatcttcaa agtggttttg atcaattcat taagctttca acatttaatg atgctcgtta    480
tggattcctt ctggaagaca cttgtgtgct tggagctgaa gtatttgtct gtggagaaag    540
aagcagaggc aaaggagagg tcttatcaat gaaaaaggat cctactgctt ccaagtacac    600
ttggaagatc gtgaactttt ccaagttgga tgaaaacgc caagaatcac aaatattcag    660
caccggagat catcaatgga agatggtgct ctatcctaag ggaaaaggtc ttggaatggg    720
cacccatctt tccctctact tggctctgga tttggaaacc ctcctgctg gttgcagagt    780 atatgcggat tacaccttgc gccttgtgga tcaagtctat aacagacaga tcgactggta    840
ttataaagct aaaagctggt ttggtgcctc aagcttagca aatggatggc caagatatgg    900 tccctgagt ttatatcagt caaacgatta ccttttgcc aaggacattt gcgtaattga    960
agcagaggtc ataatacttg gaattggttc tcccttttag ttatgatttt attttattt    1020 ttattttcaa tcagaaatat attggatatc atgtaaagaa tttcatcgac tttactaatg    1080
ggaaggtact ttatgtaaaa aaaaaaaaaaa aaaaaaaaa aaaaa                      1125
```

<210> SEQ ID NO 16
<211> LENGTH: 1693
<212> TYPE: DNA
<213> ORGANISM: Populus tremula x tremuloides KR463

<400> SEQUENCE: 16

```
atggcggaag aatccaaatc tttgcagtac acacctacat gggtgattgc tgctgtctgt     60
tttgtcattg ttctcgcctc cattttttgca gagcgaggtc ttcataaact gggaaagttc    120
ttgaggaata cggagcaaga tgcattgttt gaagccttgc aaaaattaaa agaagaattg    180
atgcttttag ggttcatttc ccttctgcta acagttaccc aaaatacaat aagccgcata    240
tgcatcccac ctcagcttgc tattaccatg ttgccatgca agagagaaac tgagagcagc    300
aaccacgaaa aaatctataa tcaagctata acaatcgac gtcatctact atctgcaact    360
aatagtgcag aacgttgtgc tcgtgagggg aaggttccat tggtgtctgt ggaagcattg    420
caccaactgc atatttcat ctttgtgttg gcaattgtcc atgttatctt ttgtgtatct    480
acaatgattc ttggaggggc aaggatacga caatggaaga cttgggagga ttccataaga    540
```

```
catccatcaa aaacattcag agatcaagca aagcatcaac atgaacacca ttattttcac      600
aagttcatta aaaacacga aaaaggatat tggagaaagt cagctgtttt aagttggctg      660
atagcattct tcaaacaatt ttatcactcc attaccaaat cagactacat tgctcttcga      720
aaaggattta tcacagcgca ttgtcccat gtgttgaatt ttgattttca caattacatg       780
atgcggacac tgcagattga tttcaaaaga attgttacca taagctggta tctgtggctc     840
tttgttgtga tgttttttgct gatgaatgtg aagggtggc attcattttt ttggctgtcc     900 ttttaccag taattcttct gctactcgtt ggcgctaagt tagaacacat tatcactagt      960
ttaggccaca gagttgcaga gatgccagtt cctatcgacg aagcacgagt acagccttca     1020
gatgaacatt tctggcttga aaacctgcc attgttcttg acttgattca gttcattctg      1080
tttcagaatt catttgagat tgcttttcttc ttctggattt ggagcacata cggattccgc    1140
tcatgcatca tggaaagagt gggctacatt gtgccaaggc ttattatggg tttagttgtt    1200
caagttctat gcagttacag caccttgcct ttgtatgctc tagtctcaca gatgggcacc    1260
agtttaagga aagggatgtt tggtcaggat gtggaagcgg caataggaat ctgggcaggc    1320
ggagcaaagg acaagaggga cccaagcgag aaccacggag cacgtatgca taaactagcc    1380
acagaatcat ctcatagtgc ggcacaagaa atggttattg atggaggcac agagctttct   1440
tctgtgaccc aagcgcctgt atcttgaaat ttggttcttc ggcaaaaagg caaaagggaa    1500
catccactta catctcctca agccttaaat ttccgcagac tcaacattta gccaaaccat    1560
tgctcataac ttaatattct gtgaatgttt tcactttgc tttatttaat ttgccagtca     1620
ttgctattct tttcatccca cgaaaaatcc ctccaccacc tattgaaccg aatgcccttg    1680
tggtaaaaaa gaa                                                       1693
```

<210> SEQ ID NO 17
<211> LENGTH: 3294
<212> TYPE: DNA
<213> ORGANISM: Populus tremula x tremuloides KR465

<400> SEQUENCE: 17

```
ctccttcttc ttctccttct ccttctcctt ctccaccttc aaatctatgc acccaccacc      60
actgcacgca ctgtatcaga atatgaagct ctcctctcca taaaatcctc catcaccgac     120
gaccctcaat catttctctc cgcatggaac tccacaaccc cactttgctc ctggactggc     180
atcacctgtg accacactgg ccgtcgagtg acctccttag acctctccgg tctcaacctc    240 tcggcactc tctcctctga cgtagcccac cttcgttacc ttcaaaatct ctccctggct     300
gtcaaccagt tttccggccc aatccctgcc tcactctccg ccgtcacttc ccttcgctcc    360
cttaacctct ccaacaacat cttcaactcc acattccctc cacagctctc ttccctcaag    420
aaccttcaag ttcttgacct ttacaacaac aacatgacag gtgggttgcc actaaccgta    480
gtggaaatgc caaatctccg gcatttacac ctcggcggta actattactc cgggaaaatc    540
ccatcagaat atggaaaatg ggggtttctt gaatatcttg ccatctccgg taacgagctt    600
gaaggtagca ttcctgttga gttaggtaac ttgactaaat tgcgtgaact ctacatcggg    660
tatttcaata cttacgaagg tggtttaccg cctgagatcg gtaatttatc cagcttggtt    720
cgttttgacg ctgcaaactg tgggttatcc ggccaaatac cgccggaaat tgcaggtta     780 cagaagctgg acacattgtt tcttcaggtt aacgggcttt cgggtcgtt aactccagag    840 cttgggagct tgaagagctt aaaatccatg gatttgtcga ataatatgtt cacggggag     900
```

```
attcctacta gttttgcaga gttaaagaac ttgacccttt tgaatctgtt tagaaacaag      960
ctgtacggag caatcccgga gttcatcgcc gagttgccgg agcttcaggt gttgcagctg     1020
tgggagaata atttcacttc aactattcca caggccttgg gtcaaaatgg aagcttgag     1080
attttagatc tttcatccaa taagcttact gggactttgc ctcctaatat gtgcttgggt     1140
aataatctgc aaactttgat cactcttagc aatttcttgt ttggtcccat tcctgaatcg     1200
cttggacaat gtcagtcctt gagtagaatt cgaatgggag agaattttct caatggctca     1260
attcctaaag ggcttttga tttgccaaac ttgagtcaag ttgagttgca agataatctt     1320
ctagctgggg agtttcctgt gattggtaca ttggctgtga atcttggcca gcttagtctc     1380
tcaaataatc gcctcacagg gtctttgcct cctagtgtcg gtaacttttc tggtgttcaa     1440
aagtttctcc ttgatgggaa caagttcagt ggttcaatcc cacctgagat tggaaggttg     1500
cagcaactta ccaagatgga ttttagccac aacaagtttt caggtcccat tgctccagag     1560
attagtcaat gcaagctgtt aacgtttgtt gatctcagta gaaacgagct ttcaggtgag     1620
attcctactg agattacagg tatgaggatc ttgaattacc tgaatctctc aagaaatcat     1680
cttgttggta gcattcctgc tcctatagcc actatgcaga gcttaacttc tgttgatttt     1740
tcttacaaca atctttctgg tttggtccct ggtactggtc agtttagtta tttcaattac     1800
acttcgtttt tgggtaatcc tggtctttgc ggtcccctatt tgggcccctg caaagatggg     1860
gatgtaaatg gaactcacca gccacgagtt aaggggccgc tctcttcttc tctgaagctc     1920
ttgcttgtta ttggcttgct tgtttgctcc attgcgtttg cggtcgcggc tataattaag     1980
gctaggtcgt tgaaaaaggc cagtgaggct cgtgcttgga aattgactgc tttccagcgc     2040
ttggacttta ctgttgatga tgttttggat tgcttgaaag aagacaatat tattggtaaa     2100
ggtggtgcgg ggattgttta caagggtgca atgccaaatg tgatcatgt tgctgtgaaa     2160
agactaccgg taatgagccg tggatcttct catgatcatg gattcaatgc tgagattcag     2220
accttgggga ggattaggca ccgacacatt gttagattgt tggggttctg ttctaaccac     2280
gagactaatc tcttggtcta tgagtacatg cccaatggga gcttaggaga ggttcttcat     2340
ggcaagaaag gaggtcattt gcactgggat accaggtata agattgctgt tgaggctgca     2400
aagggccttt gctaccttca tcatgattgc tcccccattga ttgttcaccg tgatgtgaaa     2460
tcgaacaaca tccttcttga caccagtttt gaagctcatg ttgcagactt tggccttgcc     2520
aagttcttgc aagattctgg cacatcagag tgcatgtctg caattgctgg atcttatgga     2580
tacatagctc cagaatatgc ctacacactg aaggttgatg aaaagagtga cgtgtacagc     2640
tttggtgtag ttctcttaga actcgttact ggtagaaaac cggttggaga attcggtgat     2700
ggtgtggata tagttcaatg ggttcgaaaa atgacagact caatcaagga aggagtttg     2760
aaagtcctgg acccaagact cccatcagtt ccgcttcatg aggtgatgca tgtgttctat     2820
gttgcaatgc tttgcgtgga agaacaggct gtcgaacgcc caacaatgcg agaagttgtt     2880
cagattctaa cagagcttcc gaagtcacca agctcaaaac aaggagactc agtaatcaca     2940
gagccctcgc cacattcagc cgccaccgca gcgctcgact ctcctagttc aacagctaaa     3000
gacgtcccaa aagaccatca gcagccacca cctgccgatc ttcttagcat ttgaagcatg     3060
ttgaatgggg ggttgctgtt tgttacctaa aattccagga attgtgttag tttctgtccg     3120
tctttgtgtt ccttttcatt tttctggggg ggattttctc taatgtttgc aagtattttc     3180
ttttttcttt ttgttgtaca gtaggttttg ggggaaggga ggtattttat tttcttaaat     3240
tataagactt gacttcatcc atgtagtaag tacttactgc ctgctgttgc tgac           3294
```

<210> SEQ ID NO 18
<211> LENGTH: 774
<212> TYPE: DNA
<213> ORGANISM: Populus tremula x tremuloides KR121
<220> FEATURE:
<221> NAME/KEY: misc_feature
<222> LOCATION: (1)...(774)
<223> OTHER INFORMATION: n = A,T,C or G

<400> SEQUENCE: 18

```
tggagacgat tgtgtggcag ntaaaagcgg ttgggatgag tacgggattg catttggaat    60
gcccacaaag caactagtca tcagacggct cacgtgtgtc tctccgtaca gtgccacgat   120
tgctctaggg agtgaaatgt cgggtgggat agaagatgtt agagcagagg atatcacagc   180
catccacaca gaatctgggg tcaggatcaa aactgctgta gggagaggag ggtttgtgaa   240
ggacatatac gtgaagagaa tgactatgca caccatgaaa tgggtctttt ggatgactgg   300
aaattatggg cacatgctga taagaattat gacccaaacg cactgcnatt gattcaagnc   360
ataaatnaca gggncatggt ngcagacaat gtgacaatgg cgncaagatt ggagggcatc   420
gcaggcgatc cattcaagga aatttgcatc tctaatgtca caatcggatt ggcaccgaag   480
gcgaagaagg taccctggac ctgcaccgaa attgagggga tgacaagcgg ggtaagtcca   540
cggccatgtg atttgctacc ggatcaaggg ccagagaaaa tcacatcctg tgatttccct   600
ccggagaata taccaatcga cttggtgcag ctcaagacgt gctccttcgg aatgagttat   660
atgtgaactt tgcttctcta ctaccatcaa gcaatgtata aacactgcta gctccgagca   720
aaaatatat ataatctact agttttctc agttttataa aaaaaaaaa aaaa            774
```

<210> SEQ ID NO 19
<211> LENGTH: 268
<212> TYPE: DNA
<213> ORGANISM: Populus tremula x tremuloides KR125
<220> FEATURE:
<221> NAME/KEY: misc_feature
<222> LOCATION: (1)...(268)
<223> OTHER INFORMATION: n = A,T,C or G

<400> SEQUENCE: 19

```
tgcctctcac gattacggcg cttgtttcca tgccatggag gagagagcta tggaagatgg    60
gatcccagag ttttttgaaga ggtcgatcat attgcagact tttggtgtca aatttaacca   120
tccatgccaa gacgttgaga atgtcgtgat accaccttac atctcgccgg naagcgtacg   180
gacaacccte gagaaatatc cgtgaccggc ccggcgggac atttgggcct tntttagagg   240
caaaaggaag tgccccccaaa aacattag                                      268
```

<210> SEQ ID NO 20
<211> LENGTH: 672
<212> TYPE: DNA
<213> ORGANISM: Populus tremula x tremuloides KR129B
<220> FEATURE:
<221> NAME/KEY: misc_feature
<222> LOCATION: (1)...(672)
<223> OTHER INFORMATION: n = A,T,C or G

<400> SEQUENCE: 20

```
gtcgacccac gtcgtcacgc ccacgcgtcc gcggacgcgt gggttctact tccatgacat    60
tatttacaac ggcaagaact ccaagaacgc caccgcggca attgtggggg cgccagcttg   120
gggcaacaag accatattgg ctaaccagaa ccatttggt gacttggttg tgttntgatg    180
```

```
acccattac cttagacaac gacctacact cggccccgat aggtcgagcc caagggattt     240
acgtgtatga caagaaagaa atcttcactg cctggctggg tttctctttc gtttttaact     300
ctactgagca taaaggaagc ataaactttg ccagagctga tccattgatg aacaagacta     360
gggatgtttc agtgattggt gggactggag acttcttcat ggctcgagga atagccacat     420
tgatgactga tgcattcgag ggtgaagttt atttcaggct tcgtgttgat attcagttgt     480
acgagtgctg gtgacagttc ttgcttccag ttcagcattt gatgttctct ctttttaatc     540 ggttttcag caaaattaag aggaaggttg atttccttg gagttattga atcaagattc       600
ttgtatcacc aagtgtttca taattgaaat caacttttca tgaggttata accaaaaaaa     660
aaaaaaaaaa aa                                                         672
```

```
<210> SEQ ID NO 21
<211> LENGTH: 509
<212> TYPE: DNA
<213> ORGANISM: Populus tremula x tremuloides KR140
<220> FEATURE:
<221> NAME/KEY: misc_feature
<222> LOCATION: (1)...(509)
<223> OTHER INFORMATION: n = A,T,C or G

<400> SEQUENCE: 21
agtcgtcacg cttgttcgat ccctgcacta atcctgatta atgcctgcat tcccttttag     60
attttgtgtt tgattttgtc ctgtaaggag ctggatatgc gggatcatat ggagagattt    120
gtagttcttc cattctccat cgcctgtgct tctcactcca gtgttgatgt ggcctccagt    180
gaatcctcca agaaaccaag acccgaaacc aaatcacatg catcaagagg acaagaaggg    240
gaggaaagct cttgtaaaga aaagacgaag aacagtacac ttggnttcct gctggctctt    300
ccaaagcctt gcatatccag tagcttgcac aaattgatta gangcatcaa gactctntcc    360
caagtatttg tgnacaagga agaagacgag gagctaatgg aaagagagat ggaaatcggn    420
tatccaactg atgtngaagc atgtaacaca cataggattn ggatggnact acgatgncaa    480
atctataagg ctgggatgct gaactcaga                                       509
```

```
<210> SEQ ID NO 22
<211> LENGTH: 685
<212> TYPE: DNA
<213> ORGANISM: Populus tremula x tremuloides KR152
<220> FEATURE:
<221> NAME/KEY: misc_feature
<222> LOCATION: (1)...(685)
<223> OTHER INFORMATION: n = A,T,C or G

<400> SEQUENCE: 22
acgcttttca gtcgtgagtt aagcagcaca acaagcatga gaggcactct ctgttatgtt     60
gctccanaat atggtgggtg tggatacttg atggagaagg ctgatatata cagcttaggg    120
gttctaatcc tcgtgattgt ctccggtagg aggccattac atgttcttgc ttcaccgatg    180
aagcttnaaa aggcaaattt aataagctgg tgcaggcagt tagctcaaac tgggaacatc    240
ttagaacttg tagatgagag aatgaagnac gaacacaata aggagcaggc aagcttgtgt    300
ataaacttgg ctctgacatg cttgcagagg atgcctgaat tgaggccaga tattggagag    360
atagtgaaga ttctgaaagg ggagatggat ctaccgcatc ttcctttcga attttctccc    420
tccccacctt ccaaattgtt tagtaggtca aggagaaaac aaaaatctaa tgcagagtag    480
gttcagtaca tattctttgt tttcttccat tgatcatgtt tttactgagt ggtacatagg    540
atgggagctg taatctgata acacattatg gatgtgaagg tattttctta attcgagtct    600
```

```
acaatgctat atgtacatca gaatctcaga tgagtggatt ttgctttcct tgtctctaat    660
tggatatgca aaaaaaaaaa aaaaa                                           685

<210> SEQ ID NO 23
<211> LENGTH: 389
<212> TYPE: DNA
<213> ORGANISM: Populus tremula x tremuloides KR163
<220> FEATURE:
<221> NAME/KEY: misc_feature
<222> LOCATION: (1)...(389)
<223> OTHER INFORMATION: n = A,T,C or G

<400> SEQUENCE: 23
tagaagagat gtacgacagt gtgtgtgctg atatttatga gtggcagcca actttgatga     60
attatcagat gcaagcatct ggtaaagnca ataagccact gaggcctaaa gctcatctgt    120
catgtggccc tggacagaaa atcagatcaa tcaagtttgc cagctttggg acaccagaag    180
gggtttgtgg tagctatcgc cagggaagct gtcatgcctt ccactcttat gatgcttnta    240
acaatctttg tgttgggcag aattcatgct cggtgactgt agcacctgaa atgtttgggg    300
gagatccttg cctgaatgtc atgaagaaac tagcagtaga ggccatttgc agcttgatga    360
gctacaaccg gcttgaagta aatgaaata                                      389

<210> SEQ ID NO 24
<211> LENGTH: 142
<212> TYPE: DNA
<213> ORGANISM: Populus tremula x tremuloides KR163

<400> SEQUENCE: 24
ggtttcctgt gatcttatat tttttattca atgtaaactt cctgggaacc ccacttcctt     60
tgttgctatg ttcttgtaag aaagttttta agttaaagaa atgataccaa acttttcaaa    120
aaaaaaaaaa aaaaaaaaaa aa                                             142

<210> SEQ ID NO 25
<211> LENGTH: 654
<212> TYPE: DNA
<213> ORGANISM: Populus tremula x tremuloides KR221
<220> FEATURE:
<221> NAME/KEY: misc_feature
<222> LOCATION: (1)...(654)
<223> OTHER INFORMATION: n = A,T,C or G

<400> SEQUENCE: 25
ctcagccaga tgtgtcctga gcttgcttgg atgacaacaa gcaactggaa ttattgctgc     60
attaactata ttataagaag cagttactca gtggggattc tggtgggcat tgctgtcat    120 ggacactacc agatgagagc ttgctgaacg tcatctaatc aggggtgaga ggggggaaa    180 ctgatttaag cgtgattgtt tcagctcgtg gcagctattt attatctatt gaaatcctat    240
gcgggttttg tctgccacca cggcaaagga agtaaaggat tctatgttcg taatacattg    300
agaagggaga acaaggcagc aggctggcct gggattgaaa gaggacagca aaagaagat    360 gagatctta tagatgactg ataaatgtcg atttcctggc aagcatgaag actctcgtgc    420
caggcttctt attgagaatg gaaagtggag tcttgcttct tgttgtactc tgggttcttg    480
gcgaggacnt tttgatttgc acgtgacaga gtcattaggt tgtttgtcca tgtncatggt    540
gggattaccc acagtgtgtt ntgagttgtn tagagaaaag tgtccccagg gatggagact    600
gtgaccccct ggccagttta ttggctattg tatcctcgct tatttttaa atgt          654
```

<210> SEQ ID NO 26
<211> LENGTH: 171
<212> TYPE: DNA
<213> ORGANISM: Populus tremula x tremuloides KR224
<220> FEATURE:
<221> NAME/KEY: misc_feature
<222> LOCATION: (1)...(171)
<223> OTHER INFORMATION: n = A,T,C or G

<400> SEQUENCE: 26

```
gctagctgta tagttgaaga gaagctgaag angaagagat ggnagagcag naggtgaaga      60
angtagaggc tgtaacgccc gtggntccag ctccagtgga aactaaaagt gatgtggncg     120
atgggaaagt tacggctcca ccacctccag tggntgcaga gaaagagaag g             171
```

<210> SEQ ID NO 27
<211> LENGTH: 580
<212> TYPE: DNA
<213> ORGANISM: Populus tremula x tremuloides KR235

<400> SEQUENCE: 27

```
gtaaagctcc gtattttag  ctgggtttct cttaaaaaat ggaacttggg ctcgtggggt      60
tgtagagagc agcctggatt gcagggacgc tgcctatact tatagcttca ctgccatgtg     120
cttggctggg ttcttttcat ggacttgttt tggggtatgc aaagagagga aagatcatgc     180
aatcatcatc tcatcgtaaa tccactgctc cccaaagatt cttttctcat ttctatgtgg     240
tggctgtggc gtggacaact ctcttgcttc ttggaacatc gatatatgct tatagaatga     300
caccaatagt ctctgagccg tttatctact ctgatctagg cagctactag gcaggacgat     360
ctaacatatt ctcatttcat cgatcacggt agatgagtat agagaataga tacagggttt     420
ggctttctgt gtttctgctt tggctaatgg aagttcaggt ctcgaggcgt atatacgaga     480
ctgcatatgt atttaaatat agcgcatctg ctcggatgca cattttgct  atcttactgg     540
ctatccttct accagcagcg ctctgaccct tgctgtactg                           580
```

<210> SEQ ID NO 28
<211> LENGTH: 511
<212> TYPE: DNA
<213> ORGANISM: Populus tremula x tremuloides KR235

<400> SEQUENCE: 28

```
ggtaatattt tctttggggg gttggattca tcagcatcgt tgcccatgcc attctttgct      60
cactaagggg aacacgtggg gaagggctga tggatatgta attccccgt  gttgattggg     120
ttcgagattg tttcatctcc acactatttg ggcagagaat tgttatatat gctggcatgg     180
tttttgctag tggaggggca gacctcacca tttggttagt ttttggatt  tgtggtgtca     240
aatctggtgt ttgcagctgc agaaacacac agttgccatc gcgtgattaa gatgatggct     300
acagcaaagt cttgacaaga ggtaggaaaa aatttattag agaagcaaat tagtttggtg     360
aatgtttatg ttatgtccag atgccctttc tgaggcgatt gaattctatc tgattgtgta     420
gttcctgtaa gcttcagaca tctcatccaa ttggatggtg caattactat aatgaattgt     480
gcattcaaat tgttgctcga aaaaaaaaaa a                                    511
```

<210> SEQ ID NO 29
<211> LENGTH: 1170
<212> TYPE: DNA
<213> ORGANISM: Populus tremula x tremuloides KR240
<220> FEATURE:
<221> NAME/KEY: misc_feature
<222> LOCATION: (1)..(1170)
<223> OTHER INFORMATION: n = A,T,C or G

<400> SEQUENCE: 29

| | | | | |
|---|---|---|---|---|
| aaacgtgatt | ctacaaatca | aatatagaaa | gctgccatgg | ctatcaacag | tattacttta | 60 |
| gctgatatgg | aaatccctga | atcttacttg | gaggctcttc | caaagaatgg | aaaagcgagc | 120 |
| ctaggagacc | tcatgtatcg | atatatttct | tcagatcaat | tttatccaga | atgtctcctt | 180 |
| gattgcctag | atttgtcttc | tgaacatcaa | gctatagaac | ttgcgaaccg | agtggaggcc | 240 |
| tcaatctata | tatggcgcaa | aagaaccaat | tataaacctg | ccagtagtac | aaatcgatcc | 300 |
| agttcaaagt | cgtcatggga | attggtcaag | gaactgatga | ttgatgcaga | caagagggaa | 360 |
| tngcttgctg | natagagcag | aaagcctcct | actttgcctg | aagcagcgat | nccctggtct | 420 |
| tccacagaca | actttggata | tgagcaaant | ccagtacaac | aggatgtngg | gaaatccatt | 480 |
| tgggagagct | actcgagagt | nttagagagc | ntngncatnt | antatnntgg | nccgaattg | 540 |
| acgncctgct | ctacgtggat | gatttgacaa | aacattcgga | tcatttctct | tcaatctcta | 600 |
| aagtcagtgt | gattgctcac | aaaagtgtaa | caattccata | ctcggtcccc | gtctcaaaca | 660 |
| ctccatacaa | aacagcnttc | aacacaccaa | gcttttcacc | aggtcaacca | cgagtaagcc | 720 |
| ctgcaaaggg | agaccggtcg | cctttcatga | ccagtggcaa | aattcctcag | cgtggtgtag | 780 |
| gtgtaaaaaa | ggtgtngaca | gagtatctca | gtatggatac | agaaggncag | ggatggcggc | 840 |
| aacatgatcg | agggagcaga | caatgtgatt | cgaaacacct | cggcttctca | aaccggagtt | 900 |
| gaatcttttg | ggtctataat | agaaacaatc | agctcaccgg | agaacagatt | ttctgatatc | 960 |
| tgctaaattc | atctgctgat | ggctccttcg | tgcatgtctt | tttttccccg | tagaattagg | 1020 |
| aagatgtttg | agttgggtaa | agcacatcat | gttatttaac | cttagatgta | acgagatata | 1080 |
| tgtaatgata | atgagttgag | tgcttcatga | atcattcatg | tagttcaatc | cttctaatga | 1140 |
| atttgttgtt | tgtcgattaa | aaaaaaaaaa | | | | 1170 |

<210> SEQ ID NO 30
<211> LENGTH: 1026
<212> TYPE: DNA
<213> ORGANISM: Populus tremula x tremuloides KR242
<220> FEATURE:
<221> NAME/KEY: misc_feature
<222> LOCATION: (1)..(1026)
<223> OTHER INFORMATION: n = A,T,C or G

<400> SEQUENCE: 30

| | | | | |
|---|---|---|---|---|
| agtcccattc | tttttcctag | ccccaagttt | nntnttgagg | ggtgataaaa | aatgaaccaa | 60 |
| gagatgaatg | gtgttgacac | tgagattgat | cagaaccacc | aagagaatgt | gcaagagaaa | 120 |
| atcgattatg | tgtttaaggt | ggtggtgatc | ggtgactctg | cagtgggcaa | gacgcaaatt | 180 |
| ctttccaggt | ttaccaagaa | tgaatnctg | ctttgattca | naagtctacc | atcggtgtcg | 240 |
| anttccanga | ctaggactgt | catcattaaa | gacaaggtca | tcaaggctca | gatctgggat | 300 |
| actgctggcc | aagaaaggta | ccgggcagtg | acaagcgcat | actatagagg | ggcactatgg | 360 |
| gccatgttag | tctacgacat | taccaagaga | ccaacgtttg | atcatgtggc | taggtgggtg | 420 |
| gangagctcc | gagcccatgc | tgacagctca | attgtgatca | tgctgatcgg | aaacaaggct | 480 |
| gatcttgtgg | acctcagggc | agttccaaca | gaagacgcgg | tggaatttgc | agaggatcaa | 540 |
| ggcctctttt | tttctgagac | atcagcccct | agtggtgaca | atgtggacgg | tgcattttc | 600 |
| aggctgctag | aagaaattta | cggtgtgatt | tgtaagaagt | cattggaatg | tggcaatgga | 660 |

```
aaaccccatg ctgctgatgc cataacgctt agaggttcta agattgatgg catatcaggg     720
acggatctgg agattagtga gatgaagaaa ttatctgctt gctcgtgttg atttgatcat     780
ttttcttgtg aattgtgtac tataagactt caccactccc atgttcttaa ttgattctgt     840
ggctttcttt ggaaagtggt gatcggtcgt gtggtgaggg tggcaagttt tttctttttct    900 gtgacctgtc aagattttag cagtattgta cttgtcttac agaacccatg aattgtggtt     960
tttttatatg tattgatttg gatggatggt tttcctttc cttcaaaaaa aaaaaaaaaa      1020
aaaaaa                                                                1026

<210> SEQ ID NO 31
<211> LENGTH: 820
<212> TYPE: DNA
<213> ORGANISM: Populus tremula x tremuloides KR292
<220> FEATURE:
<221> NAME/KEY: misc_feature
<222> LOCATION: (1)...(820)
<223> OTHER INFORMATION: n = A,T,C or G

<400> SEQUENCE: 31
atatgaacgc ttctctatgg gttttgtcatg tggagaggat gattttgaaa agaatggaag    60
tcatgaagtt ccgttaatag ttgatagcag agggactaga gtcagcggtg gctatatgga    120
ttnacaacat cttcatcatg cagttganta cgaggtcgaa ttctggccag ttgaacaccc    180
aatggaacca caggatgaag atcgtcctgt caaatgtcca atgccaacct cttctgntat    240
caagaatgga aggncgcatg aggagagatt agagaagaga gcggacgact ccaactacct    300
gcggtaatga acaaacaagg cattgttgtg gtggctgcag agcccaagt ccgagcagtg     360 cgtaaaaggc accatacact tacccgccag gaccaccgtg taatagcacc tgatctaaca    420
aggatggctt cnacntntcc tgctctgcca anctcagaac gtcaccnatt tttcaaatgc    480
ttcaagaact cngacaagtt cgatcagtat taaaaggta taagaataa attaggaaac      540 ccacatttcc gctccatcta gctttaatag ctacttttca atccattgcg gagcggtcaa    600
tgaattcttc atgatttgta tttcgggcca atagggaaag aaatatcata gatatgcggt   660
ataagaagca ctcttattgt actagatttt tattttttat atattctgta gaatgtgtct    720
tccagcctaa ttgtaggttt cctttatcat ttctttgttc agatttggat ggataattag    780
catgacactc tgcaatacca aaaaaaaaaa aaaaaaaaa                            820

<210> SEQ ID NO 32
<211> LENGTH: 303
<212> TYPE: DNA
<213> ORGANISM: Populus tremula x tremuloides KR313
<220> FEATURE:
<221> NAME/KEY: misc_feature
<222> LOCATION: (1)...(303)
<223> OTHER INFORMATION: n = A,T,C or G

<400> SEQUENCE: 32
gaaaaattct cctggaccag ctaagagaga gcttagacaa gctactagac aggcacttca    60
attgcttcaa gacaactatc cagaatttgt ggccaaacag atcttcatca atgttccctg    120
gtggtaccta acagtaaata gaatgataag tccatttta acccagagga ccagaagtaa    180
gtttgtcttt gttggnccctt ccaaatctgc cgaaacccctt atcaggtaca tagccgctga   240
gcaaatacca gtgaagtacg gaggcctaag caaagatggt gaatttggct cagctgangc    300
tgt                                                                   303
```

```
<210> SEQ ID NO 33
<211> LENGTH: 616
<212> TYPE: DNA
<213> ORGANISM: Populus tremula x tremuloides KR313
<220> FEATURE:
<221> NAME/KEY: misc_feature
<222> LOCATION: (1)...(616)
<223> OTHER INFORMATION: n = A,T,C or G

<400> SEQUENCE: 33
gttgcgggga tgggatgtaa gctatggtgc agaatttgta ccaagggctg aagatagcta      60
cacagtgatc atccaaaagg ctagaaaggt tgntgcaact gaacaaccag tggtttgcaa     120
cagtttcaaa attggtgaac ctggtaaagt tgttctcacc attgacaata ccacatccaa     180
gaagaagaag aagctcctct atcgcttgaa aaccaagccc gcttcttctg attaattaag     240
ggactatata tagtgaaaca ataatagaag attttgctta cattcttgct gctgctgctg     300
ctgccaattt tatcaacatg atcatatcac agcttgaagg tgttctgagg gtctcgatca     360
tggagaagat aaagaaatct tgaagatgtt tatttatatg tttatttata attgaattt      420 gttttggtgt ggaatggatt aaggatgttg tgcaattgaa ggctagaagc atgtgtgggg     480
atagggaaga agctccatta ctagtgccaa gagttttctt tgtaaattcg ttatggcttt     540
ctttctcttt ccctgtaagt atcttttgga catattatga tattaatgaa gacagtatct     600
ttcataaaaa aaaaaa                                                    616

<210> SEQ ID NO 34
<211> LENGTH: 340
<212> TYPE: DNA
<213> ORGANISM: Populus tremula x tremuloides KR318
<220> FEATURE:
<221> NAME/KEY: misc_feature
<222> LOCATION: (1)...(340)
<223> OTHER INFORMATION: n = A,T,C or G

<400> SEQUENCE: 34
acacaggttc agtccatgca atccacacag aacatcaact gctccagcat catccgtcna      60
cgatatcctc cgtcgagaca aacttcgagt ggactcaatt attcaggccc ggcgttcagt     120
gaacttgacc agcagtggtg agcacatgaa gagtagtgtc ccgttctatg gtctatccaa     180
aatcactgca agtgactata ttgtaaacgt tggaatcggt acgcccaaga aggaaatgcc     240
acttatattc gacacaggca gtggtctcat ttggactcaa tgcaagccat gcaaggcttg     300
ctatccaaaa gtccntgtgt tcgatccaac caagtcagct                          340

<210> SEQ ID NO 35
<211> LENGTH: 489
<212> TYPE: DNA
<213> ORGANISM: Populus tremula x tremuloides KR318

<400> SEQUENCE: 35
tgcatcagct tttaagattg atagcgccat cgactccggt gcagtgctca ctcggctgcc      60
tccgaaggca tactcgacac tgaggtcggt gttccgagaa atgttgaaag gttatccttt     120
gtcggcccaa gatctagaca catgctatga cttcagtaat tatagcacgg ttgcaatacc     180
ttcgattagt gtgttcttcg aaggtggcgt cgagatggat atcgatgttt cggggatcat     240
gttgcaatat ccagaagaga gcaaggtgta ctgcttggca tttgcagaat tggattacga     300
attttctatc tttgggaatt ttcagcaaaa gacttacact atagtctttg atggtgcgaa     360
ggaaaggatt gggtttgccc ccggtggctg tgactaaaat ggggaaaata aaataaaatt     420
```

```
ggagcactag ctctaaatta taatatatca ataaaagtgg tttgatttta taaaaaaaaa    480
aaaaaaaaa                                                           489
```

<210> SEQ ID NO 36
<211> LENGTH: 453
<212> TYPE: DNA
<213> ORGANISM: Populus tremula x tremuloides KR459

<400> SEQUENCE: 36

```
caaccgtatc agatgcacct cccatccatt acatggttaa aatagagtca ttttcgtcac    60
ttgggaaaaa tgcagtggag acatatgaat cagggttttt tgaagctgga ggctatagat   120
ggaaattagt tctctatccg aacggaaaca agagcaataa tgtaaaagat tccatctctc   180
tctatttagc aatggttgac gcaagttctc ttccacgtgg ttgggaggtc aacgtgattt   240
ttcggttgtt tttgcttgac caaaacaagg acagctactt ggtaattcaa gcaggaaagg   300
aaagacgctt tcacggattg aatcttcaaa gtggttttga tcaattcatt aagctttcaa   360
catttaatga tgctcgttat ggattccttc tggaagacac ttgtgtgctt ggagctgaag   420
tatttgtctg tggagaaaga agcagaggca aag                                453
```

<210> SEQ ID NO 37
<211> LENGTH: 586
<212> TYPE: DNA
<213> ORGANISM: Populus tremula x tremuloides KR463

<400> SEQUENCE: 37

```
cgaagttaga acacattatc actagtttag gccacagagt tgcagagatg ccagttcctg    60
tcgaacaagc acgagtaaag ccttcagatg atcatttctg gcttgagaaa cctgccattg   120
ttcttgactt gattcagttc attctgtttc agaattcatt tgagattgct tcttcttct   180 ggatttggag cacatacgga ttccgctcat gcatcatgga aaaagtgggc tacattgtgc   240
caaggcttat tatgggttta gctgttcaag ttctatgcag ttacagcacc ttgccttgtgt   300 acgctctagt ctcacagatg gcaccaggt tcaggaaagg gatgtttggt gaggatacgg    360
aagcggcact agaaaactgg gcaggcagag taaagggcaa gagggacaca agcgagaacc   420
acggagcaca tatggataga ctagccacag aatcatctca tagtgcggca aagaaatgg    480 ttattattgg aggcacagag ctttcttccg tgacccaagc gcctgtatct tgaaatttgg   540
ttcttcggca aaaaggcaaa agggaacatc cacttacatc tcctca                  586
```

<210> SEQ ID NO 38
<211> LENGTH: 529
<212> TYPE: DNA
<213> ORGANISM: Populus tremula x tremuloides KR465

<400> SEQUENCE: 38

```
ctacacactg aaggttgatg aaaagagtga cgtgtacagc tttggtgtag ttctcttgga    60
actcgttact ggtagaaaac cggttggaga attcggtgat ggtgtggata tagttcaatg   120
ggttcgaaaa atgacagact caatcaagga aggagttttg aaagtcctgg acccaagact   180
cccatcagtt ccgcttcatg aggtgatgca tgtgttctat gttgcaatgc tttgtgtgga   240
agaacgggct gtcgaacgcc aacaatgcg agaagttgtt cagattctaa cagagcttcc   300
caagtcacca agctcaaaac aaggagactc agtaatcaca gagccctcgc acattcagc   360 cgccaccgca gcgctcgact ctcccagttc aacagctaaa gacgtcccaa agaccatca   420 gcagccacca cctgctgatc ttcttagcat ttgaagccat tctgaatgga gggttgctgt   480
```
ttgttctcta aaattccagg aattgtgtta gtttctgtcc gtctttgtg    529

<210> SEQ ID NO 39
<211> LENGTH: 42
<212> TYPE: DNA
<213> ORGANISM: Artificial Sequence
<220> FEATURE:
<223> OTHER INFORMATION: PCR Primer - attB1-T12VN
<221> NAME/KEY: misc_feature
<222> LOCATION: (1)...(42)
<223> OTHER INFORMATION: n = A,T,C or G

<400> SEQUENCE: 39
gggacaagtt tgtacaaaaa agcaggcttt tttttttttt vn    42

<210> SEQ ID NO 40
<211> LENGTH: 33
<212> TYPE: DNA
<213> ORGANISM: Artificial Sequence
<220> FEATURE:
<223> OTHER INFORMATION: PCR Primer - KR459FwAttB2

<400> SEQUENCE: 40
agaaagctgg gtcaaccgta tcagatgcac ctc    33

<210> SEQ ID NO 41
<211> LENGTH: 34
<212> TYPE: DNA
<213> ORGANISM: Artificial Sequence
<220> FEATURE:
<223> OTHER INFORMATION: PCR Primer - KR463FwAttB2

<400> SEQUENCE: 41
agaaagctgg gtcgaagtta gaacacatta tcac    34

<210> SEQ ID NO 42
<211> LENGTH: 32
<212> TYPE: DNA
<213> ORGANISM: Artificial Sequence
<220> FEATURE:
<223> OTHER INFORMATION: PCR Primer - KR465FwAttB2

<400> SEQUENCE: 42
agaaagctgg gtctacacac tgaaggttga tg    32

<210> SEQ ID NO 43
<211> LENGTH: 54
<212> TYPE: DNA
<213> ORGANISM: Artificial Sequence
<220> FEATURE:
<223> OTHER INFORMATION: PCR Primer - attB2-T7

<400> SEQUENCE: 43
ggggaccact ttgtacaaga aagctgggtg taatacgact cactataggg cgaa    54

<210> SEQ ID NO 44
<211> LENGTH: 34
<212> TYPE: DNA
<213> ORGANISM: Artificial Sequence
<220> FEATURE:
<223> OTHER INFORMATION: PCR Primer - KR459ReAttB1

<400> SEQUENCE: 44
aaaaagcagg ctctttgcct ctgcttcttt ctcc    34

```
<210> SEQ ID NO 45
<211> LENGTH: 32
<212> TYPE: DNA
<213> ORGANISM: Artificial Sequence
<220> FEATURE:
<223> OTHER INFORMATION: PCR Primer - KR463ReAttB1

<400> SEQUENCE: 45
aaaaagcagg cttgaggaga tgtaagtgga tg                                  32

<210> SEQ ID NO 46
<211> LENGTH: 31
<212> TYPE: DNA
<213> ORGANISM: Artificial Sequence
<220> FEATURE:
<223> OTHER INFORMATION: PCR Primer - KR465ReAttB1

<400> SEQUENCE: 46
aaaaagcagg ctcacaaaga cggacagaaa c                                   31

<210> SEQ ID NO 47
<211> LENGTH: 13599
<212> TYPE: DNA
<213> ORGANISM: Artificial Sequence
<220> FEATURE:
<223> OTHER INFORMATION: Vector pK7GWIWG2(I)

<400> SEQUENCE: 47
ctagagggcc cgacgtcgca tgcctgcagg tcactggatt ttggttttag gaattagaaa    60
ttttattgat agaagtattt tacaaataca aatacatact aagggtttct tatatgctca   120
acacatgagc gaaaccctat aagaacccta attcccttat ctgggaacta ctcacacatt   180
attctggaga aaaatagaga gagatagatt tgtagagaga gactggtgat ttttgcggac   240
tctagcatgg ccgcgggata tcacaagttt gtacaaaaaa gctgaacgag aaacgtaaaa   300
tgatataaat atcaatatat taaattagat tttgcataaa aaacagacta cataatactg   360
taaaacacaa catatccagt cactatggcg gccgcattag gcaccccagg ctttacactt   420
tatgcttccg gctcgtataa tgtgtggatt ttgagttagg atccggcgag attttcagga   480
gctaaggaag ctaaaatgga gaaaaaaatc actggatata ccaccgttga tatatcccaa   540
tggcatcgta agaacatttt gaggcatttt cagtcagttg ctcaatgtac ctataaccag   600
accgttcagc tggatattac ggcctttttta aagaccgtaa agaaaaataa gcacaagttt   660
tatccggcct ttattcacat tcttgcccgc ctgatgaatg ctcatccgga attccgtatg   720
gcaatgaaag acggtgagct ggtgatatgg gatagtgttc acccttgtta caccgttttc   780
catgagcaaa ctgaaacgtt ttcatcgctc tggagtgaat accacgacga tttccggcag   840
tttctacaca tatattcgca agatgtggcg tgttacggtg aaaacctggc ctatttccct   900
aaagggttta ttgagaatat gttttttcgtc tcagccaatc cctgggtgag tttcaccagt   960
tttgatttaa acgtggccaa tatggacaac ttcttcgccc ccgttttcac catgggcaaa  1020
tattatacgc aaggcgacaa ggtgctgatg ccgctggcga ttcaggttca tcatgccgtc  1080
tgtgatggct tccatgtcgg cagaatgctt aatgaattac aacagtactg cgatgagtgg  1140
cagggcgggg cgtaaacgcg tggatccggc ttactaaaag ccagataaca gtatgcgtat  1200
ttgcgcgctg attttgtcgg tataagaata tatactgata tgtatacccg aagtatgtca  1260
aaaagaggtg tgctatgaag cagcgtatta cagtgacagt tgacagcgac agctatcagt  1320
tgctcaaggc atatatgatg tcaatatctc cggtctggta agcacaacca tgcagaatga  1380
```

-continued

```
agcccgtcgt ctgcgtgccg aacgctggaa agcggaaaat caggaaggga tggctgaggt   1440
cgcccggttt attgaaatga acggctcttt tgctgacgag aacagggact ggtgaaatgc   1500
agtttaaggt ttacacctat aaaagagaga gccgttatcg tctgtttgtg gatgtacaga   1560
gtgatattat tgacacgccc gggcgacgga tggtgatccc cctggccagt gcacgtctgc   1620
tgtcagataa agtctcccgt gaactttacc cggtggtgca tatcggggat gaaagctggc   1680
gcatgatgac caccgatatg gccagtgtgc cggtctccgt tatcggggaa gaagtggctg   1740
atctcagcca ccgcgaaaat gacatcaaaa acgccattaa cctgatgttc tggggaatat   1800
aaatgtcagg ctcccttata cacagccagt ctgcaggtcg accatagtga ctggatatgt   1860
tgtgttttac agtattatgt agtctgtttt ttatgcaaaa tctaatttaa tatattgata   1920
tttatatcat tttacgtttc tcgttcagct ttcttgtaca aagtggtgat atcactagtg   1980
cggccgcctg caggtcgacc atatggtcga cctgcaggcg gccgcactag tgatgctgtt   2040
atgttcagtg tcaagctgac ctgcaaacac gttaaatgct aagaagttag aatatatgag   2100
acacgttaac tggtatatga ataagctgta ataaccgag tataaactca ttaactaata   2160
tcacctctag agtataatat aatcaaattc gacaatttga cttccaagag taggctaatg   2220
taaaatcttt atatatttct acaatgttca agaaacagt tgcatctaaa cccctatggc   2280
catcaaattc aatgaacgct aagcttaata tgactctcaa taaagtctca taccaacaag   2340 tgccaccttta ttcaaccatc aagaaaaag ccaaaattta tgctactcta aggaaaactt   2400
cactaaagaa gacgatttag agtgttttac caagaattc tgtcatctta ctaaacaact   2460
aaagatcggt gtgatacaaa acctaatctc attaaagttt atgctaaaat aagcataatt   2520
ttacccacta agcgtgacca gataaacata actcagcaca ccagagcata tatattggtg   2580
gctcaaatca tagaaactta cagtgaagac acagaaagcc gtaagaagag caagagtat   2640 gaaaccttac ctcatcattt ccatgaggtt gcttctgatc ccgcgggata tcaccacttt   2700
gtacaagaaa gctgaacgag aaacgtaaaa tgatataaat atcaatatat taaattagat   2760
tttgcataaa aaacagacta cataatactg taaaacacaa catatccagt cactatggtc   2820
gacctgcaga ctggctgtgt ataagggagc ctgacatta tattccccag aacatcaggt   2880
taatggcgtt tttgatgtca ttttcgcggt ggctgagatc agccacttct tccccgataa   2940
cggagaccgg cacactggcc atatcggtgg tcatcatgcg ccagcttca tccccgatat   3000 gcaccaccgg gtaaagttca cgggagactt tatctgacag cagacgtgca ctggccaggg   3060
ggatcaccat ccgtcgcccg ggcgtgtcaa taatatcact ctgtacatcc acaaacagac   3120
gataacggct ctctctttta taggtgtaaa ccttaaactg catttcacca gtccctgttc   3180
tcgtcagcaa aagagccgtt catttcaata aaccgggcga cctcagccat cccttcctga   3240
ttttccgctt tccagcgttc ggcacgcaga cgacgggctt cattctgcat ggttgtgctt   3300
accagaccgg agatattgac atcatatatg ccttgagcaa ctgatagctg tcgctgtcaa   3360
ctgtcactgt aatacgctgc ttcatagcac acctcttttt gacatacttc gggtatacat   3420
atcagtatat attcttatac cgcaaaaatc agcgcgcaaa tacgcatact gttatctggc   3480
ttttagtaag ccggatccac gcgtttacgc cccgccctgc cactcatcgc agtactgttg   3540
taattcatta agcattctgc cgacatggaa gccatcacag acggcatgat gaacctgaat   3600
cgccagcggc atcagcacct tgtcgccttg cgtataatat ttgcccatgg tgaaaacggg   3660
ggcgaagaag ttgtccatat tggccacgtt taaatcaaaa ctggtgaaac tcacccaggg   3720
attggctgag acgaaaaaca tattctcaat aaaccctttta gggaaatagg ccaggttttc   3780
```

```
accgtaacac gccacatctt gcgaatatat gtgtagaaac tgccggaaat cgtcgtggta    3840
ttcactccag agcgatgaaa acgtttcagt ttgctcatgg aaaacggtgt aacaagggtg    3900
aacactatcc catatcacca gctcaccgtc tttcattgcc atacggaatt ccggatgagc    3960
attcatcagg cgggcaagaa tgtgaataaa ggccggataa aacttgtgct tatttttctt    4020
tacggtcttt aaaaaggccg taatatccag ctgaacggtc tggttatagg tacattgagc    4080
aactgactga aatgcctcaa aatgttcttt acgatgccat gggatatat caacggtggt    4140 atatccagtg attttttct ccatttagc ttccttagct cctgaaaatc tcgccggatc    4200
ctaactcaaa atccacacat tatacgagcc ggaagcataa agtgtaaagc ctggggtgcc    4260
taatgcggcc gccatagtga ctggatatgt tgtgttttac agtattatgt agtctgtttt    4320
ttatgcaaaa tctaatttaa tatattgata tttatatcat tttacgtttc tcgttcagct    4380
tttttgtaca aacttgtgat atcactagtg cggccgcctg caggtcgact agaatagtaa    4440
attgtaatgt tgtttgttgt tgttttgtt gtggtaattg ttgtaaaaat acggatcgtc    4500
ctgcagtcct ctccaaatga aatgaacttc cttatataga ggaagggtct tgcgaaggat    4560
agtgggattg tgcgtcatcc cttacgtcag tggagatatc acatcaatcc acttgctttg    4620
aagacgtggt tggaacgtct tcttttccca cgatgctcct cgtgggtggg ggtccatctt    4680
tgggaccact gtcggcagag gcatcttgaa cgatagcctt tcctttatcg caatgatggc    4740
atttgtaggt gccaccttcc ttttctactg tccttttgat gaagtgacag atagctgggc    4800
aatggaatcc gaggaggttt cccgatatta cccttttgttg aaaagtctca atagccctt    4860 ggtcttctga gactgtatct ttgatattct tggagtagac gagagtgtcg tgctccacca    4920
tgttgacgaa gattttcttc ttgtcattga gtcgtaaaag actctgtatg aactgttcgc    4980
cagtcttcac ggcgagttct gttagatcct cgatctgaat ttttgactcc atggcctttg    5040
attcagtagg aactactttc ttagagactc caatctctat tacttgcctt ggtttatgaa    5100
gcaagccttg aatcgtccat actggaatag tacttctgat cttgagaaat atatctttct    5160
ctgtgttctt gatgcagtta gtcctgaatc ttttgactgc atctttaacc ttcttgggaa    5220
ggtatttgat ctcctggaga ttattactcg ggtagatcgt cttgatgaga cctgccgcgt    5280
aggcctctct aaccatcgt gggtcagcat tctttctgaa attgaagagg ctaatcttct    5340
cattatcggt ggtgaacatg gtatcgtcac cttctccgtc gaactttctt cctagatcgt    5400
agagatagag aaagtcgtcc atggtgatct ccggggcaaa ggagatcagc ttggctctag    5460
tcgaccatat gggagagctc aagcttagct tgagcttgga tcagattgtc gtttcccgcc    5520
ttcagtttaa actatcagtg tttgacagga tatattggcg ggtaaaccta agagaaaaga    5580
gcgtttatta gaataacgga tatttaaaag ggcgtgaaaa ggtttatccg ttcgtccatt    5640
tgtatgtgca tgccaaccac agggttcccc tcgggatcaa agtactttga tccaaccct    5700 ccgctgctat agtgcagtcg gcttctgacg ttcagtgcag ccgtcttctg aaaacgacat    5760
gtcgcacaag tcctaagtta cgcgacaggc tgccgccctg ccctttttcct ggcgttttct    5820 tgtcgcgtgt tttagtcgca taaagtagaa tacttgcgac tagaaccgga gacattacgc    5880
catgaacaag agcgccgccg ctggcctgct ggctatgcc cgcgtcagca ccgacgacca    5940
ggacttgacc aaccaacggg ccgaactgca cgcggccggc tgcaccaagc tgttttccga    6000
gaagatcacc ggcaccaggc gcgaccgccc ggagctggcc aggatgcttg accacctacg    6060
ccctggcgac gttgtgacag tgaccaggct agaccgcctg gcccgcagca cccgcgacct    6120
```

```
actggacatt gccgagcgca tccaggaggc cggcgcgggc ctgcgtagcc tggcagagcc   6180
gtgggccgac accaccacgc cggccggccg catggtgttg accgtgttcg ccggcattgc   6240
cgagttcgag cgttccctaa tcatcgaccg cacccggagc gggcgcgagg ccgccaaggc   6300
ccgaggcgtg aagtttggcc cccgccctac cctcaccccg gcacagatcg cgcacgcccg   6360
cgagctgatc gaccaggaag gccgcaccgt gaaagaggcg gctgcactgc ttggcgtgca   6420
tcgctcgacc ctgtaccgcg cacttgagcg cagcgaggaa gtgacgccca ccgaggccag   6480
gcggcgcggt gccttccgtg aggacgcatt gaccgaggcc gacgccctgg cggccgccga   6540
gaatgaacgc caagaggaac aagcatgaaa ccgcaccagg acggcagga cgaaccgttt   6600 ttcattaccg aagagatcga ggcggagatg atcgcggccg ggtacgtgtt cgagccgccc   6660
gcgcacgtct caaccgtgcg gctgcatgaa atcctggccg gtttgtctga tgccaagctg   6720
gcggcctggc cggccagctt ggccgctgaa gaaaccgagc ccgccgtct aaaaggtga   6780 tgtgtatttg agtaaaacag cttgcgtcat gcggtcgctg cgtatatgat gcgatgagta   6840
aataaacaaa tacgcaaggg gaacgcatga aggttatcgc tgtacttaac cagaaaggcg   6900
ggtcaggcaa gacgaccatc gcaacccatc tagcccgcgc cctgcaactc gccggggccg   6960
atgttctgtt agtcgattcc gatccccagg gcagtgcccg cgattgggcg gccgtgcggg   7020
aagatcaacc gctaaccgtt gtcggcatcg accgcccgac gattgaccgc gacgtgaagg   7080
ccatcggccg gcgcgacttc gtagtgatcg acggagcgcc ccaggcggcg gacttggctg   7140
tgtccgcgat caaggcagcc gacttcgtgc tgattccggt gcagccaagc ccttacgaca   7200
tatgggccac cgccgacctg gtggagctgg ttaagcagcg cattgaggtc acggatggaa   7260
ggctacaagc ggcctttgtc gtgtcgcggg cgatcaaagg cacgcgcatc ggcggtgagg   7320
ttgccgaggc gctggccggg tacgagctgc ccattcttga gtcccgtatc acgcagcgcg   7380
tgagctaccc aggcactgcc gccgccggca caaccgttct tgaatcagaa cccgagggcg   7440
acgctgcccg cgaggtccag gcgctggccg ctgaaattaa atcaaaactc atttgagtta   7500
atgaggtaaa gagaaaatga gcaaaagcac aaacacgcta agtgccggcc gtccgagcgc   7560
acgcagcagc aaggctgcaa cgttggccag cctggcagac acgccagcca tgaagcgggt   7620
caactttcag ttgccggcgg aggatcacac caagctgaag atgtacgcgg tacgccaagg   7680
caagaccatt accgagctgc tatctgaata catcgcgcag ctaccagagt aaatgagcaa   7740
atgaataaat gagtagatga ttttagcgg ctaaaggagg cggcatggaa aatcaagaac   7800
aaccaggcac cgacgccgtg gaatgcccca tgtgtggagg aacgggcggt tggccaggcg   7860
taagcggctg ggttgtctgc cggccctgca atggcactgg aaccccccaag cccgaggaat   7920 cggcgtgacg gtcgcaaacc atccggcccg gtacaaatcg cgcggcgct gggtgatgac   7980 ctggtggaga agttgaaggc cgcgcaggcc gcccagcggc aacgcatcga ggcagaagca   8040
cgccccggtg aatcgtggca agcggccgct gatcgaatcc gcaaagaatc ccggcaaccg   8100
ccggcagccg gtgcgccgtc gattaggaag ccgcccaagg gcgacgagca accagatttt   8160
ttcgttccga tgctctatga cgtgggcacc cgcgatagtc gcagcatcat ggacgtggcc   8220
gttttccgtc tgtcgaagcg tgaccgacga gctggcgagg tgatccgcta cgagcttcca   8280
gacgggcacg tagaggtttc cgcagggccg ccggcatgg ccagtgtgtg ggattacgac   8340
ctggtactga tggcggtttc ccatctaacc gaatccatga accgataccg gaagggaag   8400 ggagacaagc ccgccgcgt gttccgtcca cacgttgcgg acgtactcaa gttctgccgg   8460
cgagccgatg gcggaaagca gaaagacgac ctggtagaaa cctgcattcg gttaaacacc   8520
```

```
acgcacgttg ccatgcagcg tacgaagaag gccaagaacg gccgcctggt gacggtatcc    8580
gagggtgaag ccttgattag ccgctacaag atcgtaaaga gcgaaaccgg gcggccggag    8640
tacatcgaga tcgagctagc tgattggatg taccgcgaga tcacagaagg caagaacccg    8700
gacgtgctga cggttcaccc cgattacttt ttgatcgatc ccggcatcgg ccgttttctc    8760
taccgcctgg cacgccgcgc cgcaggcaag gcagaagcca gatggttgtt caagacgatc    8820
tacgaacgca gtggcagcgc cggagagttc aagaagttct gtttcaccgt gcgcaagctg    8880
atcgggtcaa atgacctgcc ggagtacgat ttgaaggagg aggcggggca ggctggcccg    8940
atcctagtca tgcgctaccg caacctgatc gagggcgaag catccgccgg ttcctaatgt    9000
acggagcaga tgctagggca aattgcccta gcagggaaa aaggtcgaaa aggtctcttt    9060
cctgtggata gcacgtacat tgggaaccca agccgtaca ttgggaaccg gaacccgtac    9120
attgggaacc caaagccgta cattgggaac cggtcacaca tgtaagtgac tgatataaaa    9180
gagaaaaaag gcgattttc cgcctaaaac tctttaaaac ttattaaaac tcttaaaacc    9240
cgcctggcct gtgcataact gtctggccag cgcacagccg aagagctgca aaaagcgcct    9300
acccttcggt cgctgcgctc cctacgcccc gccgcttcgc gtcggcctat cgcggccgct    9360
ggccgctcaa aaatggctgg cctacggcca ggcaatctac cagggcgcgg acaagccgcg    9420
ccgtcgccac tcgaccgccg gcgcccacat caaggcaccc tgcctcgcgc gtttcggtga    9480
tgacggtgaa aacctctgac acatgcagct cccggagacg gtcacagctt gtctgtaagc    9540
ggatgccggg agcagacaag cccgtcaggg gcgtcagcg ggtgttggcg ggtgtcgggg    9600
cgcagccatg acccagtcac gtagcgatag cggagtgtat actggcttaa ctatgcggca    9660
tcagagcaga ttgtactgag agtgcaccat atgcggtgtg aaataccgca cagatgcgta    9720
aggagaaaat accgcatcag gcgctcttcc gcttcctcgc tcactgactc gctgcgctcg    9780
gtcgttcggc tgcggcgagc ggtatcagct cactcaaagg cggtaatacg gttatccaca    9840
gaatcagggg ataacgcagg aaagaacatg tgagcaaaag gccagcaaaa ggccaggaac    9900
cgtaaaaagg ccgcgttgct ggcgtttttc cataggctcc gccccctga cgagcatcac    9960 aaaaatcgac gctcaagtca gaggtggcga acccgacag gactataaag ataccaggcg    10020
tttccccctg gaagctccct cgtgcgctct cctgttccga ccctgccgct taccggatac    10080
ctgtccgcct ttctcccttc gggaagcgtg gcgctttctc atagctcacg ctgtaggtat    10140
ctcagttcgg tgtaggtcgt tcgctccaag ctgggctgtg tgcacgaacc ccccgttcag    10200
cccgaccgct gcgccttatc cggtaactat cgtcttgagt ccaacccggt aagacacgac    10260
ttatcgccac tggcagcagc cactggtaac aggattagca gagcgaggta tgtaggcggt    10320
gctacagagt tcttgaagtg gtggcctaac tacggctaca ctagaaggac agtatttggt    10380
atctgcgctc tgctgaagcc agttaccttc ggaaaaagag ttggtagctc ttgatccggc    10440
aaacaaacca ccgctggtag cggtggtttt tttgtttgca agcagcagat tacgcgcaga    10500
aaaaaaggat ctcaagaaga tcctttgatc ttttctacgg ggtctgacgc tcagtggaac    10560
gaaaactcac gttaagggat tttggtcatg catgatatat ctcccaattt gtgtagggct    10620
tattatgcac gcttaaaaat aataaaagca gacttgacct gatagtttgg ctgtgagcaa    10680
ttatgtgctt agtgcatcta atcgcttgag ttaacgccgg cgaagcggcg tcggcttgaa    10740
cgaatttcta gctagacatt attttgccgac taccttggtg atctcgcctt tcacgtagtg    10800
gacaaattct tccaactgat ctgcgcgcga ggccaagcga tcttcttctt gtccaagata    10860
```

```
agcctgtcta gcttcaagta tgacgggctg atactgggcc ggcaggcgct ccattgccca   10920
gtcggcagcg acatccttcg gcgcgatttt gccggttact gcgctgtacc aaatgcggga   10980
caacgtaagc actacatttc gctcatcgcc agcccagtcg ggcggcgagt tccatagcgt   11040
taaggtttca tttagcgcct caaatagatc ctgttcagga accggatcaa agagttcctc   11100
cgccgctgga cctaccaagg caacgctatg ttctcttgct tttgtcagca agatagccag   11160
atcaatgtcg atcgtggctg gctcgaagat acctgcaaga atgtcattgc gctgccattc   11220
tccaaattgc agttcgcgct tagctggata acgccacgga atgatgtcgt cgtgcacaac   11280
aatggtgact tctacagcgc ggagaatctc gctctctcca ggggaagccg aagtttccaa   11340
aaggtcgttg atcaaagctc gccgcgttgt ttcatcaagc cttacggtca ccgtaaccag   11400
caaatcaata tcactgtgtg gcttcaggcc gccatccact gcggagccgt acaaatgtac   11460
ggccagcaac gtcggttcga gatggcgctc gatgacgcca actacctctg atagttgagt   11520
cgatacttcg gcgatcaccg cttcccccat gatgtttaac tttgttttag ggcgactgcc   11580
ctgctgcgta acatcgttgc tgctccataa catcaaacat cgacccacgg cgtaacgcgc   11640
ttgctgcttg gatgcccgag gcatagactg taccccaaaa aaacatgtca taacaagaag   11700
ccatgaaaac cgccactgcg ccgttaccac cgctgcgttc ggtcaaggtt ctggaccagt   11760
tgcgtgacgg cagttacgct acttgcatta cagcttacga accgaacgag gcttatgtcc   11820
actgggttcg tgcccgaatt gatcacaggc agcaacgctc tgtcatcgtt acaatcaaca   11880
tgctacccct cgcgagatca tccgtgtttc aaacccggca gcttagttgc cgttcttccg   11940
aatagcatcg gtaacatgag caaagtctgc cgccttacaa cggctctccc gctgacgccg   12000
tcccggactg atgggctgcc tgtatcgagt ggtgattttg tgccgagctg ccggtcgggg   12060
agctgttggc tggctggtgg caggatatat tgtggtgtaa acaaattgac gcttagacaa   12120
cttaataaca cattgcggac gttttaatg tactgaatta acgccgaatt gaattatcag   12180
cttgcatgcc ggtcgatcta gtaacataga tgacaccgcg cgcgataatt tatcctagtt   12240
tgcgcgctat attttgtttt ctatcgcgta ttaaatgtat aattgcggga ctctaatcat   12300
aaaaacccat ctcataaata acgtcatgca ttacatgtta attattacat gcttaacgta   12360
attcaacaga aattatatga taatcatcgc aagaccggca acaggattca atcttaagaa   12420
actttattgc caaatgtttg aacgatctgc ttgactctag ctagagtccg aaccccagag   12480
tcccgctcag aagaactcgt caagaaggcg atagaaggcg atgcgctgcg aatcgggagc   12540
ggcgataccg taaagcacga ggaagcggtc agcccattcg ccgccaagct cttcagcaat   12600
atcacgggta gccaacgcta tgtcctgata gcggtccgcc acacccagcc ggccacagtc   12660
gatgaatcca gaaaagcggc cattttccac catgatattc ggcaagcagg catcgccgtg   12720
ggtcacgacg agatcctcgc cgtcgggcat ccgcgccttg agcctggcga acagttcggc   12780
tggcgcgagc ccctgatgct cttcgtccag atcatcctga tcgacaagac cggcttccat   12840
ccgagtacgt gctcgctcga tgcgatgttt cgcttggtgg tcgaatgggc aggtagccgg   12900
atcaagcgta tgcagccgcc gcattgcatc agccatgatg gatactttct cggcaggagc   12960
aaggtgagat gacaggagat cctgccccgg cacttcgccc aatagcagcc agtcccttcc   13020
cgcttcagtg acaacgtcga gcacagctgc gcaaggaacg cccgtcgtgg ccagccacga   13080
tagccgcgct gcctcgtctt ggagttcatt cagggcaccg gacaggtcgg tcttgacaaa   13140
aagaaccggg cgcccctgcg ctgacagccg gaacacggcg gcatcagagc agccgattgt   13200
ctgttgtgcc cagtcatagc cgaatagcct ctccacccaa gcggccggag aacctgcgtg   13260
```

```
caatccatct tgttcaatca tgcctcgatc gagttgagag tgaatatgag actctaattg    13320
gataccgagg ggaatttatg gaacgtcagt ggagcatttt tgacaagaaa tatttgctag    13380
ctgatagtga ccttaggcga cttttgaacg cgcaataatg gtttctgacg tatgtgctta    13440
gctcattaaa ctccagaaac ccgcggctga gtggctcctt caacgttgcg gttctgtcag    13500
ttccaaacgt aaaacggctt gtcccgcgtc atcggcgggg gtcataacgt gactccctta    13560
attctcatgt atgataattc gagggtaccc ggggatcct                          13599
```

<210> SEQ ID NO 48
<211> LENGTH: 799
<212> TYPE: DNA
<213> ORGANISM: Populus tremula x tremuloides KR121

<400> SEQUENCE: 48

```
ctaaaattga agattgttac ataatttctg gagacgattg tgtggcagtt aaaagcggtt     60
gggatgagta cgggattgca tttggaatgc ccacaaagca actagtcatc agacggctca    120
cgtgtgtctc tccgtacagt gccacgattg ctctagggag tgaaatgtcg ggtgggatag    180
aagatgttag agcagaggat atcacagcca tccacacaga atctgggtc aggatcaaaa     240 ctgctgtagg gagaggaggg tttgtgaagg acatatacgt gaagagaatg actatgcaca    300
ccatgaaatg ggtcttttgg atgactggaa attatgggtc acatgctgat aagaattatg    360
acccaaacgc actgccattg attcaaggca taaattacag ggacatggtt gcagacaatg    420
tgacaatggc ggcaagattg gagggcatcg caggcgatcc attcaaggaa atttgcatct    480
ctaatgtcac aatcggattg gcaccgaagg cgaagaaggt accctggacc tgcaccgaaa    540
ttgaggggat gacaagcggg gtaagtccac ggccatgtga tttgctaccg gatcaagggc    600
cagagaaaat cacatcctgt gatttccctc cggagaatat accaatcgac ttggtgcagc    660
tcaagacgtg ctccttcgga atgagttata tgtgaacttt gcttctctac taccatcaag    720
caatgtataa acactgctag ctccgagcaa aaaatatata taatctacta gttttctca    780 gttttggaaa aaaaaaaaa                                                799
```

<210> SEQ ID NO 49
<211> LENGTH: 1182
<212> TYPE: DNA
<213> ORGANISM: Populus tremula x tremuloides KR125
<220> FEATURE:
<221> NAME/KEY: misc_feature
<222> LOCATION: (1)...(1182)
<223> OTHER INFORMATION: n = A,T,C or G

<400> SEQUENCE: 49

```
accgttctca aggatctgat catgtctttg ttgcctctca cgattacggc gcttgtttcc     60
atgccatgga ggagagagct atggaagatg ggatcccaga gttttttgaag aggtcgatca    120 tattgcagac ttttggtgtc aaatttaacc atccatgcca agacgttgag aatgtcgtga    180
taccaccata catctcgccg ggaagcgtac ggacaaccct cgagaaatat ccgctgaccg    240
gccggcggga cgtttgggcc ttcttttagag gcaaaatgga agtgcacccc aaaaacatta    300
gtggacgata ttacagcaag aaagtgagga cggtgatatg gagaaaatac agcggtgacc    360
ggaggtttta tttgcaaagg cacaggtttg ccggttacca gtcagaaatt gtccggtcag    420
tgttctgttt atgcccttg ggatgggccc atggagccca aggctggtgg aatctgtngc     480
cttagggtgc gtgccggtga taattgcgga tggcatccgg ttgcccttcc ccaccgctgt    540
```

```
ccggtggtcg gagatatccc taaccgtggc cgaaaaggac gtggccaatc taggaacttt      600
actcgaccag gtggcagcta ccnanttgtc agccattcag aaaaacctgt ggaccccaga      660
tgttaggcgg gccctccttt tcaatgatcc agtgcaggga ggagatgcca cgtggcaggt      720
gctttatgca ttggcacaga agctggacag gtcgtacaga accgtgaggc tttcaaacca      780
ctagtgaagg tactttttg gggacccgag tgccagctaa ggaggtccgc ttttgccagc       840
taagagacat ggagcacagc tggattttta atgttttct tggattgatc aaaccatggg       900
aattttaaga ggcaaagagg tggggtccag cctatgcaga gattaagatt atctgcaatt     960
ttttgtgtgg tcccgtgact tgctcggtga gttggctgac tgtgattgat ggggctgaac   1020
ggtacatata attgtaaagc aatgctgtag atgagggaga ggtttctgtt ttgagaaatt   1080
atgagagaat aaatgcaaaa ataggccctg taaatactct aataatgagt cgaagtcgat   1140
tgcaatttac tgaaaaccca acccatttct aaaaaaaaaa aa                       1182
```

<210> SEQ ID NO 50
<211> LENGTH: 791
<212> TYPE: DNA
<213> ORGANISM: Populus tremula x tremuloides KR129B

<400> SEQUENCE: 50

```
ccatctcctt caggcactca tattctccgt acttttagc aaatggaagc taaaagacta       60
attttagctc tcttccttct cttcttgctc tctaaatcct ctgctttccc tagcagaaaa     120
tctcgagttc ataaaccatg caaaagatta gtcttctatt ccatgacat tatttacaat      180 ggcaagaact ccaagaacgc aaccgcggca attgtggggg caccagcttg ggcaacaag     240 accatattgg ctaaccaaaa ccattttggt gacttggttg ttttgatga ccccattacc     300 ttagacaaca acctacactc ggccccagta ggtcgtgccc aagggattta tgtgtatgac    360
aagaaagaaa tcttcactgc ctggctaggt ttctcttcg ttttaactc tactgagcat      420 aaaggaagca taaactttgc cggggctgat ccattgatga acaagactag ggatgtttca   480
gtgattggtg gtactggaga cttcatcatg gctcgaggaa tagccacatt gatgactgat   540
gcattcgagg gtgaagttta tttcaggctt cgtgttgata ttcagttgta cgagtgctgg   600
tgacagtttt tgcttcgagt tcagcatttg atggttctct cttttaatc ggttttccag   660 caaaattaag aagaaggttg atttcctttg cagttattga atcgagattc ttgtatcacc   720
aagtgtttca taattgaaat aacttttcat gaggttataa ttaactttta ttcttaattt   780
gttatcagtt t                                                          791
```

<210> SEQ ID NO 51
<211> LENGTH: 792
<212> TYPE: DNA
<213> ORGANISM: Populus tremula x tremuloides KR140

<400> SEQUENCE: 51

```
cttgttcgat ccctgcacta atcctgatta atgcctgcat tcccttttag attttgtgtt      60
tgattttgtc ctgtaaggag ctggatatgc gggatcatat ggagagattt gtagttcttc    120
cattctccat cgcctgtgct tctcactcca gtgttgatgt ggcctccagt gaatcctcca    180
agaaaccaag acccgaaacc aaatcacatg catcaagagg acaagaaggg gaggaaagct    240
cttgtaaaga aaagacgaag aacagtacac ttggtttcct gctggctctt ccaaagcctt    300
gcatatccga tagcttgcac aaattgatta gaggcatcaa gactctctcc caagtatttg    360
tgtacaagga agaagacgag gagctaatgg aaagagagat ggaaatcgga tatccaactg    420
```

| | |
|---|---:|
| atgtgaagca tgtaacacac ataggattgg atggaactac gatgacaaat cctataaagg | 480 |
| gctgggattg tctgaaatct ccagaaataa ttccattccc ttcatttact ttaaggcagt | 540 |
| tcgagcttgc aatggctgca caagctcatg gacctcttgt tggggtcgat cattccaagc | 600 |
| ttgtttgatt cattgatttt tcttttcatt tcctgatctt gtttctttga cactagatga | 660 |
| ctgatgtgat gaagattgat caatgttttt gatggaggca ctggttgcag tgatgtgttt | 720 |
| ttggtgtttg tgtgggacct tgacaatgtt tttctgggtg ccattgaaa ttgttcttgc | 780 |
| aaaaaaaaaa aa | 792 |

<210> SEQ ID NO 52
<211> LENGTH: 682
<212> TYPE: DNA
<213> ORGANISM: Populus tremula x tremuloides KR152

<400> SEQUENCE: 52

| | |
|---|---:|
| cttttcagtc gtgagttaag cagcacaaca agcatgagag gcactctctg ttatgttgct | 60 |
| ccagaatatg gtgggtgtgg atacttgatg gagaaggctg atatatacag cttaggggtt | 120 |
| ctaatcctcg tgattgtctc cggtaggagg ccattacatg ttcttgcttc accgatgaag | 180 |
| cttgaaaagg caaatttaat aagctggtgc aggcagttag ctcaaactgg gaacatctta | 240 |
| gaacttgtag atgagagaat gaaggacgaa cacaataagg agcaggcaag cttgtgtata | 300 |
| aacttggctc tgacatgctt gcagaggatg cctgaattga ggccagatat tggagagata | 360 |
| gtgaagattc tgaaagggga gatggatcta ccgcatcttc ctttcgaatt ttctccctcc | 420 |
| ccaccttcca aattgtttag taggtcaagg agaaaacaaa atctaatgc agagtaggtt | 480 |
| cagtacatat tctttgtttt cttccattga tcatgttttt actgagtggt acataggatg | 540 |
| ggagctgtaa tctgataaca cattatggat gtgaaggtat tttcttaatt cgagtctaca | 600 |
| atgctatatg tacatcagaa tctcagatga gtggattttg cttccttgt ctctaattgg | 660 |
| atatggaaaa aaaaaaaaaa aa | 682 |

<210> SEQ ID NO 53
<211> LENGTH: 911
<212> TYPE: DNA
<213> ORGANISM: Populus tremula x tremuloides KR163

<400> SEQUENCE: 53

| | |
|---|---:|
| ttgtgtttga agaatggggt ggagatccaa atgggatttc tttggttaga agagatgtag | 60 |
| acagtgtgtg tgctgatatt tatgagtggc agccaacttt gatgaattat cagatgcaag | 120 |
| catctggtaa agtcaataag ccactgaggc ctaaagctca tctgtcatgt ggccctggac | 180 |
| agaaaatcag atcaatcaag tttgccagct ttgggacacc agaagggggtt tgtggtagct | 240 |
| atcgccaggg aagctgtcat gccttccact cttatgatgc ttttaacaat ctttgtgttg | 300 |
| ggcagaattc atgctcggtg actgtagcac ctgaaatgtt tggggagat ccttgcctga | 360 |
| atgtcatgaa gaaactagca gtagaggcca tttgcagctg atgagctaca acggctgaag | 420 |
| taaatgaaat aaagaagatt ctggatttga ttttctcacc ctccaataca gcatcttcgg | 480 |
| tatactattt tatggttaaa ttaaaagctt cacaaccagg agcactacaa acatttgttc | 540 |
| tggcttttcc agggtgaagt tgtacaaata tacagcacac catctggtcg atagccatat | 600 |
| agattgtgca aatgattgca gataagcttt tttatgtagg cggagccagt gtttattgtt | 660 |
| ggtgtcctgt atgtatatgc agcaaacaag tgaaggagtg ggttcggtag aagcacattg | 720 |

```
agatgaaaaa ctaaacgagt ccatgtgcaa atttggtagt ttttagagta tggaaagcct    780
ctggtttcct gtgatcttat attttttatt caatgtaaac ttcctgggaa ccccacttcc    840
tttgttgcta tgttcttgta agaaagtttc taagttaaag aaatgatacc aaacttcgga    900
aaaaaaaaaa a                                                         911

<210> SEQ ID NO 54
<211> LENGTH: 725
<212> TYPE: DNA
<213> ORGANISM: Populus tremula x tremuloides KR221

<400> SEQUENCE: 54
ccttcggcga gctcaccaga tgtgtcctga ctcgcttgga tgacaacaag caactggaat     60
tattgctgca ttaactatat tataagaagc agttactcag tggggattct ggtgggcatt    120
tgctgtcatg gacactacca gatgagagct tgctgacgtc atctaatcag gggtgagagg    180
ggggaaaact gatttaagcg tgattgtttc agctcgtggc agctatttat tatctattga    240
aatcctatgc gggttttgtc tgccaccacg gcaaaggaag taaaggattc tatgttcgta    300
atacattgag aagggagaac aaggcagcag ggctggcctg ggattgaaag aggacaggca    360
aaaagaagat gagatctttt atagatgact gataaatgtc gacttcctgg caagcatgaa    420
gactctcgtg ccaggcttct tattgagaat ggaaagtgga gtcttgcttc ttgttgtact    480
ctgggttctt ggcgaggaca ttttgattt tgcacgtgaa cagagtcatt aggttgtttg    540
ttcaatgtac atagatggaa ttaccaacag tgtgttatga agttgtatag agaaaaagtg    600
tgcgcaagga atgagagct gtgaaaccac ctggccaagt taattgggct attgtattct    660
tcgacttaat tttttttaaaa tagtgcaatg gggcacccac tgcccatttc ttgctaaaaa    720
aaaaa                                                                725

<210> SEQ ID NO 55
<211> LENGTH: 949
<212> TYPE: DNA
<213> ORGANISM: Populus tremula x tremuloides KR224

<400> SEQUENCE: 55
gctagctgta tagttgaaga gaagctgaag aggaagagat ggcagagcag gaggtgaaga     60
aggtagaggc tgtaacgccc gtggctccag ctccagtgga aactaaaagt gatgtggccg    120
atgggaaagt tacggctcca ccacctccag tggctgcaga gaaagagaag gcagccactg    180
ctgctgagga atcaaaagct cttgctgttg ttgaaaagac agaacctgct tcgaagaagg    240
tttcaggcgg atcaattgac agagatgtag ctcttgctga ccttgaaaag gaaaagagac    300
tttcctttat caaggtatgg gaagacagcg agaaaactaa agccgagaac aagtctcaga    360
aaaatttctc tgctgttgtt gcctgggaga acagcaaaaa ggcagctctg gaagccaaac    420
tgagaaagag ggaggaaaaa ctggagaagc aaaaggcaga atatgcagag aaaatgaaaa    480
acaggattgc tttaattcac aaagaagctg aggaaaagaa ggcaattgtg gaagccaaac    540
gcggggaaga ggtcttaaag gcaggggaga cggctgcaaa ataccgtgct accgggcaaa    600
ccccgaagaa gctccttggt tgcttctgaa gtcgaactg taggagcatg gaagcggaaa    660
gttgaatcat aattcttcct ctgcatatag tgtttttaac tccttgcttt tcttgcttgc    720
ttgttattat tattattatt ttttttccca catggtttca tgtcttcttt cattaaacat    780
cggcaaattt aaatattcag tgtgtttatt atgtatagga atacaatatt tgatctgtga    840
gaaacaagct taacatgttt gtgaagtttgg cttctcttgg catactagtg aggttgcctt    900
```

```
gtcgaacaca tccttttcat attttttcggt atcttcccaa aaaaaaaaa          949
```

<210> SEQ ID NO 56
<211> LENGTH: 1226
<212> TYPE: DNA
<213> ORGANISM: Populus tremula x tremuloides KR235
<220> FEATURE:
<221> NAME/KEY: misc_feature
<222> LOCATION: (1)...(1226)
<223> OTHER INFORMATION: n = A,T,C or G

<400> SEQUENCE: 56

```
gtaaagctcc gtattttttag ctgggtttct cttaaaaaat ggaacttggg ctcgtggggt   60
tgtagagagc agcctggatt gcagggacgc tgcctatact tatagcttca ctgccatgtg  120
cttggctggg ttcttttcat ggacttgttt tggggtttgc aaggagagga aagatcatgc  180
aatcatcatc tcatcgtaaa ttcactgctc cccaaagatt ctttttctcat ttctatgtgg  240
tggctgtggc gtggacaact ctcttgcttc ttggaacatc gatatatgct tatagaatga  300
caccaatagt ttctgagccg ttttttctact ctgatctagg cagctacttg gcaggacgat  360
caaacatatt ctcatttcat cgatcacggt tgatgagttt agagaataga tacagggttt  420
ggctttctgt gtttctgctt ttgctaatgg aagttcaagt ctcgaggcgt cttttcgaga  480
cngcatatgt atttaaatat agcgcctctg ctcggatgca catttttggc tatcttactg  540
gctattcttc tacacagcag cgcctctgac actctgctgt acctgtgcac ccgaagtact  600
caaatttggc ataaatgaag tgtctgagct cattcttaaa ggcacaagct caatgcaaaa  660
cattgaattt cactggtggg actttgttaa ccctttattg aagcttggat ggtgccagtg  720
gattggcgca gttatatttc tttggggttg gattcatcag catcgttgcc atgcaattct  780
tggctcacta agggaacacg tgggaaaggc tgatgaatat gtaattcccc gtggtgattg  840
gttcgagatt gtttcatctc cacactattt ggcagagatt gttatatatg ctggcatggt  900
ttttgctagt ggaggggcag acctcaccat ttggttagtt tttggatttg tggtgtcaaa  960
tctggtgttt gcagctgcag aaacacacag ttgccatcgc gtgattaaga tgatggctac 1020
agcaaagtct tgacaagagg taggaaaaaa tttattagag aagcaaatta gtttggtgaa 1080
tgtttatgtt atgtccagat gccctttctg aggcgattga attctatctg attgtgtagt 1140
tcctgtaagc ttcagacatc tcatccaatt ggatggtgca attactataa tgaattgtgc 1200
attcaaattg ttgctcgaaa aaaaaa                                     1226
```

<210> SEQ ID NO 57
<211> LENGTH: 1020
<212> TYPE: DNA
<213> ORGANISM: Populus tremula x tremuloides KR242

<400> SEQUENCE: 57

```
gtcaagataa agtcccattc ttttttcctag ccccaagttt gtttgagggg tgataaaaaa   60
tgaaccaaga gatgaatggt gttgacactg agattgatca gaaccaccaa gagaatgtgc  120
aagagaaaat cgattatgtg tttaaggtgg tggtgatcgg tgactctgca gtgggcaaga  180
cgcaaattct ttccaggttt accaagaatg aattctgctt tgattcaaag tctaccatcg  240
gtgtcgagtt cccagactag gactgtcatc attaaagaca aggtcatcaa ggctcagatc  300
tgggatactg ctggccaaga aaggtaccgg gcagtgacaa gcgcatacta tagaggggca  360
ctaggggcca tgttagtcta cgacattacc aagagaccaa cgtttgatca tgtggctagg  420
```

```
tgggtggagg agctccgagc ccatgctgac agctcaattg tgatcatgct gatcggaaac      480
aaggctgatc ttgtggacct cagggcagtt ccaacagaag acgcggtgga atttgcagag      540
gatcaaggcc tctttttttc tgagacatca gcccttagtg gtgacaatgt ggatggtgca      600
tttttcaggc tgctagaaga aatttacggt gtgatttgta agaagtcatt ggaatgtggc      660
aatggaaaac ccatgctgc tgatgccata acgcttagag gttctaagat tgatggcata      720
tcagggacgg atctggggat tagtgagatg aagaaattat ctgcttgctc gtgttgattt      780
gatcatttct cttgtgaatt gtgtactata agacttcacc actcccatgt tcttaattga      840
ttctgtggct ttctttggaa agtggtgatc ggtcgtgtgg tgagggtggc aagtttttc      900 ttttctgtga cctgtcaaga ttttagcagt attgtacttg tcttacagaa cccatgaatt      960 tggtttttttt atatgtattg atttggatgg atggttttcc ttttcctctg aaaaaaaaaa     1020
```

<210> SEQ ID NO 58
<211> LENGTH: 844
<212> TYPE: DNA
<213> ORGANISM: Populus tremula x tremuloides KR292

<400> SEQUENCE: 58

```
cacaaagcta gatttttttg tgcctctggc atgagtatat gaacgcttct ctatgggttt       60
gtcatgtgga gaggatgatt ttgaaaagaa tggaagtcat gaagttccgt taatagttga      120
tagcagaggg actagagtca gcggtggcta tatggattta caacatcttc atcatgcagt      180
tgagtacgag gtcgaattct ggccagttga cacccaatg gaaccacagg atgaagatcg      240
tcctgtcaaa tgtccaatgc caacctcttc tgttatcaag aatggaaggg cgcatgagga      300
gagattagag aagagagcgg acgacctcca actacctgcg gtaatgaaca acaaggcat      360 tgttgtggtg gctgcagagc cccagtccg agcagtgcgt aaaaggcacc atacacttac      420
ccgccaggac caccgtgtaa tagcacctga tctaacaagg atggcttcac ttcctgctct      480
gccaactcag aacgtcacca tttttcaaat gcttcaagaa ctcgacaagt tcgatcagta      540
ttaaaaaggt ataagaata aattaggaaa cccacatttc cgctccatct agctttaata       600
gctacttttc aatccattgc ggagcggtca atgaattctt catgatttgt atttcgggcc      660
aatagggaaa gaaatatcat agatatgcgg tataagaagc actcttattg tactatgatt      720 tttattttttt atatattctg tagaatgtgt cttccagcct aattgtaggt ttcctttatc     780
atttctttgt tcagatttgg atggataatt agcatgacac tctgcaatac cgaaaaaaaa      840
aaaa                                                                    844
```

<210> SEQ ID NO 59
<211> LENGTH: 1003
<212> TYPE: DNA
<213> ORGANISM: Populus tremula x tremuloides KR313

<400> SEQUENCE: 59

```
gaaaaattct cctggaccag ctaagagaga gcttagacaa gctactagac aggcacttca       60
attgcttcaa gacaactatc cagaatttgt ggccaaacag atcttcatca atgttccctg      120
gtggtaccta acagtaaata gaatgataag tccattttta acccagagga ccagaagtaa      180
gtttgtcttt gttggtcctt ccaaatctgc cgaaacccct atcaggtaca tagccgctga      240
gcaaatacca gtgaagtacg gaggcctaag caaagatggt gaatttggct cagctgacgc      300
tgttactgag attaccgtga agccagcagc aaaacacacc gtagaattcc cagttactga      360
gacatgcctt ttaacatggg aagtgagagt tgcgggatgg gatgtgagct atggtgcaga      420
```

-continued

```
atttgtacca agtgctgaag atagctacac agtgatcatc caaaaggcta gaaaggttgt      480
tgcaactgaa caaccagtgg tttgcaacag tttcaaaatt ggtgaacctg gtaaagttgt      540
tctcaccatt gacaatacca catccaagaa gaagaagaag ctcctctatc gcttgaaaac      600
caagcccgct tcttctgatt aattaaggga ctatatatag tgaaacaata atagaagatt      660
ttgcttacat tcttgctgct gctgctgctg ccaattttat caacatgatc atatcacagc      720
ttgaaggtgt tctgagggtc tcgatcatgg agaagataaa gaaatcttga agatgtttat      780
ttatatgttt atttataatt gaattttgtt ttggtgtgga atggattaag gatgttgtgc      840
aattgaaggc tagaagcatg tgtggggata gggaagaagc tccattacta gtgccaagag      900
ttttctttgt aaattcgtta tggctttctt tctctttccc tgtaagtatc ttttggacat      960
attatgatat taatgaagac agtatctttc ataaaaaaaa aaa                       1003

<210> SEQ ID NO 60
<211> LENGTH: 896
<212> TYPE: DNA
<213> ORGANISM: Populus tremula x tremuloides KR

<400> SEQUENCE: 60
cattatccca aaaacgagc aaggcagata cagcagccaa aaccatgtca cccggtcccg       60
tcgttgaggc tgaacccgcc gccgccgtgg aagatacaca gaagaagaag cctcctcagc     120
aggacgtgga tgaacctgtg gtggaggacg tgaaagaaga tgagaaggaa gaggacgacg     180
acgatgatga tgaagacgac gatgatgaag atgatgacaa ggatgatgat accccaggtg     240
ctaatgggag ttccaagcag agcagaagtg aaaagaagag tcgcaaggca atgttgaagc     300
ttggcatgaa acctgttact ggtgttagca gagtcaccat caagagaacc aaaaatatac     360
tgttttttat ctcaaagcct gatgtcttca agagccaaaa ttctgagacc tatatcatat     420
ttggagaggc aaagatagag gatttgagct ctcagctgca gacacaggct gctcagcagt     480
ttagggtgcc agacatgtca tctatgctac caaaatcaga tgcttctact gcagctgctg     540
ctgcaccagc agatgaagaa gaggaagaag tcgatgagac tggggttgag cctagggaca     600
ttgatcttgt tatgacacag gctggagttt ctaggagcaa ggctgtcaag gctctccaga     660
cgaacaatgg ggacattgtc agtgctatca tggagcttac tacataggtt ggctccctgg     720
ttactctcct attttctgct cacaagttct tggaacaatt taatcatggt agtcacattg     780
gcttgccatc tatgaggtcg ctaattatcc attgtttgtg tcaaatttga gattattacc     840
tattgcggtt tttctttagt agcaagctct tattgtgctc tttgcaaaaa aaaaaa         896
```